US008923959B2

(12) United States Patent
Boveja et al.

(10) Patent No.: US 8,923,959 B2
(45) Date of Patent: Dec. 30, 2014

(54) METHODS AND SYSTEM FOR REAL-TIME CARDIAC MAPPING

(71) Applicants: Birinder Robert Boveja, Greenfield, WI (US); Angely Widhany, Naples, WI (US)

(72) Inventors: Birinder Robert Boveja, Greenfield, WI (US); Angely Widhany, Naples, WI (US)

(*) Notice: Subject to any disclaimer, the term of this patent is extended or adjusted under 35 U.S.C. 154(b) by 0 days.

(21) Appl. No.: 13/775,040

(22) Filed: Feb. 22, 2013

(65) Prior Publication Data

US 2014/0243641 A1 Aug. 28, 2014

Related U.S. Application Data

(63) Continuation-in-part of application No. 13/595,451, filed on Aug. 27, 2012.

(51) Int. Cl.
| | | |
|---|---|---|
| A61B 5/04 | (2006.01) |
| A61B 5/02 | (2006.01) |
| A61B 8/00 | (2006.01) |
| A61B 6/00 | (2006.01) |
| A61B 18/00 | (2006.01) |
| A61B 5/042 | (2006.01) |
| A61B 5/044 | (2006.01) |
| A61B 5/046 | (2006.01) |
| A61B 5/0472 | (2006.01) |
| A61B 6/03 | (2006.01) |
| A61B 8/08 | (2006.01) |
| A61B 8/13 | (2006.01) |

(52) U.S. Cl.
CPC ............... *A61B 6/463* (2013.01); *A61B 18/00* (2013.01); *A61B 5/0422* (2013.01); *A61B 5/044* (2013.01); *A61B 5/046* (2013.01); *A61B 5/0472* (2013.01); *A61B 6/032* (2013.01); *A61B 6/485* (2013.01); *A61B 8/0841* (2013.01); *A61B 8/13* (2013.01)
USPC ........................... 600/509; 600/450; 600/508

(58) Field of Classification Search
CPC ..................... A61B 19/5244; A61B 2013/508; A61B 5/0538
USPC ........................................ 600/450, 508–509
See application file for complete search history.

(56) References Cited

U.S. PATENT DOCUMENTS

| | | |
|---|---|---|
| 8,275,452 B2 | 9/2012 | MacAdam et al. |
| 8,369,922 B2 | 2/2013 | Paul et al. |
| 8,412,307 B2 | 4/2013 | Willis et al. |
| 8,421,799 B2 | 4/2013 | Markowitz |
| 8,428,700 B2 | 4/2013 | Harlev et al. |
| 8,433,387 B2 | 4/2013 | Voth et al. |
| 8,433,394 B2 | 4/2013 | Harlev et al. |
| 2012/0265084 A1* | 10/2012 | Stewart et al. ................ 600/509 |

* cited by examiner

*Primary Examiner* — Nicole F Lavert
(74) *Attorney, Agent, or Firm* — Boye Fredrickson, S.C.

(57) ABSTRACT

A method and system of electroanatomical mapping comprises bringing a patient's image such as a fluoroscopic image and intracardiac signals into a computer based mapping system. Electroanatomical mapping or superimposing of cardiac electrical activity on fluoroscopic image is provided by placing visual indicators on electrode pairs of various catheters including standard catheters and ablation catheter. Visual indicators are coupled or linked to underlying electric signals from those electrode pairs via software coding, whereby electrical activity sequence of the heart is provided and updated in real-time on fluoroscopic image. A combination of fluoroscopic image and CT or MRI may also be used. The mapping system further comprises various algorithms for aiding in cardiac mapping and ablation of cardiac arrhythmias.

20 Claims, 55 Drawing Sheets

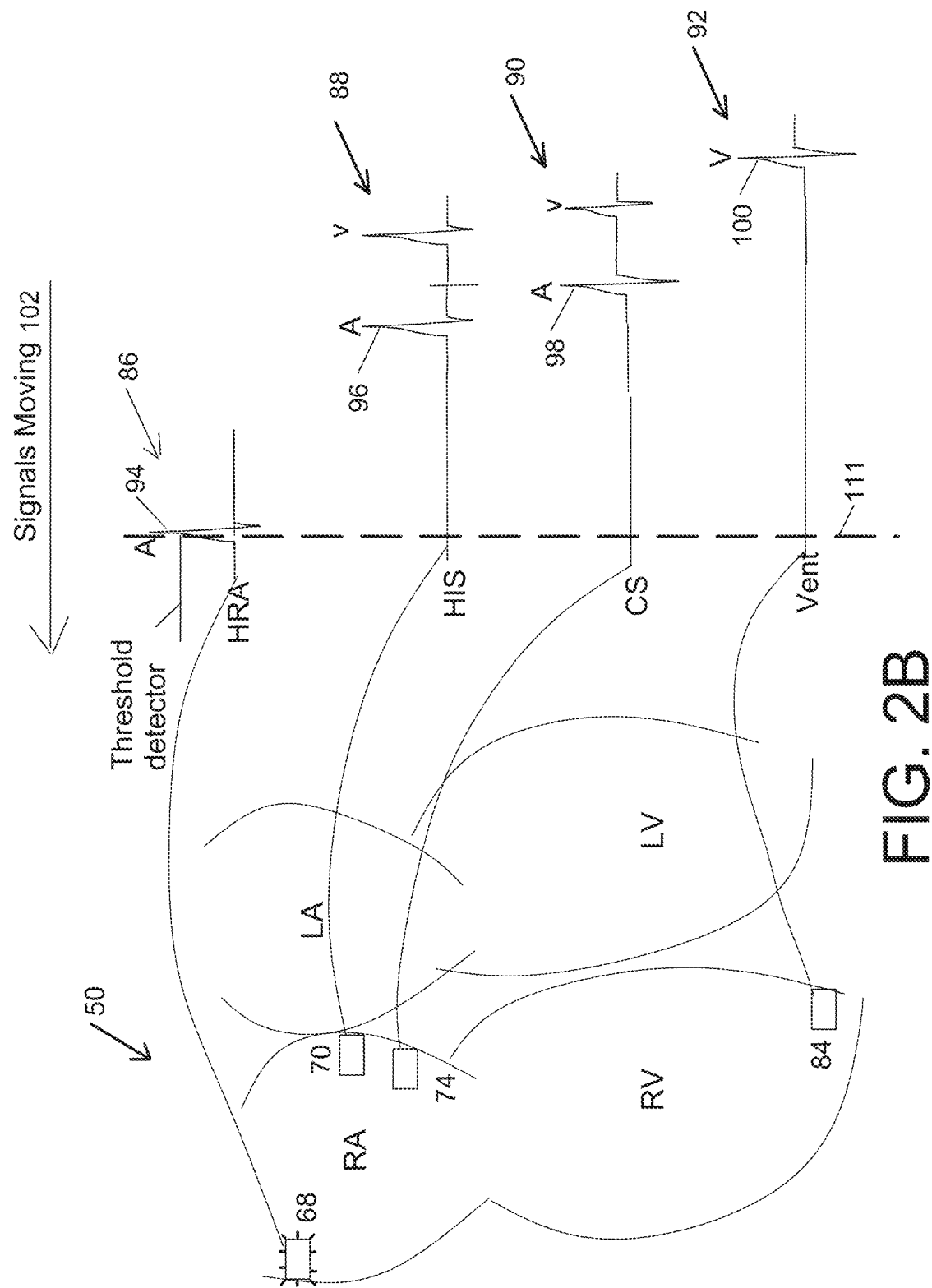

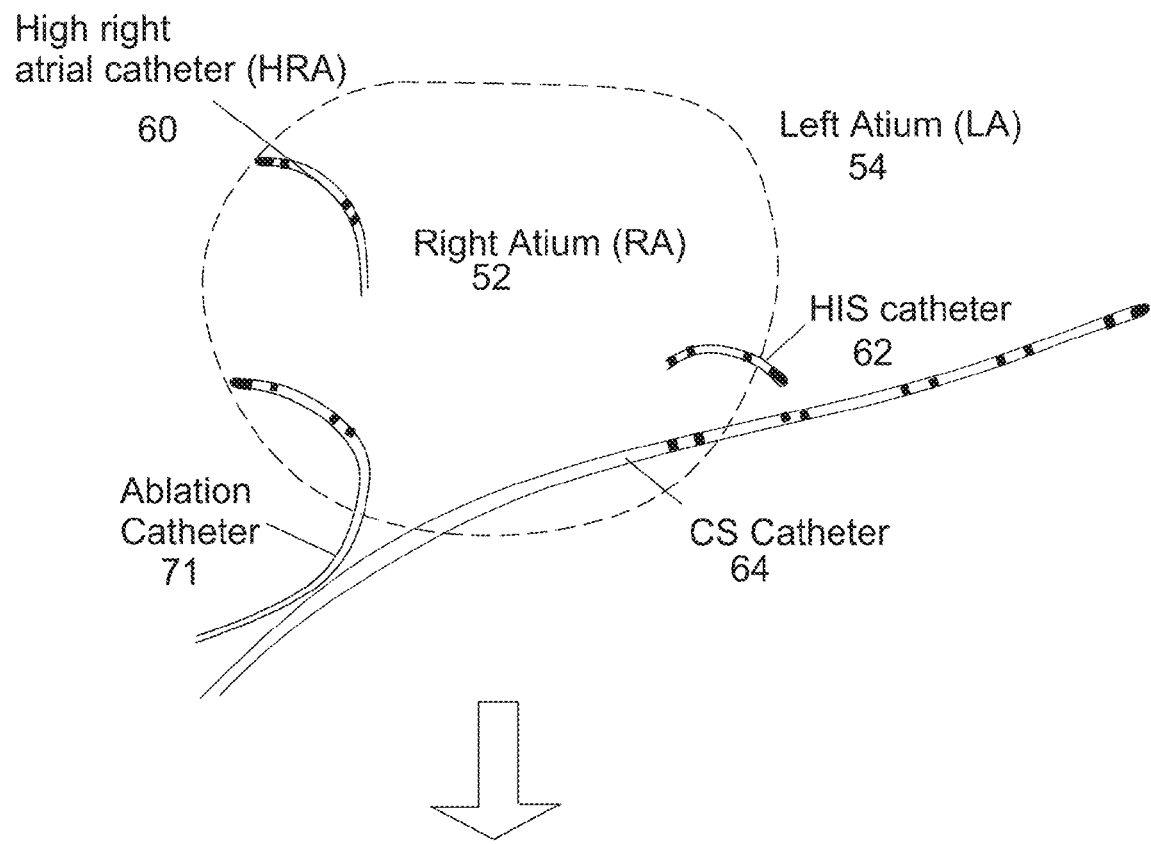
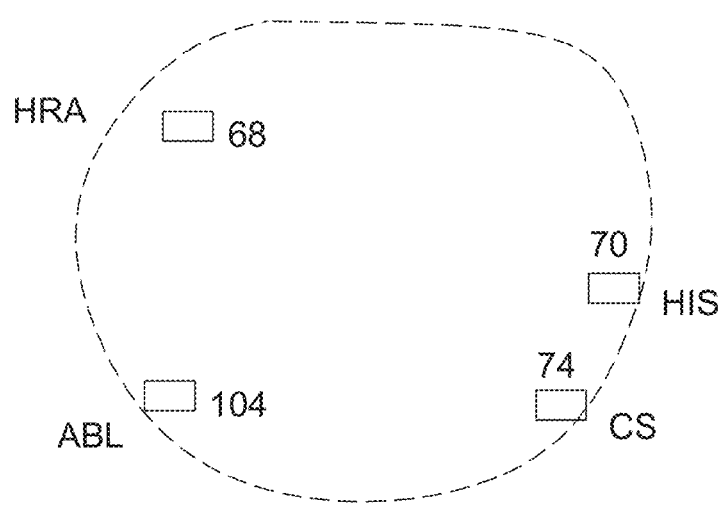
FIG. 5A

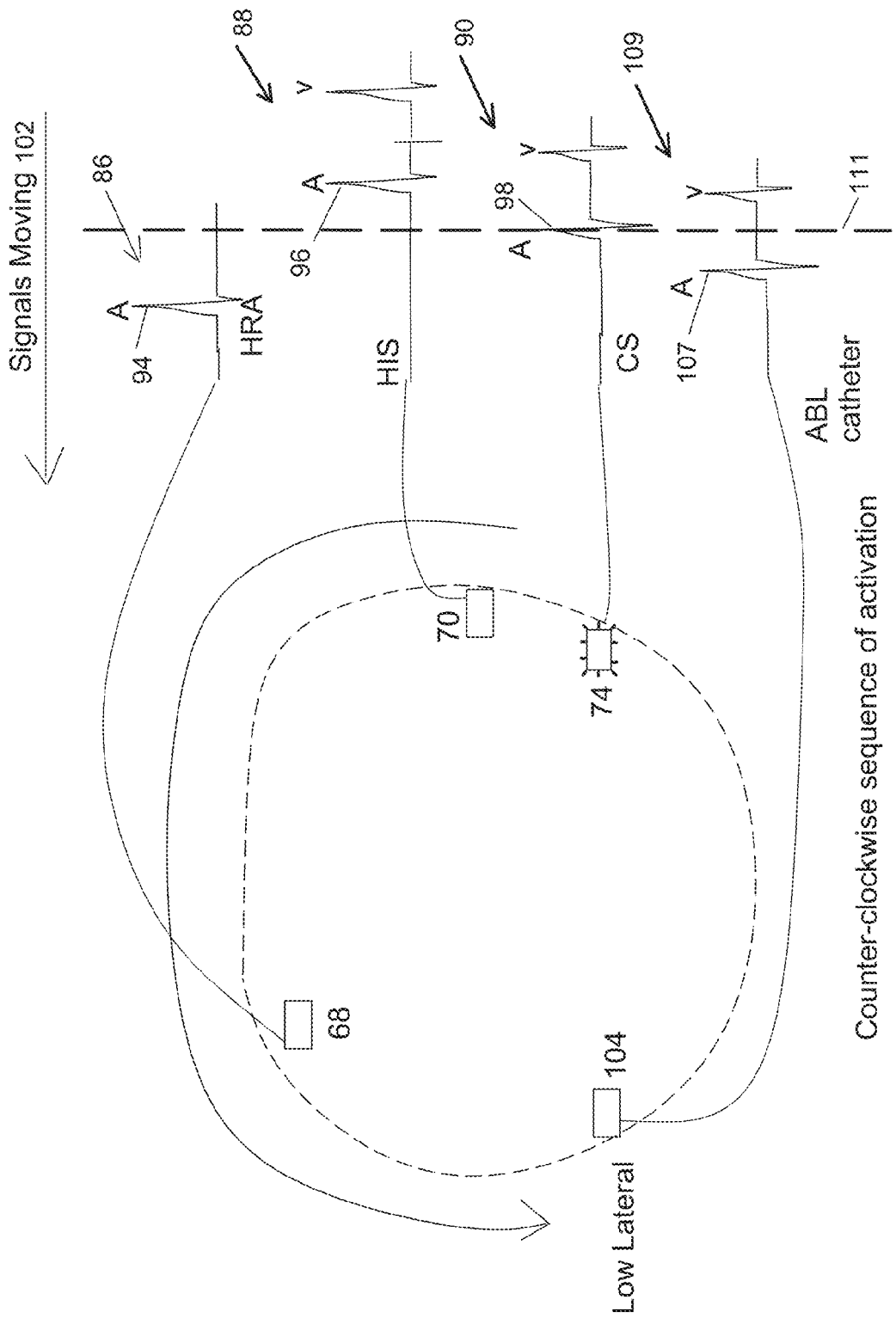

Clockwise sequence of activation

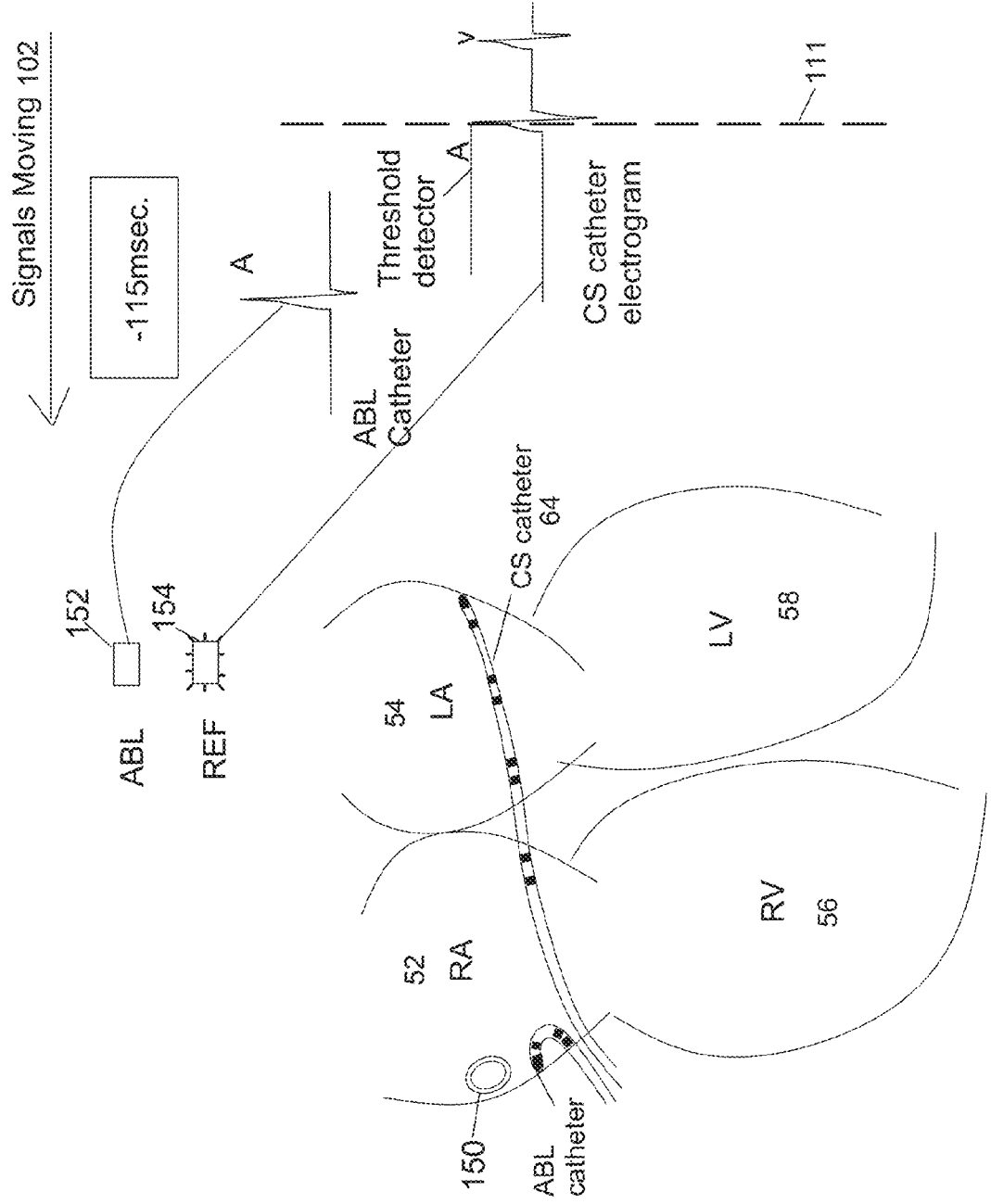

Algorithm to determine peak-to-peak value of each pulse

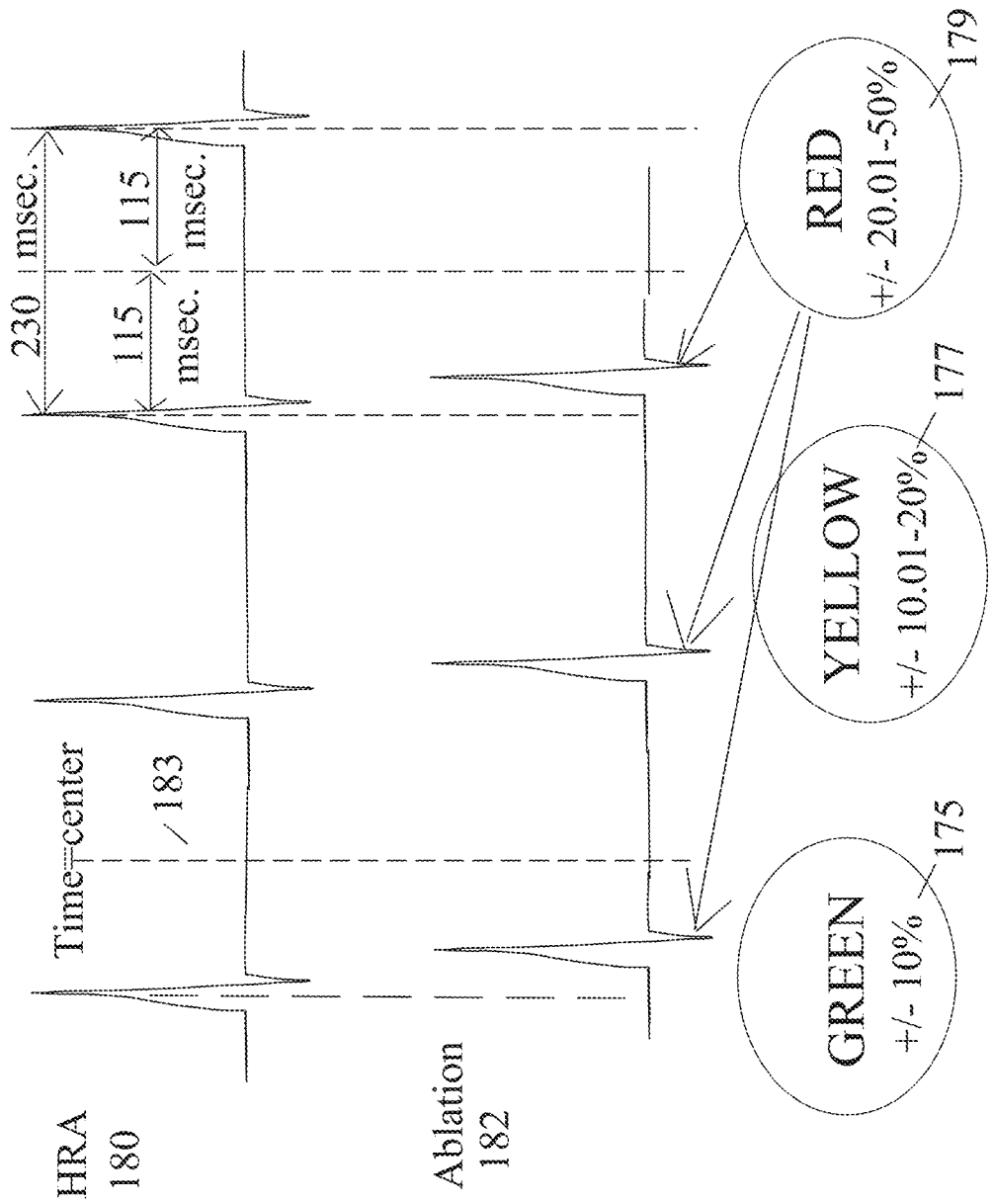

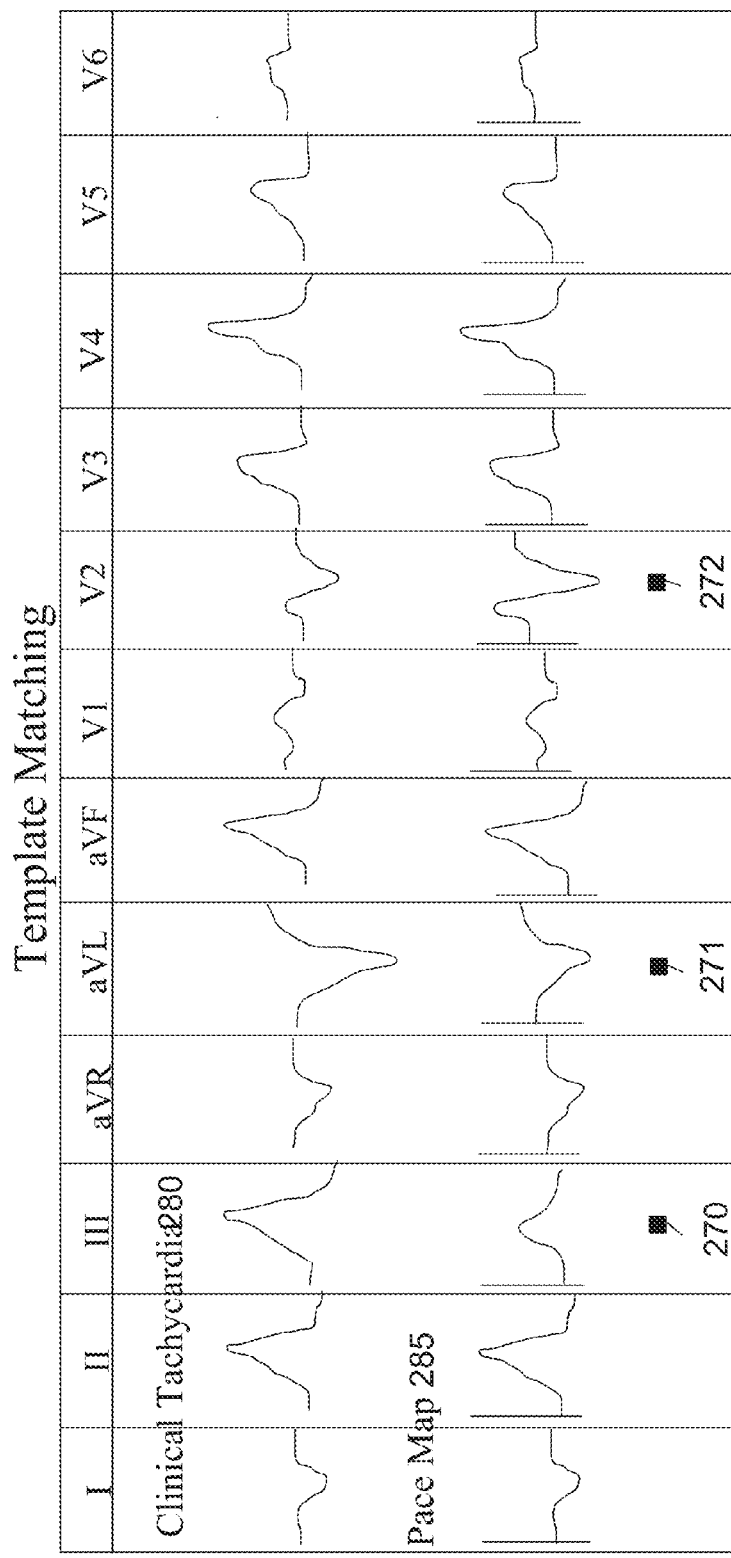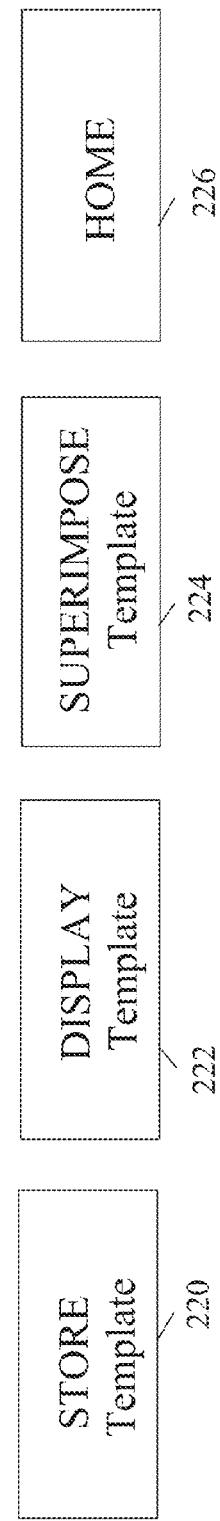
FIG. 28

Template Matching

| I | II | III | aVR | aVL | aVF | V1 | V2 | V3 | V4 | V5 | V6 |
|---|---|---|---|---|---|---|---|---|---|---|---|
| >95% | >95% | 65% | >95% | 50% | >95% | >95% | 80% | >95% | 70% | >95% | >95% |
| | | 273 | | 274 | | | 275 | | 276 | | |

Clinical Tachycardia with Pace Map (superimposed)

Template Match: 8/12

| STORE Template — 220 | DISPLAY Template — 222 | SUPERIMPOSE Template — 224 | HOME — 226 |

SUGGESTED RESULTS/DIAGNOSIS:

LAA
Left PV
Superior MA

NEXT

BACK TO PROGRAM

FIG. 41

METHODS AND SYSTEM FOR REAL-TIME CARDIAC MAPPING

This patent application is a continuation-in-part of U.S. patent application Ser. No. 13/595,451 filed on Aug. 27, 2012, entitled Methods and Systems for Mapping and Ablation of Cardiac Arrhythmias Comprising Atrial Flutter.

FIELD OF DISCLOSURE

The present disclosure relates to cardiac mapping technology, more specifically a novel real-time, direct visual mapping method and system for mapping and ablating cardiac arrhythmias.

BACKGROUND OF THE INVENTION

Many cardiac arrhythmias that formerly required the use of potentially toxic drugs or cardiac surgery can now be routinely cured (or at least palliated) in the electrophysiology laboratory by means of transcatheter ablation techniques. The basic idea behind transcatheter ablation is to position an electrode catheter to a critical area within the heart, and to apply damaging energy through the catheter in order to create a discrete scar. Strategically placed scar tissue, since it is electrically inert, can disrupt the pathways necessary for pathologic tachyarrhythmias.

Prior art mapping systems are indirect, complex, expensive and cumbersome. They can run dynamic propagation only in a review mode. In today's healthcare environment, there is critical need for a system that is direct, inexpensive and display's electro-anatomical information in a simple manner.

Examples of currently available 3-D mapping systems are Biosense Webster's Carto® mapping system, which is electromagnetic based, and St Jude's-ESI Navix® mapping system which is electrical impedance based. St Jude-ESI also has an Array® mapping system in which a balloon is placed inside a cardiac chamber.

Anatomical mapping systems provide the three-dimensional (3D) position of a navigational catheter within the cardiac chamber of interest and, in some instances, can also be used to construct 3D maps of the cardiac chamber. Systems such as CARTO (Biosense Webster, Diamond Bar, Calif.) use the electromagnetic position of the catheter tip relative to an electromagnetic locator pad which is placed below the patient and a reference catheter at a fixed external (usually posterior) location. LocaLisa (Medtronic, Minneapolis) and NavX (St. Jude's Medical, Minneapolis, Minn.) systems use voltage gradients generated by external electrical fields to spatially orient and localize the catheter tip. The EnSite system (St. Jude's Medical) uses an electrically-coded catheter and a multi-electrode mapping balloon to create maps and define the location of the navigational catheter. The CARTO, Ensite, LocaLisa, and NavX systems have been used to create 3D maps of the left atrium (LA) and will be described in more detail.

The CARTO system provides electroanatomic mapping based upon the premise that an electrical current is generated when a metallic coil is placed in a magnetic field. The magnitude of the current depends on the strength of the magnetic field and the orientation of the coil in the field. The CARTO system consists of a magnetic field emitter mounted under the patient, a location sensor inside the mapping and ablation catheter tips, and a data processing unit and graphical display unit to generate and display the 3D model of the cardiac chamber of interest. Data on the amplitude, frequency, and phase of the magnetic field are gathered and analyzed by the processing unit and displayed on the display unit. The CARTO mapping system uses a triangulation algorithm in which a sensor in the catheter tip allows the determination of its distance from each coil. In addition to the x, y, and z coordinates of the catheter tip, the CARTO mapping system can determine three orientation determinants—roll, yaw, and pitch. The position and orientation of the catheter tip can be seen on the screen and monitored in real time as it moves within the electroanatomic model of the chamber being mapped.

Since the CARTO mapping system is not an imaging technique, fluoroscopy is initially used to establish orientation by using generally known anatomic locations in the heart as references for the later creation of the model of the mapped chamber. An electromagnetic anatomical reference patch is placed on the back of the patient and is used to track the mapping and ablation catheter. For activation mapping, an electrical reference such as an ECG signal or an intracardiac recording is used. For intracardiac recordings, coronary sinus recordings are often selected because they are usually stable. For activation, points taken by the catheter are color-coded orange, yellow, green, blue and purple for progressively-delayed activation areas. Similarly, the voltage map is also color-coded and superimposed on the anatomic model. Using these techniques, both the mechanism of the arrhythmia and the 3D anatomy can be created. However, creation of an electroanatomic map may be a lengthy process involving the tagging of many points, depending upon the spatial details needed to analyze a given arrhythmia. Lack of accurate ECG and respiration gating and non-real-time data are other limitations of this technique. Furthermore, the catheters used are very expensive and fluoroscopy is always used as a backup to identify the location of catheters.

Non-contact mapping using the EnSite system is based upon the premise that endocardial activation creates a chamber voltage field which obeys LaPlace's equation. The EnSite system includes of a multi-electrode balloon which is placed inside the heart chamber of interest. The balloon or multi-electrode array is comprised of a braid of 64 polyamide-insulated, 0.003 mm diameter wires. For electrophysiologic studies, any mapping catheter can be used. The catheter location system uses a low-level, 5.68 kHz current emitted by a distal electrode which returns to each of two intrachamber ring electrodes on the multi-electrode array. Since the position of both the array electrodes and the current sink electrodes are known, a custom algorithm determines the position of the roving catheter by demodulating the 5.68 kHz potentials. The mapping catheter is moved around the chamber to create a 3D map. A high-resolution activation and 3D map can be created using custom-built algorithms. The EnSite system, like the CARTO system, has been used to treat arrhythmias including atrial fibrillation, atrial flutter, atrial tachycardias and ventricular tachycardias. Again, like the CARTO system, the EnSite system is very expensive, its resolution depends on the number of points taken, and a fluoroscopic system is commonly used to confirm the location of catheters.

The LocaLisa system uses 1 mA-current-generated electromagnetic fields at approximately 30 kHz, emitted from cutaneous patches placed on the subject's chest. These patches are positioned to create a 3D axis system. In addition to the connection of the position reference catheter and a mapping-ablation catheter, the LocaLisa system provides several other channels on which recordings can be made from several different catheters. Catheters in the subject's heart receive these signals, and the position of the catheter can be determined. One limitation of the LocaLisa system is that it merely provides the user with information about the catheter position—no geometric anatomical model can be created.

The NavX system, in addition to having all of the features of the LocaLisa system, can also, similar to the CARTO system, create activation maps and 3D anatomical maps of the chamber of interest. As described above, these technologies have several limitations. As in other electroanatomic mapping systems, the accuracy of the chamber reconstruction process is directly dependent upon the number of the points taken and the position of the catheter. Another significant limitation is that the heart is essentially considered a rigid body over which maps such as activation map are displayed. Also, cardiac chamber distortion due to cardiac and respiratory motion is not taken into account if a significant change in heart rate occurs from the time the map was created to the time therapy is delivered. However, the biggest drawback, as described before, is that these systems are expensive, require separate mapping systems, and do not provide real-time visualization of the chamber. Consequently, fluoroscopy is used almost all the time to confirm location of the system.

The current mapping systems are indirect, expensive, and complicated. The present disclosure addresses one or more of these problems by providing a real-time mapping system, which can use readily available fluoroscopic image, and is simpler to operate and is cost effective.

SUMMARY OF THE DISCLOSURE

The current disclosure discloses novel methods and system of cardiac mapping useful for diagnosing and ablation treatment for various different types of cardiac arrhythmias.

In accordance with one aspect of the present disclosure, an electroanatomical mapping system and method comprises bringing a patient's image such as a fluoroscopic image and intracardiac signals into a computer based mapping system. Electroanatomical mapping or superimposing of cardiac electrical activity on fluoroscopic image is provided by placing visual indicators on electrode pairs of various catheters including standard catheters and ablation catheter. Visual indicators are coupled or linked to underlying electric signals from those electrode pairs via software coding, whereby electrical activity sequence of the heart is provided and updated in real-time on fluoroscopic image.

In one aspect of this disclosure, the fluoroscopic image may be combined with or overlayed or superimposed with detailed image such as a CT scan or MRI or with ultrasound.

In another aspect of this disclosure, the fluoroscopic image may be substituted for a heart model.

In another aspect of this disclosure, the electroanatomical system may be combined with signal mapping wherein signal mapping comprises automation features and clinical decision support features useful for cardiac mapping and ablation of arrhythmias.

In another aspect of this disclosure, the visual indicators may be light emitting diodes (LEDs) which blink based on sensing electrical activity.

In another aspect of this disclosure, the visual indicators may utilize color coding instead of placing LEDs on structures.

In another aspect of this disclosure, the method and system of the current disclosure may be used for ablation of cardiac arrhythmias which are supraventricular or ventricular in origin.

In another aspect of this disclosure, the mapping system may be used for ablation of atrial flutter, atrial tachycardia, AVNRT, AVRT, ventricular tachycardia, RVOT, LVOT, or atrial fibrillation.

In another aspect of this disclosure, the electoantomical mapping system feature can be combined with various other features of electrophysiological mapping including timing mapping, automation feature, and clinical decision support features as mentioned below.

In another aspect of this disclosure, these novel tools and features can be incorporated and run via a tablet such as the I-Pad.

In another aspect of this disclosure, these novel tools and features can be incorporated and run via a mobile device.

In one embodiment, the method and system provides guidance for ablation in the zone of slow conduction/vulnerable portion of the circuit for atrial flutter ablations.

In one embodiment, the method and system provides visual guidance as to when the ablation catheter is in the zone of slow conduction.

In one embodiment, the method and system provides visual guidance as to when the ablation catheter is not in the zone of slow conduction.

In one embodiment, the method and system provides visual guidance as to when the ablation catheter is not in the zone of slow of conduction, but is close to it.

In one embodiment, the method and system provides visual guidance (displayed numbers) based on entrainment as to when the ablation catheter is in the flutter circuit.

In one embodiment, in the method and system the software is configured and programmed as to automatically display the entrainment mapping numbers when the pacing from ablation catheter is stopped.

In one embodiment, in the method and system the software is configured and programmed as to automatically display the numbers for checking for the line of block, post ablation.

In one embodiment, in the method and system the software is configured and programmed as to automatically display the numbers for checking for the line of block, post ablation with CS pacing.

In one embodiment, in the method and system the software is configured and programmed to automatically display the timing numbers for checking for the line of block, post atrial flutter ablation with pacing from the ablation catheter.

In one aspect of the disclosure, voice activated commands are given to activate various features of the disclosure.

In one aspect of the disclosure, voice activated commands are given to activate a sequence for measuring line of block with CS pacing.

In one aspect of the disclosure, voice activated commands are given to activate a sequence for measuring line of block with pacing from the ablation catheter and measuring the time to the CS catheter signal.

In one aspect of the disclosure, voice activated commands are given to activate a sequence for measuring other automated measurements.

In another aspect of the disclosure, the system performs timing analysis of atrial and ventricular intracardiac signals using software selected from a group comprising, Lab Windows/CVI, LabView (National Instruments Corp.), Microsoft Visual C++, Dot Net framework, MATLAB, Microsoft Visual Basic.

In another aspect of the disclosure, the software program for analyzing intracardiac timing relationships can be modified.

In one embodiment, in the method and system of this disclosure the software is configured and programmed as to automatically display the earliest activation information in real-time.

In one embodiment, in the method and system of this disclosure the software is configured and programmed as to automatically display the earliest activation information in real-time, along with earliest activation for the session.

In another aspect of the disclosure, the system contains means for EKG localization.

In another aspect of the disclosure, the system contains software which is programmed and configured for EKG localization either automatically or interactively with the physician or operator answering questions.

In another aspect of the disclosure, the software is programmed and configured such that the system measures the polarity of QRS complexes and determines automatically whether the polarity is positive, negative, or flat and stores that information in a table, which is used by the system for determining the localization or regionalization of the arrhythmia.

In another aspect of the disclosure, the system uses electrogram polarity information and one or more of area under the curve, width of the QRS complex, or amplitude of the signal.

In another aspect of the disclosure, 12-lead EKG localization is used for Atrial tachycardia, Ischemic ventricular tachycardia, Idiopathic ventricular tachycardia including RVOT and LVOT, accessory pathways including WPW, PVC mapping, and other focal or re-entry tachycardia's.

In another aspect of the disclosure, 12-lead EKG localization may be interactive with the physician or operator answering questions interactively and determining the localization information with the program.

In one embodiment, the physician or operator answers questions about the arrhythmia's based on the 12-lead morphology and the program displays the answer such as the site of localization.

In one embodiment, the physician or operator answers questions about the arrhythmia's based on the 12-lead morphology and the program display the answer such as the site of localization in graphical form such as a picture marked with localization.

Various other features, objects and advantages of the disclosure will be made apparent from the following description taken together with the drawings.

BRIEF DESCRIPTION OF THE DRAWINGS

For the purpose of illustrating this disclosure, there are shown in accompanying drawing forms which are presently preferred, it being understood that the disclosure is not intended to be limited to the precise arrangement and instrumentalities shown.

FIG. 2B depicts flashing of the LED corresponding to the HRA location.

FIG. 5A depicts placement of catheters and corresponding LEDs for mapping atrial flutter.

FIG. 6C shows blinking of CS catheter LED in counter-clockwise sequence of activation.

FIG. 8B depicts application of the DVRT mapping system in focal atrial tachycardia, with the REF catheter LED blinking.

FIG. 14 depicts schematically the positioning of the ablation catheter for ablating typical atrial flutter, where the site of ablation is not desirable.

FIG. 28 shows schematically the screen for template matching for 12 leads (I, II, III, aVR, aVL, aVF, V1, V2, V3, V4, V5, and V6) and for pace mapping, where the corresponding signals are displayed adjacent to each other.

FIG. 29 shows schematically the screen for template matching for 12 leads (I, II, III, aVR, aVL, aVF, V1, V2, V3, V4, V5, and V6) and for pace mapping, where the corresponding signals are superimposed on each other.

FIG. 35 shows the question answering screen of the Ischemic VT localization program.

FIG. 41 shows a menu screen for the EKG localization program.

DETAILED DESCRIPTION OF THE DISCLOSURE

The following description is of the best mode presently contemplated for carrying out the disclosure. This description is not to be taken in a limiting sense, but is made merely for the purpose of describing the general principles of the disclosure. The scope of the disclosure should be determined with reference to the claims.

In the cardiac electrophysiology art, electroanatomical mapping generally refers to superimposing of the electrical activity on an image or computer model of the heart. Patient's electrical timing information is generally color coded on a computer model. Prior art electroanatomical systems (Biosense Websters's Carto™ system and St Jude Medical's Navix™ system), generally collect information point by point, with the physician manipulating the mapping catheter within a chamber of the heart. The points are then captured on the computer by an operator. Each point contains location or geometry information as well as electrical timing information relative to a reference catheter. As the points are collected, a shell of chamber geometry is constructed utilizing proprietary algorithms and the electrical information is color coded and superimposed on the geometry. For Navix™ the geometry information is impedance based, and for Carto™ the geometry information is electromagnetically based. These indirect methods require a lot of geometry points to build an accurate geometry. Theoretically, an infinite number of points would reconstruct a totally accurate image of the chamber.

Figure 1A:
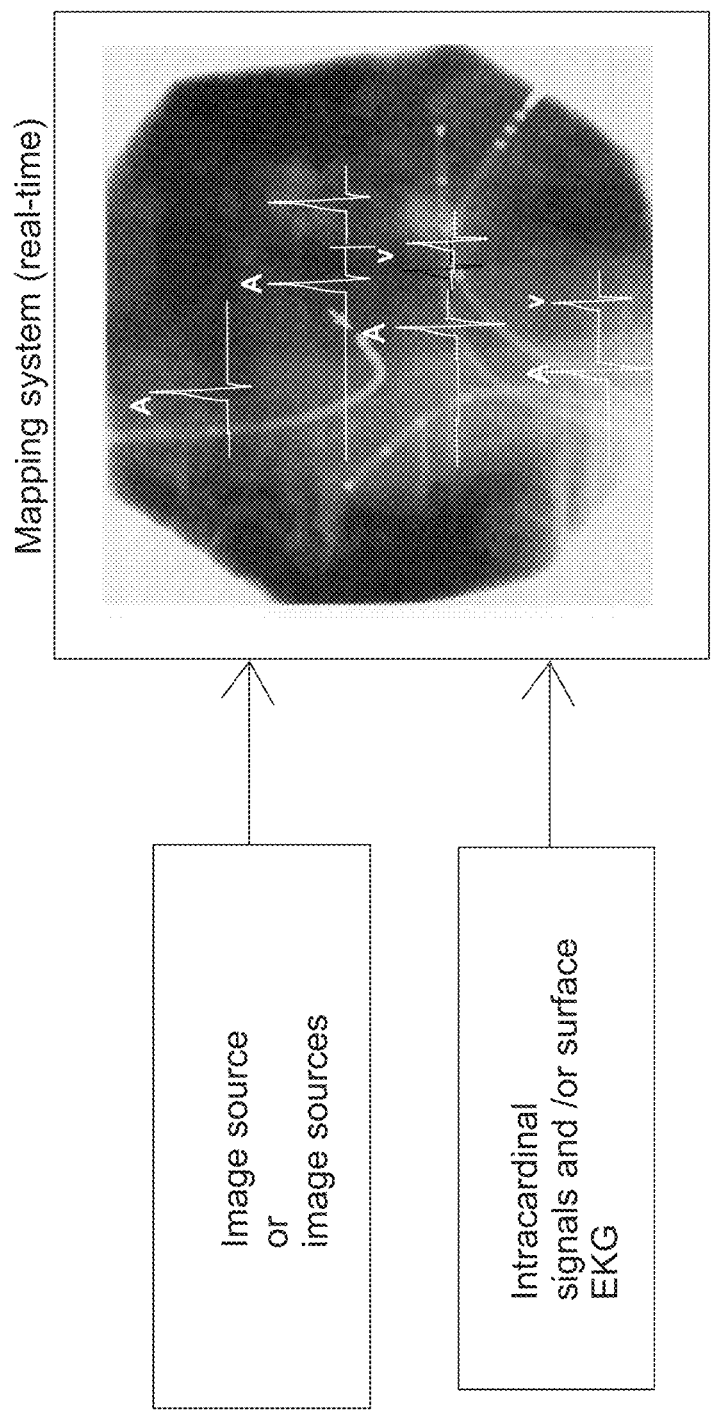
FIG. 1A depicts the concept of electroanatomic mapping.

The system and method of the current disclosure bypasses the indirect method of geometry reconstruction. In the current disclosure, as shown in conjunction with FIG. 1A an image, such as patient's fluoroscopy image and patient's intracardiac signals are coupled by the method of this disclosure and provide a direct visual real-time mapping information (DVRT)

For the description of the concept and its application to various arrhythmia's, it's instructive to cover normal sinus rhythm (NSR) as an aid to understanding the concept of the current direct visual, real-time (DVRT) mapping system. In the method and system of the DVRT mapping concept, the fluoroscopy image is brought into the DVRT mapping system. Other imaging technology or a combination of imaging technology may also be brought into the system. Generally, four diagnostic catheters are placed in the heart during EP studies and ablation procedures, these are:
1) HRA catheter
2) HIS catheter
3) CS catheter, and
4) RV catheter.

The four standard catheters are strategically placed and provide information from different regions of the heart. The HRA catheter provides information from the high right atrium. The HIS catheter provides information from the AV node. The CS catheter provides information from the low right atrium and left atrium. The RV catheter provides information from the right ventricle.

In this disclosure, the terms ablation catheter (ABL catheter), mapping catheter, roving catheter are all referring to the ablation catheter and are used interchangeably. Ablation or mapping catheters are generally steerable catheters and comprise a deflectable distal end which is generally deflected from the handle of the catheter. The terms leads and catheters are also used interchangeably.

Figure 1B:
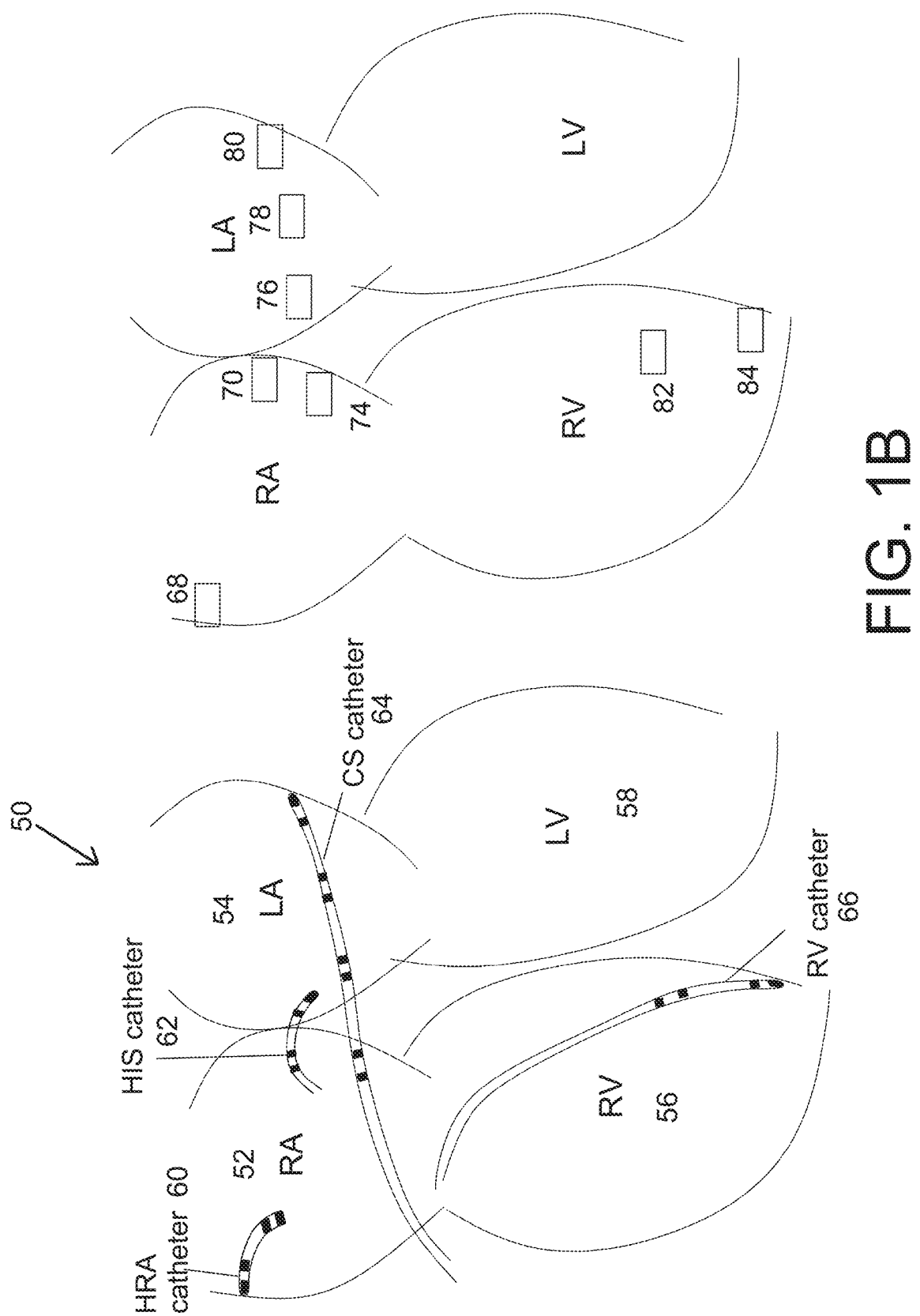
FIG. 1B depicts four catheters in the heart, and placement of LEDs (light emitting diodes) at the corresponding electrode pairs.

In the method and system of this disclosure, and as is shown in conjunction with FIG. 1B, the software is configured and programmed such that with the acquired image shown in FIG. 1B (the fluoroscopic image), an LED (light emitting diode) is placed on any or all electrode pair(s) of catheter(s) placed in a patient's heart. This is shown in the right side of the figure. Further the LEDs are configured and programmed utilizing proprietary software to link to the underlying corresponding electrical signal(s) of that particular electrode pair. Therefore when an electrical impulse of the heart passes by that electrode, a visual indicator such as the LED is activated. As shown in FIG. 1B, an LED 68 is placed on the distal electrode pair of the HRA catheter 60, utilizing a mouse or touch screen means. This LED 68 is configured and programmed to blink or linked to the wave of depolarization in the cardiac tissue (underlying signal) of HRA catheter 60 and when it crosses a threshold detection level. At that point the LED lights up momentarily.

Similarly as shown, an LED 70 is placed on the distal or proximal pair of the HIS catheter 62. Similarly this LED 70 is configured and programmed by the software (i.e. linked by the software) to light up as the HIS catheter 62 signal goes above a threshold detection level. Similarly, LED's 74, 76, 78, and 80 are placed on the 4 electrode pairs of octa-polar electrodes of the CS catheter 64. These are configured and programmed by the software to blink, or flash as the corresponding signals of the CS catheter electrode 64 reaches a threshold value. The fourth lead in FIG. 1B is the right ventricular RV lead 66. An LED 82 is placed on the proximal pair and LED 84 is placed on the distal pair of the RV catheter 66. The two RV LED's 82 and 84 are configured and programmed with software to blink as their corresponding RV signals (distal and proximal) cross a threshold detection level under the corresponding electrode pair, or when the heart's electrical pulse reaches the ventricle.

Figure 2A:
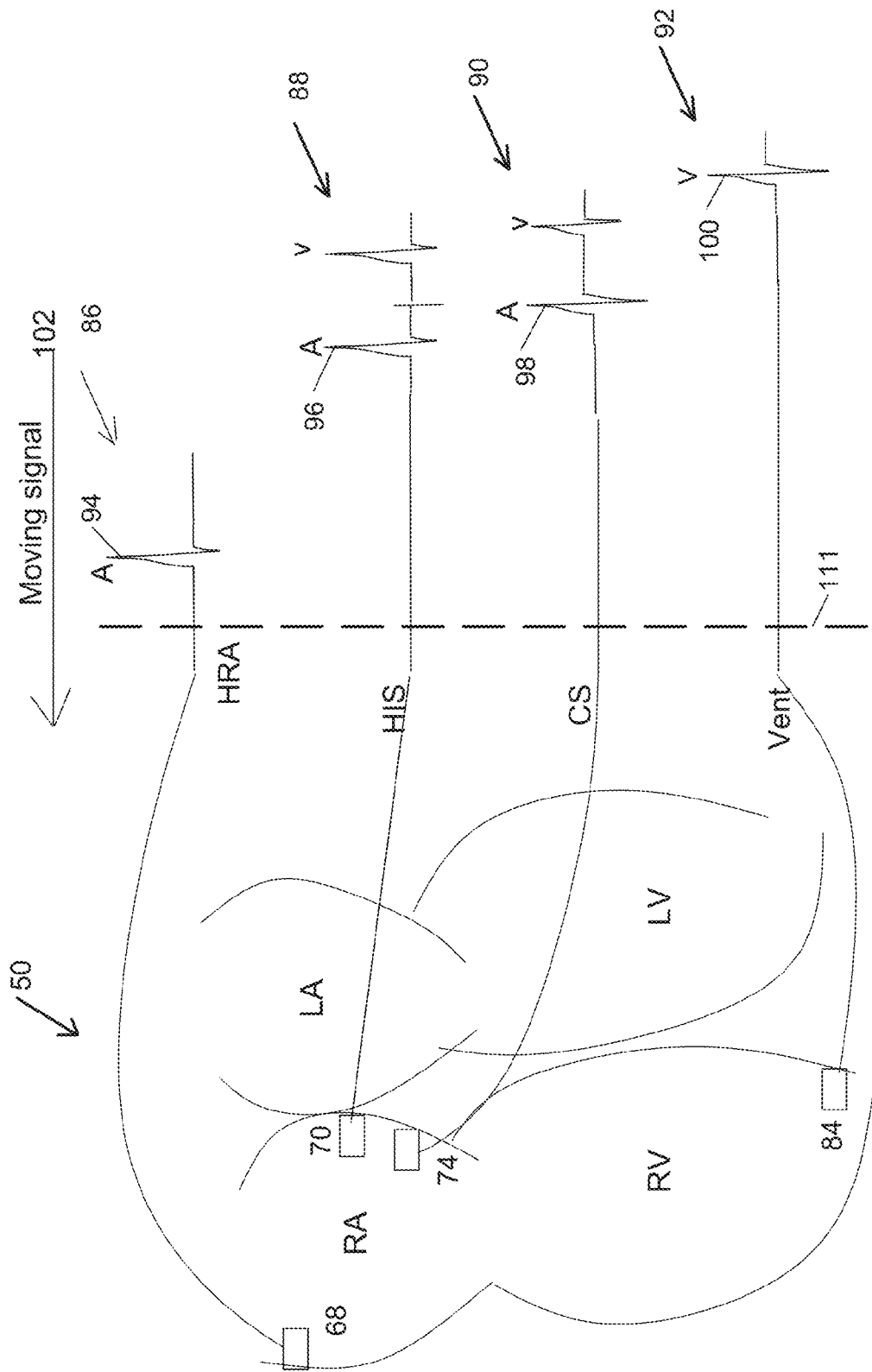
FIG. 2A depicts LEDs placed on the electrode pairs and the corresponding recordings of signals from those electrode pairs of catheters.
Figure 2C:
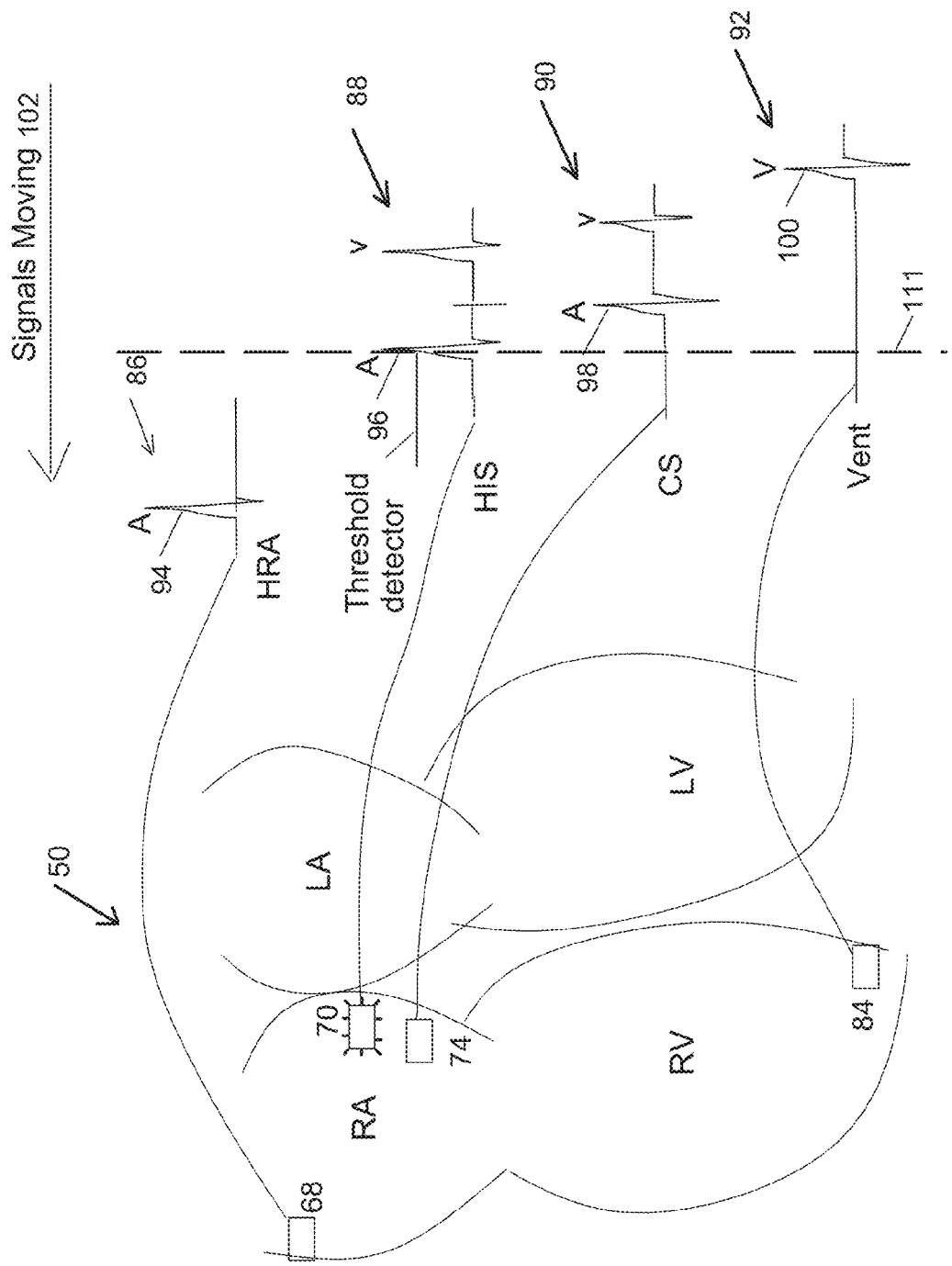
FIG. 2C depicts flashing of the LED corresponding to the HIS location.
Figure 2D:
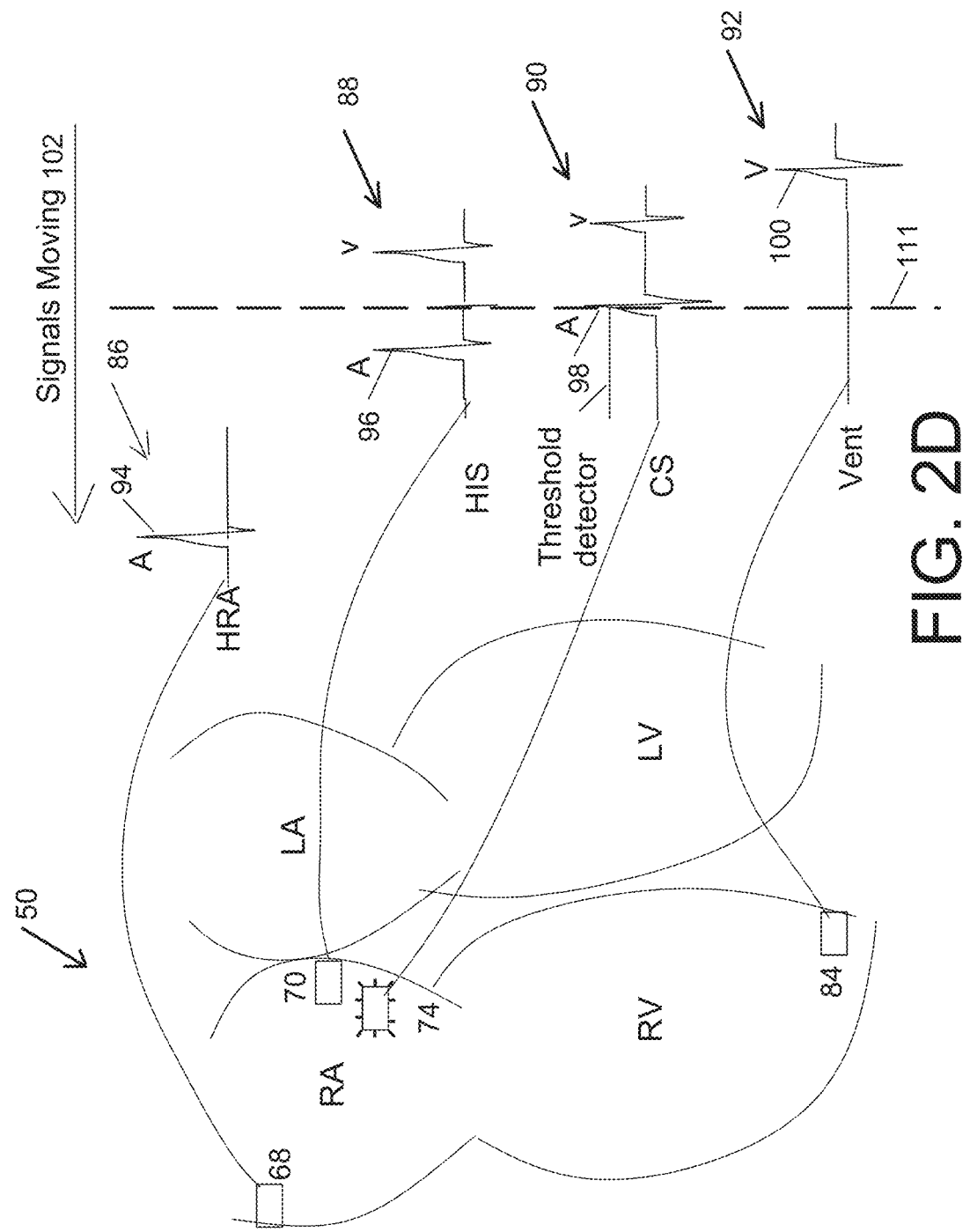
FIG. 2D depicts flashing of the LED corresponding to the CS location.
Figure 2E:
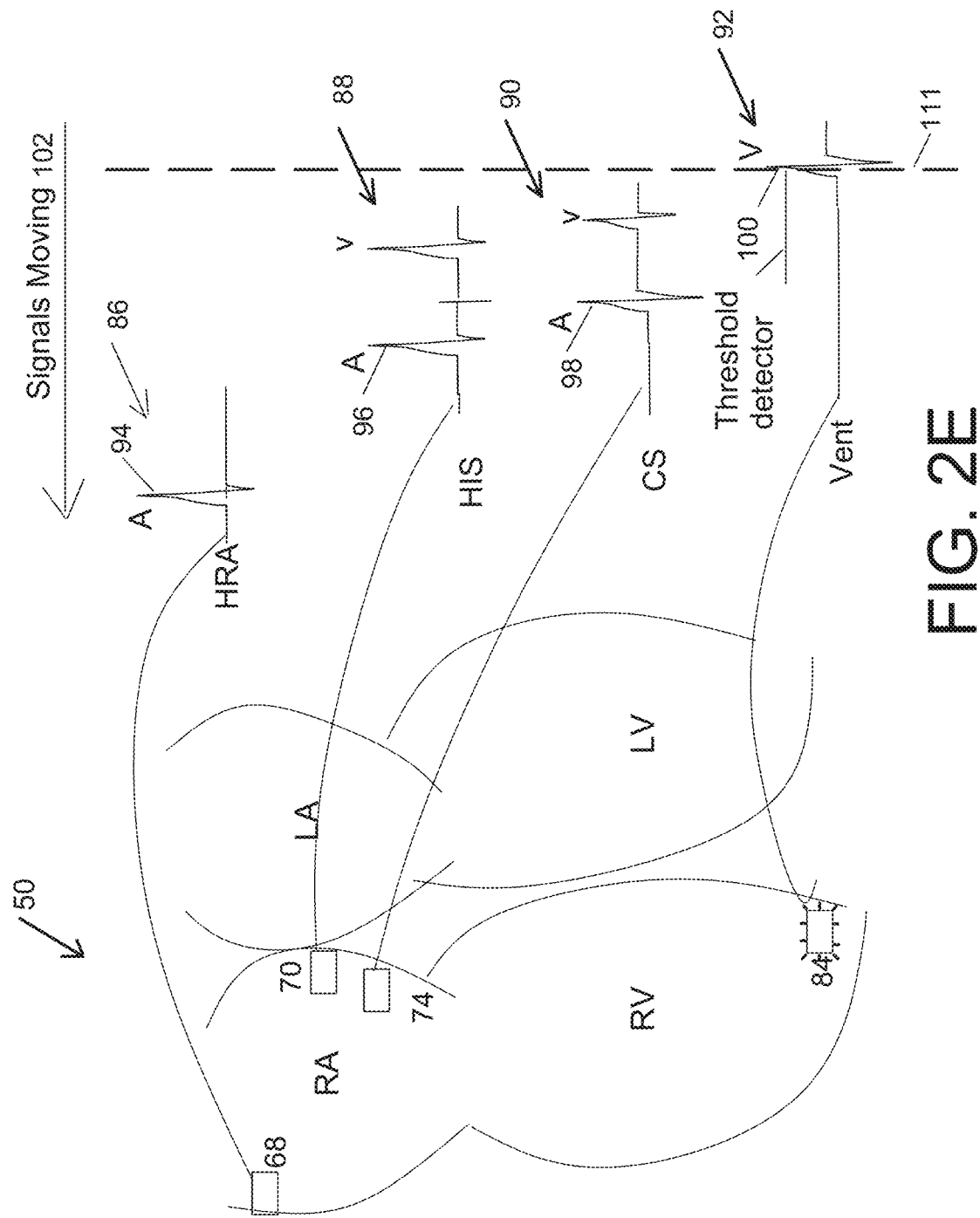
FIG. 2E depicts flashing of the LED corresponding to the RV location.

As is shown in FIG. 2A, signals from HRA catheter 60, HIS catheter 62, CS catheter 64, and RV catheter 66 are also displayed on the screen. These signals are, repetitious, dynamic and are moving (in this case towards the left). On the relative timing scale an arbitrary line 111 is drawn. In normal sinus rhythm (NSR), the atrial (A) signal in HRA catheter 60 comes first temporally or crosses the arbitrary line 111 first. As shown in FIG. 2B, as the signals from all the channels are moving towards the left, the atrial signal 94 from HRA catheter comes first. As the atrial signal crosses the threshold detection level, the LED 68 placed on the distal HRA lead 60 pair temporarily lights up (or blinks or flashes). After a few milliseconds, the atrial signal 98 of the HIS lead crosses the threshold detection levels and the HIS catheter LED 70 blinks (shown in FIG. 2C). A few milliseconds later, the atrial signal from the CS lead crosses the threshold detection level and the corresponding LED 74 blinks (shown in FIG. 2D). Next in sequence, the ventricular (V) signal 100 from the RV lead crosses the threshold detector, and the corresponding RV catheter. LED 84 flashes, or temporally lights up (shown in FIG. 2E).

Figure 3:
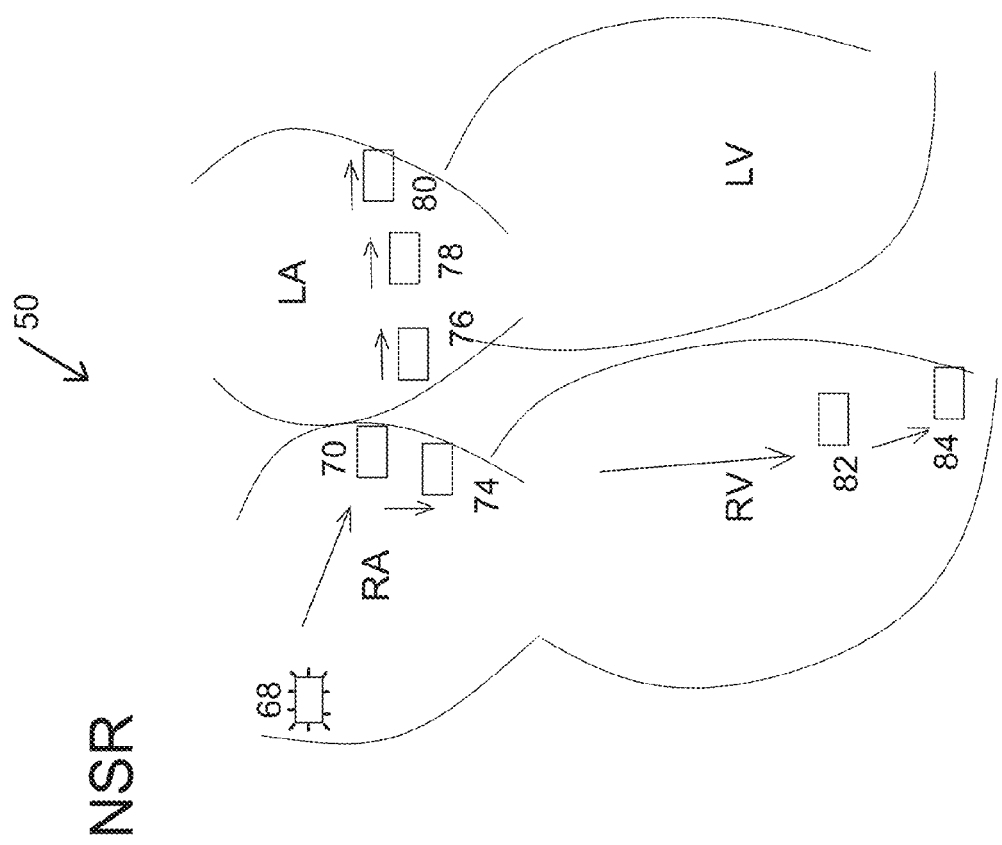
FIG. 3 depicts flashing of the LEDs in normal sinus rhythm (NSR), where the sequence of activation is high to low, and right to left.

This methodology for normal sinus (NSR) is summarized in conjunction with FIG. 3. The LEDs are placed on the 3-D image of the heart. This may be preferably a fluoroscopic image of the heart, but can be a detailed image such as CT scan, MRI, or even a model of the heart. In one embodiment, it can be an overlay of any two images, such as by way of example an overlay of a fluoroscopic and a CT or MRI overlaid on top of it. Superimposed on this structural image is the real-time electrical activity of the heart. The LED's blinking in sequence corresponding to the electrical activity at that anatomic location in that patient. Therefore as shown in conjunction with FIG. 3, the DVRT mapping system clearly shows the blinking sequence of LEDs which are placed on a 3-D structure, or shows real-time propagation. This real-time propagation map shows that the activation sequence in NSR is generally from high to low and right to left. The software is also configured such that a delay can be added to the blinking of the LED's such that the sequence of blinking may be relatively fast or relatively slow. Adding a delay in blinking will not change the sequence of activation. The blinking sequence cycle then repeats itself approximately 70 times a minute.

Generally, the currently available mapping systems show the propagation only in a review mode. The technology of this disclosure is distinct in that after the catheters are positioned in the heart, and the LED's are positioned on the catheter electrodes, propagation of the electrical activity is presented in real-time. Advantageously, this makes the ablation procedure workflow proceed at a much faster pace.

The concept of this mapping system can be applied to any and all arrhythmias including but not limited to mapping sinus tachycardia, atrial flutter, atrial fibrillation, focal atrial tachycardia (AT), focal ventricular tachycardia, re-entry ventricular tachycardia, RVOT, LVOT, AVNRT, accessory pathway mediated tachycardia. The method and system of this disclosure is useful for both re-entry tachycardias, as well as, focal tachycardias.

Application to Atrial Flutter

Figure 4:
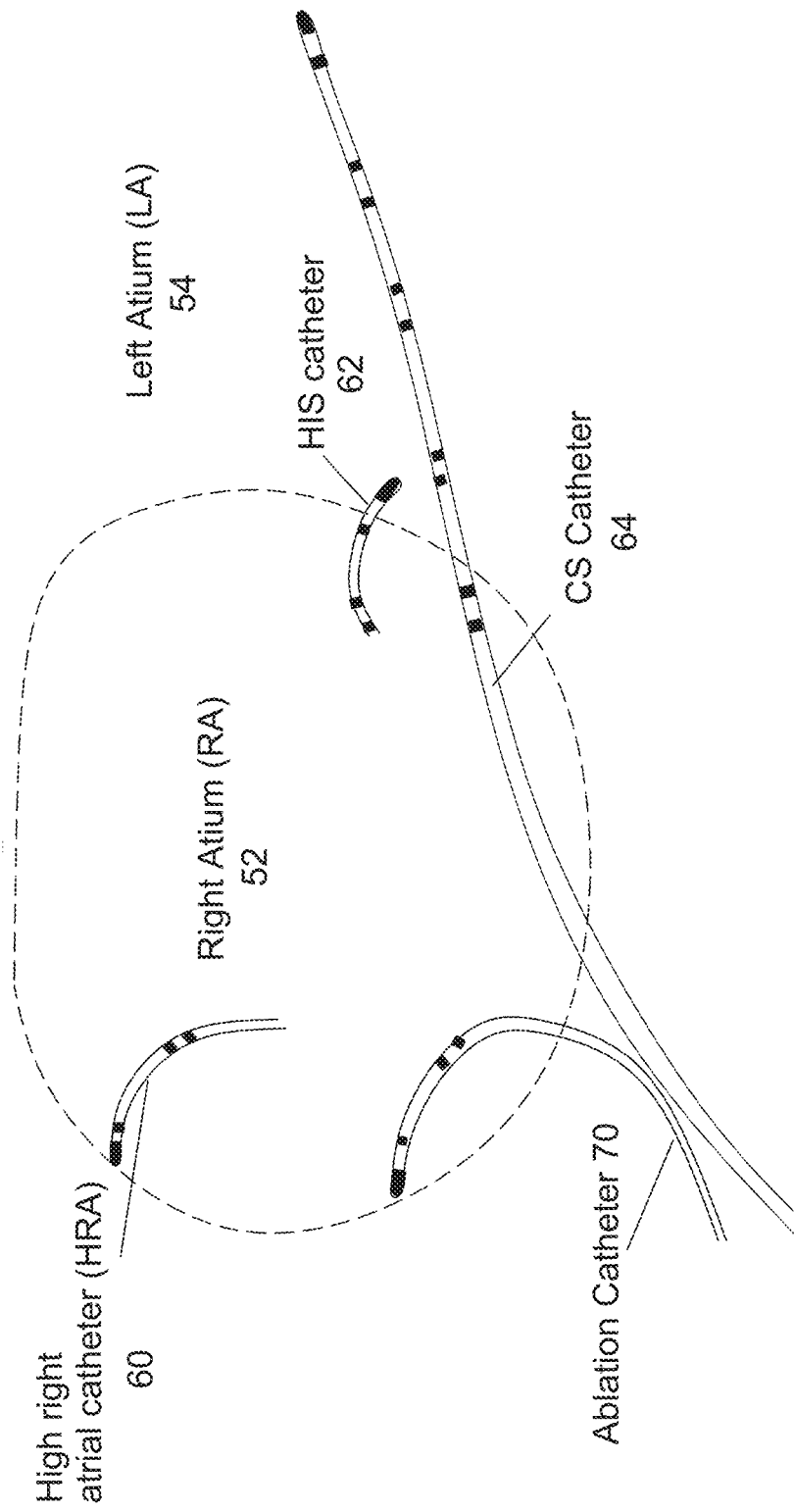
FIG. 4 depicts placement of HRA, HIS, CS, and ABL catheter for use in atrial flutter mapping.

Shown in conjunction with FIG. 4 is the placement of the HRA catheter 60, HIS catheter 62, CS catheter 64 are as before. Additionally in the case of atrial flutter the ablation (or mapping or roving) catheter is placed in the low lateral position of the atrium and the LED's are positioned on the electrodes of these. Catheter and LED placement is as is shown in conjunction with FIG. 5A. Because of the strategic placement of these catheters and hence the LEDs, as the activation sequence progresses, it is easy to visualize the atrial flutter propagation as clockwise or counter-clockwise activation sequence, as is generally common in "typical" atrial flutter. Typical flutters are generally cavo-cuspid isthmus dependent.

Figure 5B:
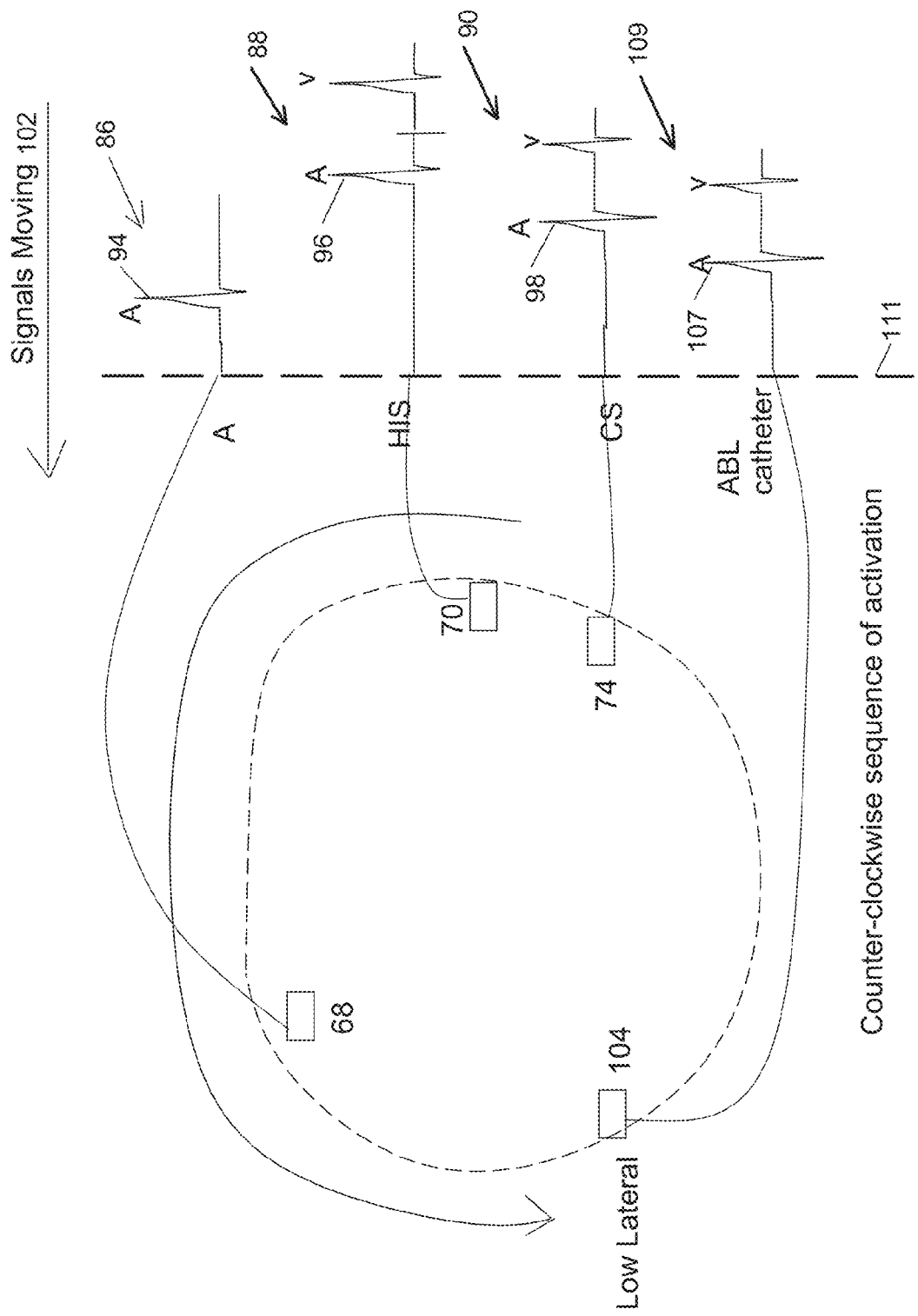
FIG. 5B shows timing of signals for corresponding LEDs in counter-clockwise flutter.

Shown in conjunction with FIG. 5B the atrial signal 94 from HRA lead is connected or "wired" to LED 68 which is in the high right atrium position. The atrial signal 96 from the His-bundle catheter 62 is connected or "wired" to LED 70, which is in the HIS position. The atrial signal 98 from the CS catheter 64 is connected or "wired" to the LED 74 which is in the CS position. The atrial signal 107 of the mapping or ablation catheter 71 is connected or "wired" to the LED 104 which is in the low lateral position of the atrium.

Figure 6A:
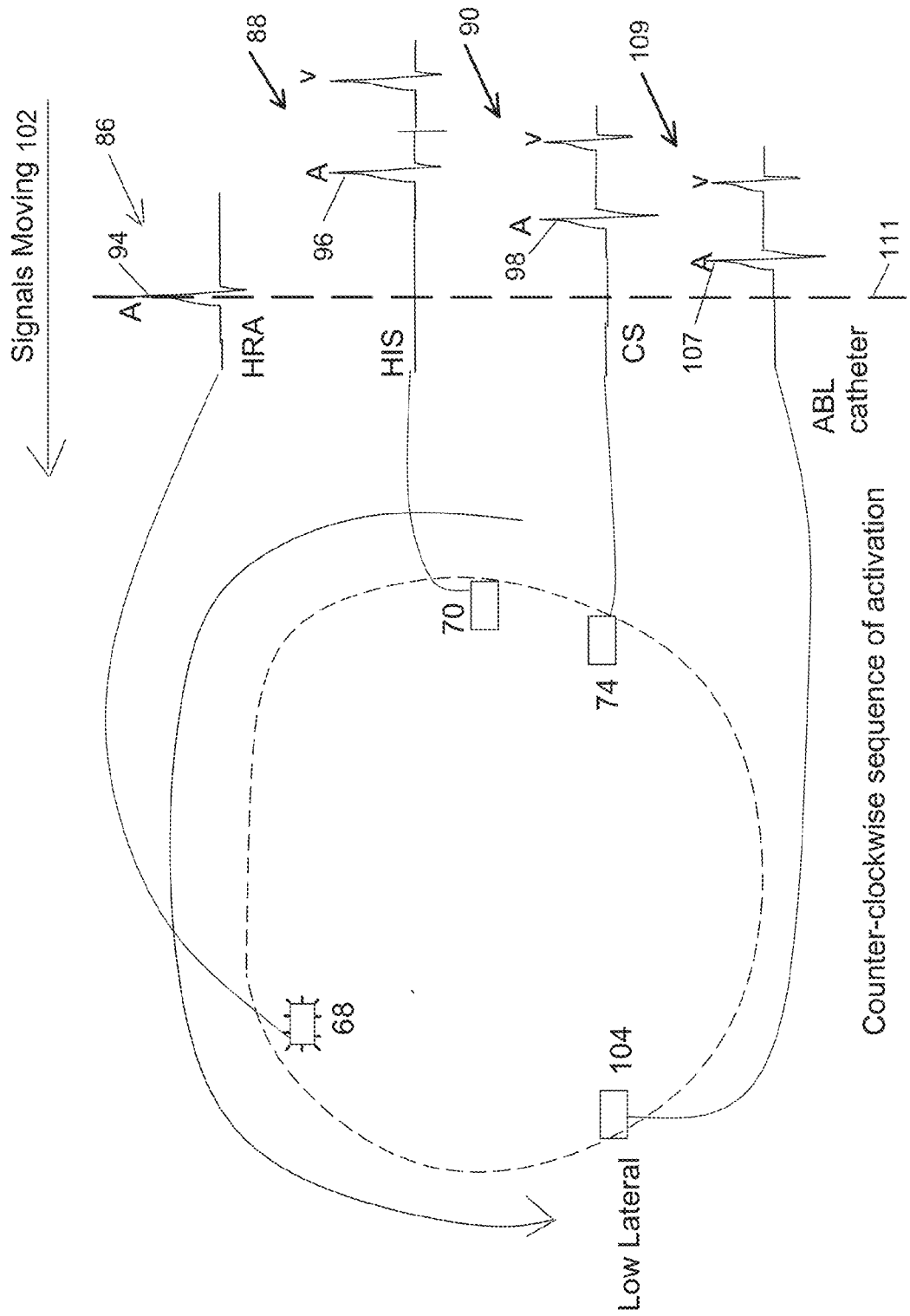
FIG. 6A shows blinking of HRA catheter LED in counter-clockwise sequence of activation.
Figure 6B:
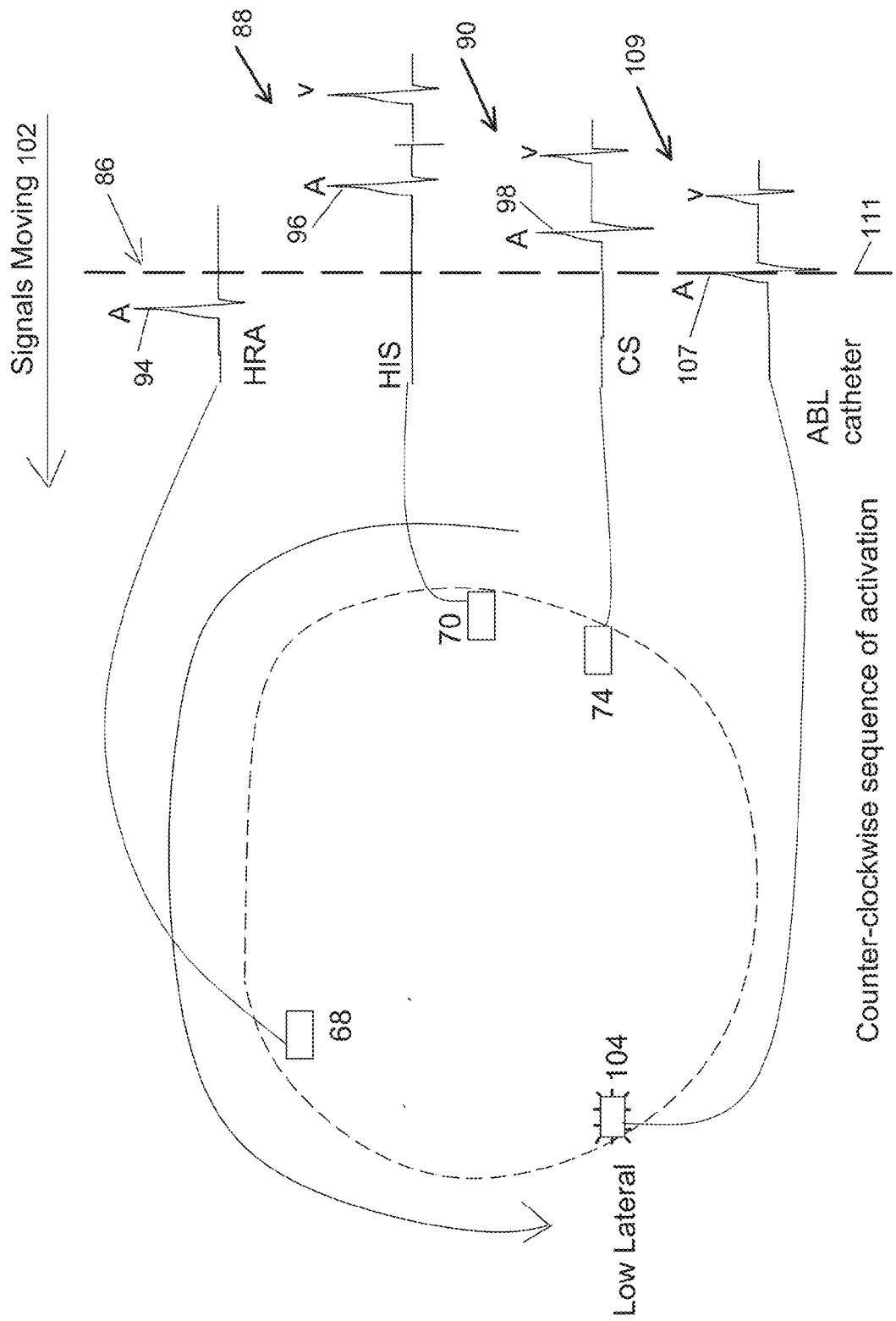
FIG. 6B shows blinking of ABL catheter LED placed at the low lateral position in counter-clockwise sequence of activation.
Figure 6D:
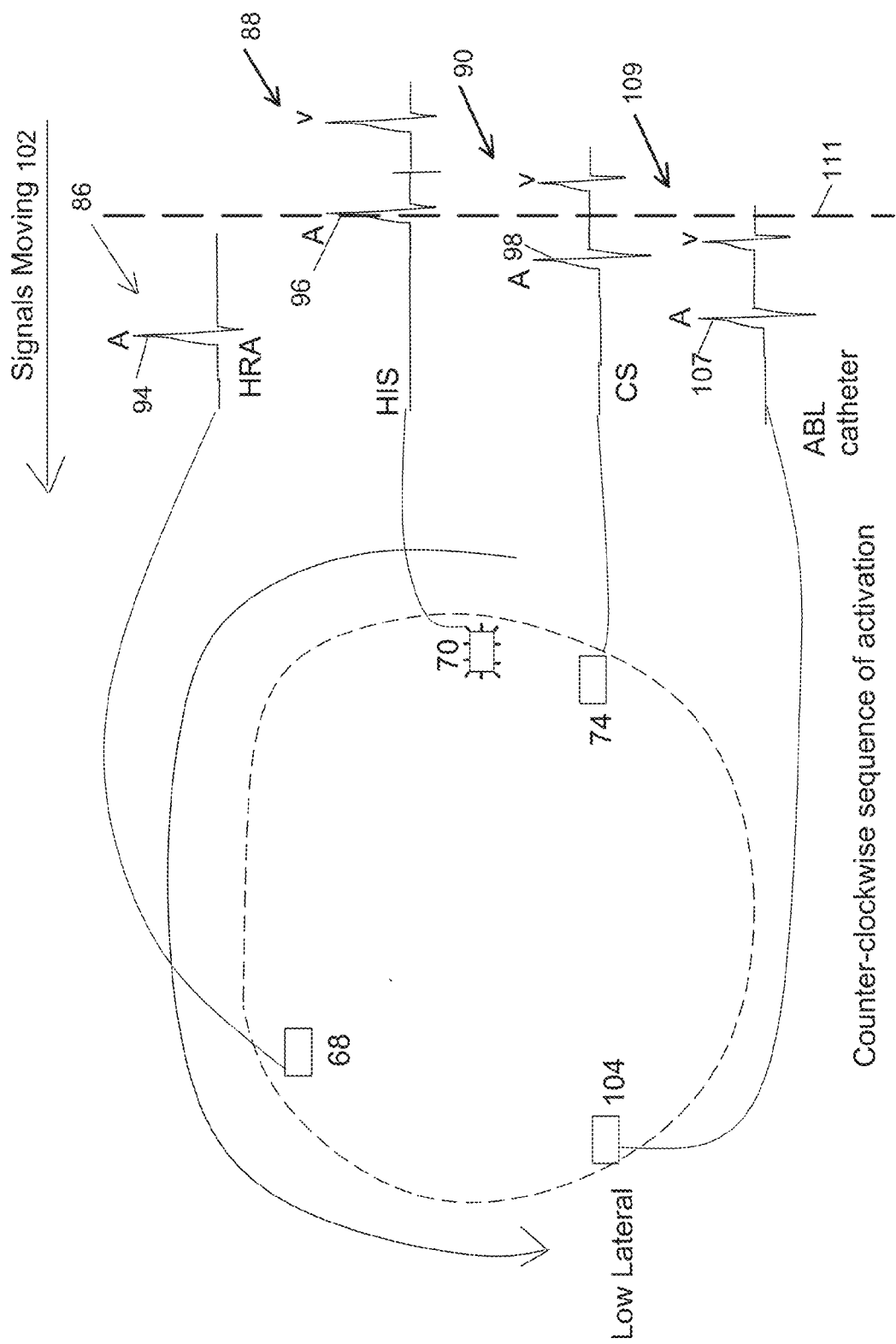
FIG. 6D shows blinking of HIS catheter LED in counter-clockwise sequence of activation.

Shown in conjunction with FIG. 6A, signals from the atrial catheter, His catheter, CS catheter, and ABL (mapping) catheter are displayed and are moving to the left. With each cycle, first the atrial signal 94 crosses the threshold detector and the LED 68 lights up. After a few milliseconds and next in sequence the atrial signal 107 from the mapping or ablation catheter crosses the threshold detector and the LED 104 in the low-lateral position light's up (shown in FIG. 6B). Shortly thereafter and next in sequence the atrial signal 98 from the CS catheter 64 crosses the threshold detector and LED 74 which is in the CS location light up. After a few milliseconds and next in sequence the atrial signal 96 crosses the threshold detector and the LED 70 in the HIS position lights up (shown in FIG. 6D).

This sequence of blinking in the counter-clockwise direction keeps on repeating itself. A typical cycle length of atrial flutter may be approximately 250 msec. In that case, the sequence of counter-clockwise blinking of LED's is repeated every 250 msec, or about four times every one second.

Figure 6E:
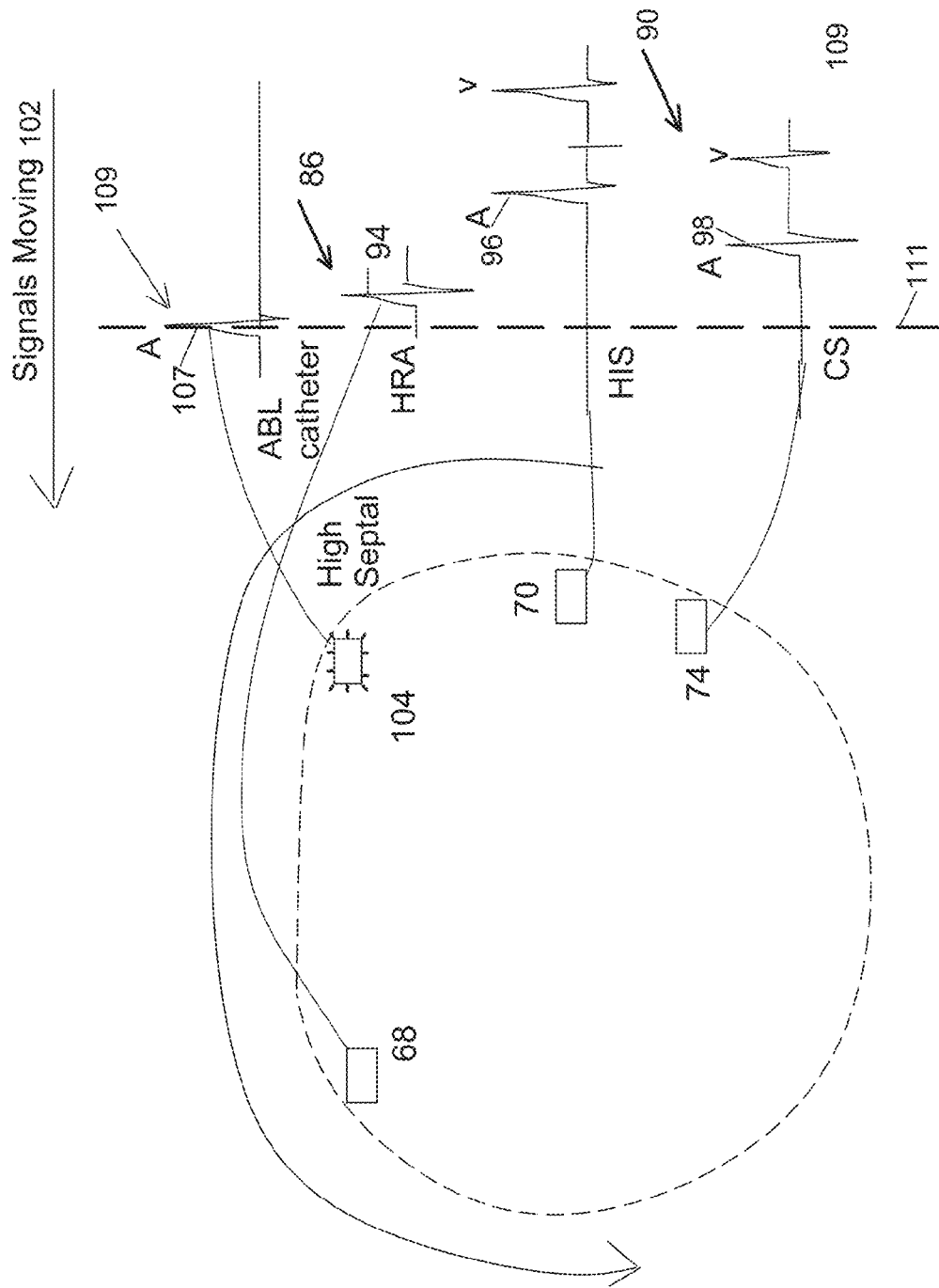
FIG. 6E shows blinking of ABL catheter LED placed at the high septal position in counter-clockwise sequence of activation.
Figure 6F:
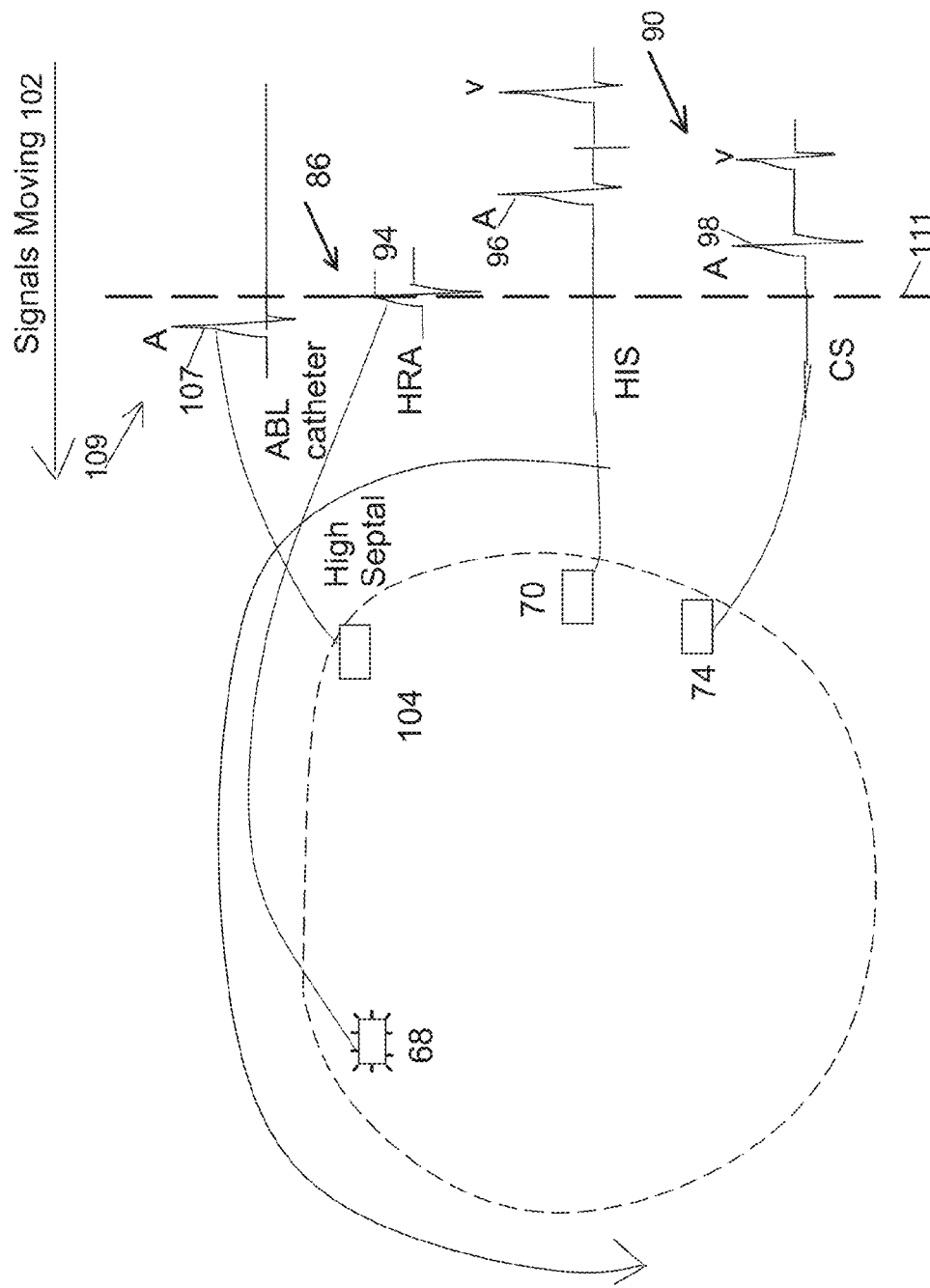
FIG. 6F shows blinking of HRA catheter LED with the ABL catheter placed at the high septal location in counter-clockwise sequence of activation.

Further, as shown in conjunction with FIG. 6E, the ablation or mapping catheter 70 may be placed in high septal position. Hence the LED of mapping catheter LED will be on the high septal position. In this case as shown in conjunction FIG. 6F, after high septal blinking, the next in sequence is the HRA catheter blinking. The rest will be as before.

Clockwise Flutter

Figure 7A:
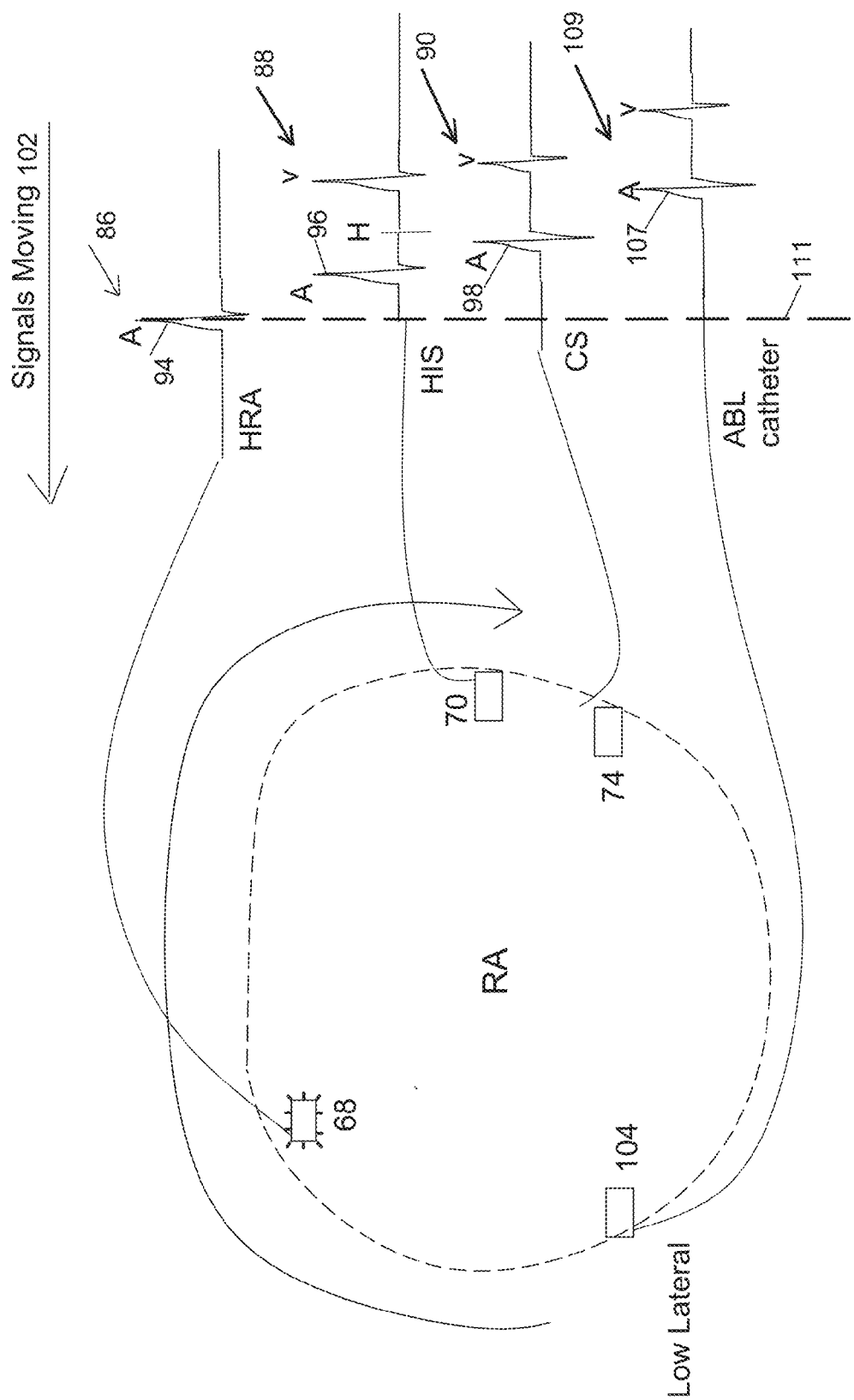
FIG. 7A shows blinking of HRA catheter LED in clockwise sequence of activation.
Figure 7B:
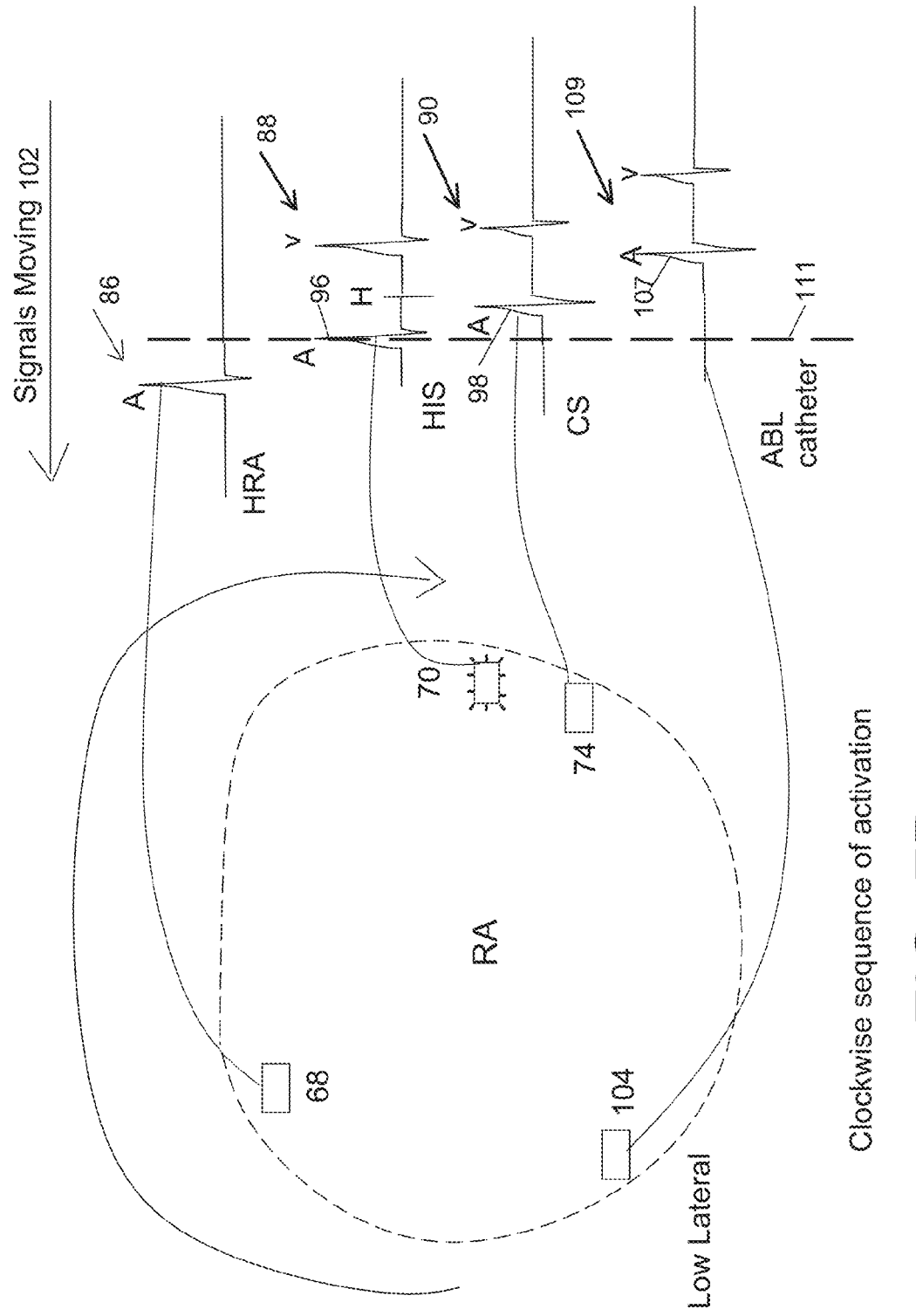
FIG. 7B shows blinking of HIS catheter LED in clockwise sequence of activation.
Figure 7C:
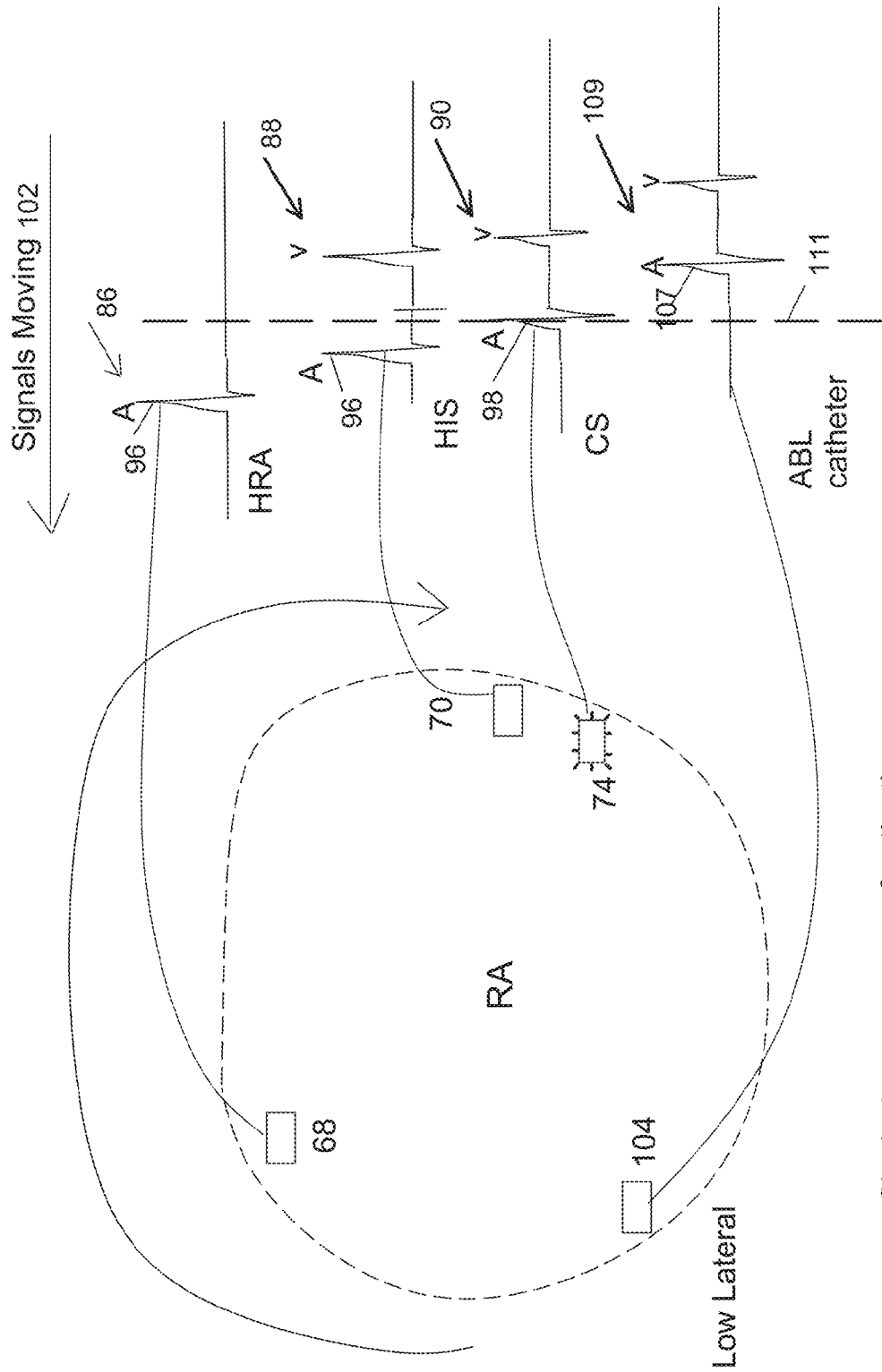
FIG. 7C shows blinking of CS catheter LED in clockwise sequence of activation.
Figure 7D:
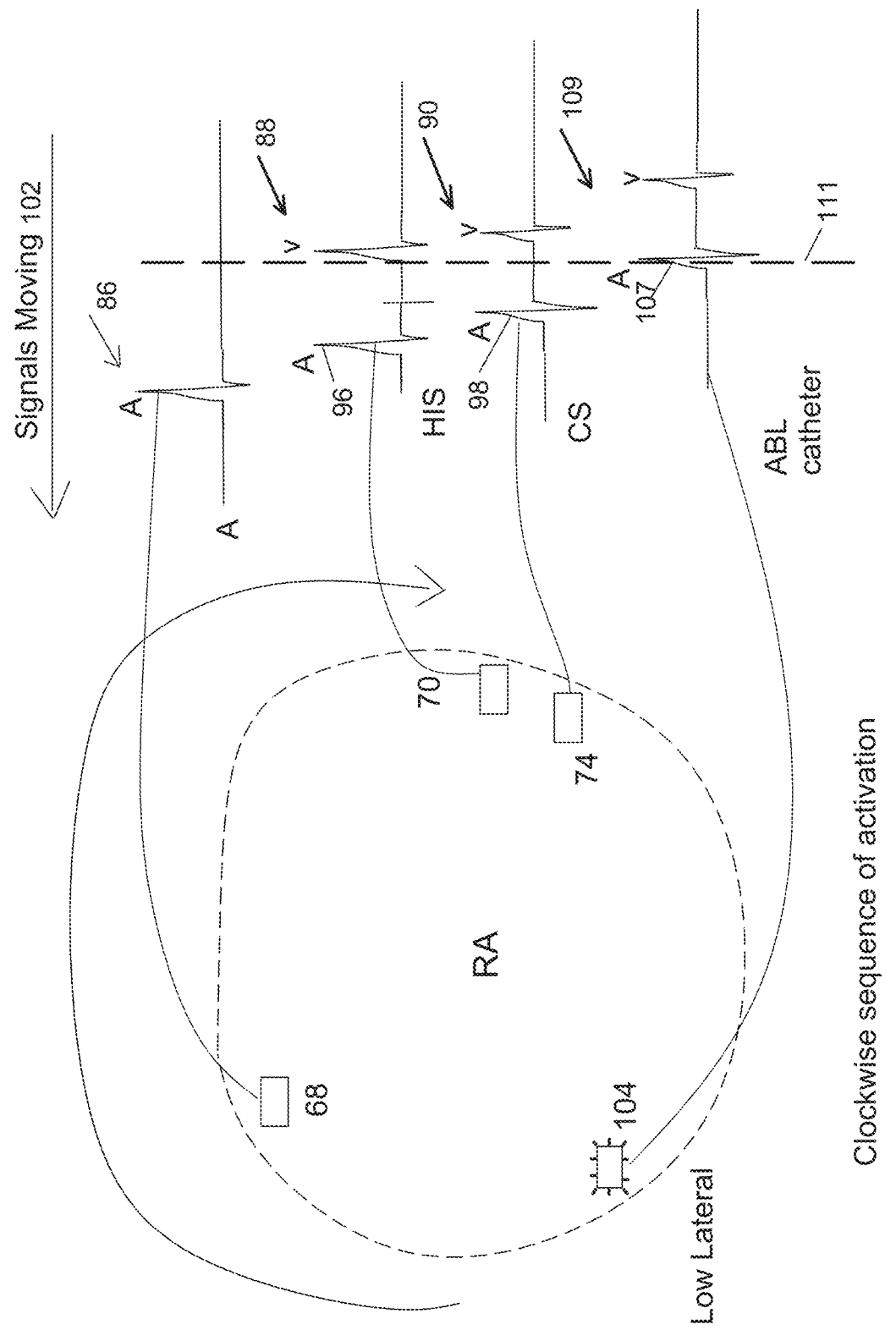
FIG. 7D shows blinking of ABL catheter LED in clockwise sequence of activation.

In the description below, an example is shown where the atrial flutter sequence is clockwise flutter, i.e., the sequence of activation in the atrium is in the clockwise direction. This is shown in conjunction with FIGS. 7A-7D. As shown in FIG. 7A, when the atrial signal 94 crosses the arbitrary line 111, the LED corresponding to HRA catheter temporarily lights up. After a few milliseconds, and next in sequence, shown in FIG. 7B, the atrial signal from the HIS catheter 96 crosses the arbitrary fixed line 111, and LED corresponding to the HIS catheter temporarily lights up. Next in sequence, shown in FIG. 7C, the atrial signal 98 from the CS catheter crosses the arbitrary line 111 and the LED corresponding to the proximal CS electrode pair light temporarily. Next in sequence, shown in FIG. 7D, the atrial signal 107 which corresponds to the ablation catheter in the low lateral position crosses the arbitrary line 111 and the corresponding LED 104 flashes.

As in the case of counter-clockwise flutter, this sequence repeats approximately every 250 milliseconds or about four times a second.

Application to Focal Atrial Tachycardia's (AT)

Generally in focal atrial tachycardia's an ectopic focus somewhere in the atrium takes over as the driver of atrial rhythm. The ectopic focus may be located anywhere within the right atrium or left atrium. The anatomic structure Crista Terminalis of the right atrium (RA) is one common location where focal ATs originate. In that case the focus may be anywhere on the Crista. Ectopic foci can originate from other areas of the right or left atrium also.

Figure 8A:
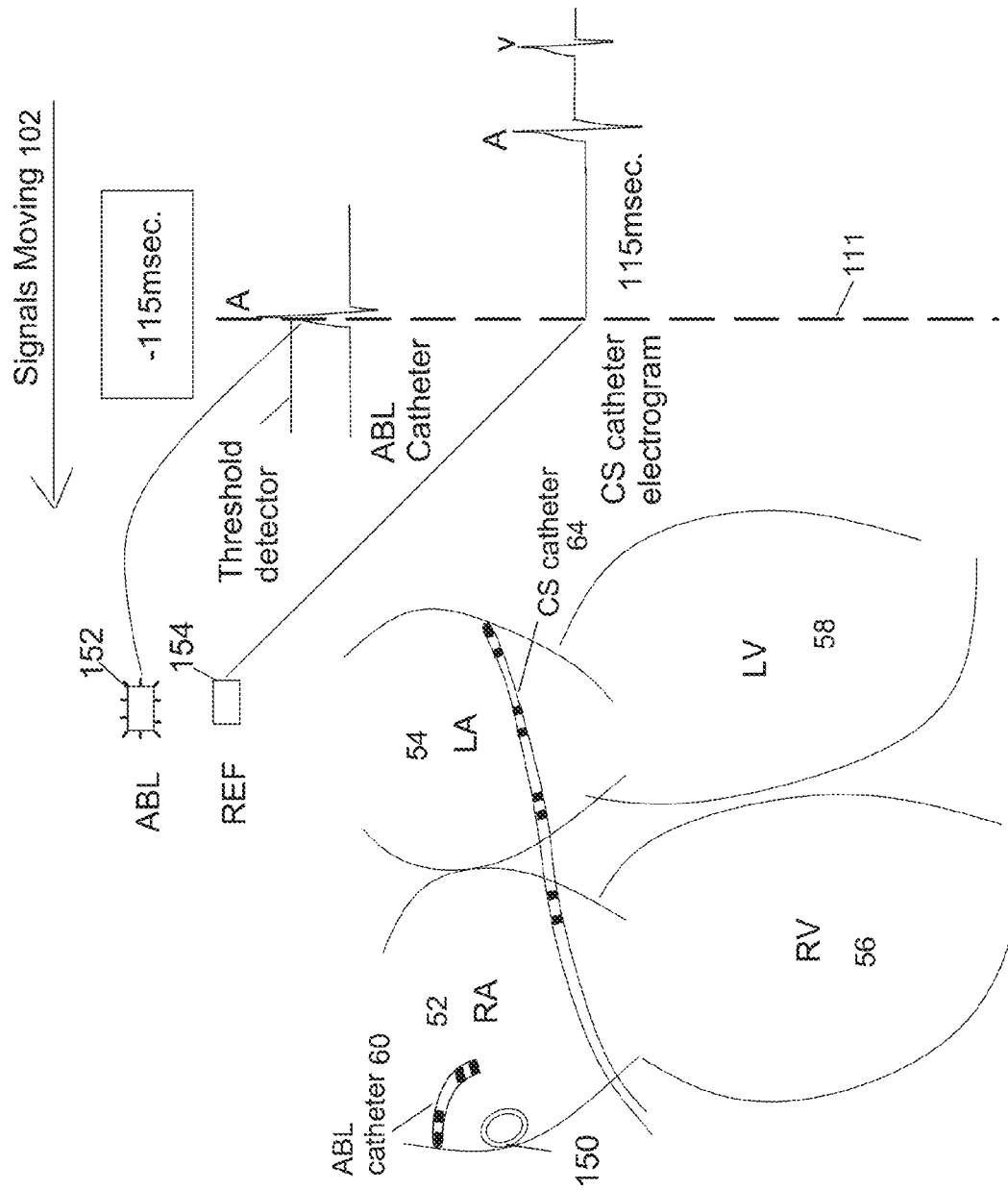
FIG. 8A depicts application of the DVRT mapping system in focal atrial tachycardia.

The mapping system of the current disclosure may be used for mapping the location of the ectopic focus. This is shown in conjunction with FIG. 8A. As depicted in FIG. 8A, in this case the ectopic focus 150 is located in the right atrium. In the method and system of this disclosure, a reference (REF) signal is selected by the physician or operator. The CS catheter is frequently used as a reference, because it is generally in a stable position, and doesn't move during the procedure. The HRA catheter can also be used as a reference, but is frequently not used unless it is in a stable position.

Using the timing of the reference signal as t=0, the relative timing of the mapping (or ABL) catheter signal is displayed both in actual numbers, and is displayed visually also. In one embodiment the visual display can be displayed via flashing LED. Other visual displays and indicators may also be used. Another example is color coding. In the method and system of this disclosure, both local activation timing (LAT) numbers and visual display are updated continuously and are in real-time in contrast to the presently available mapping system.

By way of example, shown in FIG. 8A the CS catheter electrogram is used as the reference. As shown in the figure, the location of the ablation catheter is such that ABL catheter signal appears 115 milliseconds (msec) earlier than the CS catheter signal. This is displayed as −115 milliseconds (msec) and the flashing of ABL light emitting diode (LED) 152 is 115 msec before the REF light emitting diode (LED) 154 flashing. Advantageously, both the flashing lights and timing numbers are updated continuously in real-time. As the catheter is manipulated in the atrium by the physician, the numeric timing and flashing is updated continuously in real-time. As will be clear to one skilled in the art, a time delay may be added to the flashing LEDs to make it more convenient for the operator to see which LED is flashing first. Generally, the key to successful ablation is to ablate at the earliest activation.

Figure 8C:
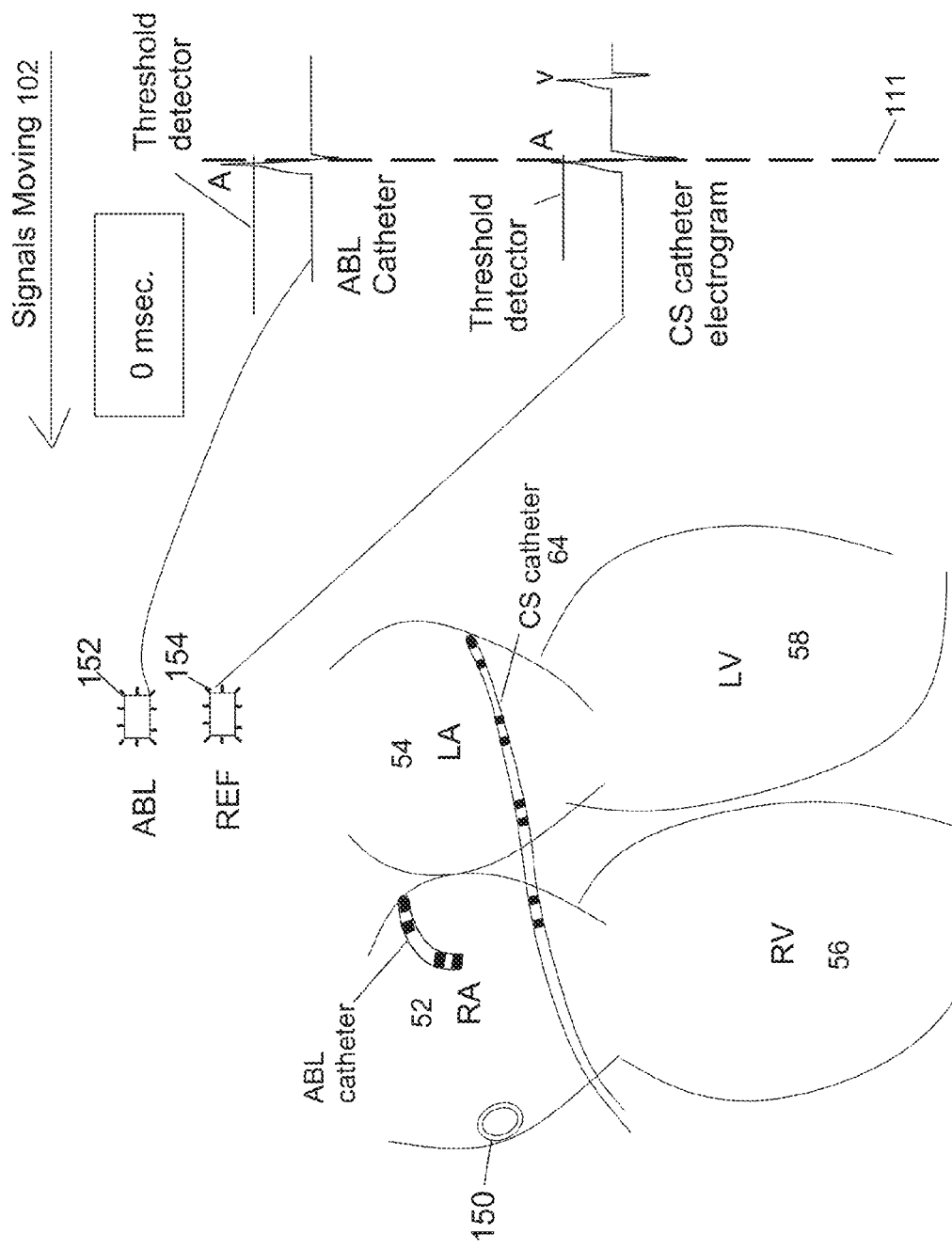
FIG. 8C depicts application of the DVRT mapping system in focal atrial tachycardia, with the ABL and REF catheter seeing the signal at the same time.

Shown in FIG. 8B is a depiction for example where the REF light emitting diode 154 flashes 115 msec after the ABL light emitting diode 154. As the ablation or mapping catheter 60 is manipulated, the timing relative to the REF signal keeps on changing depending on the location of the mapping or ablation catheter. The timing of the ablation catheter signal can be earlier (a negative number), the same as (zero), or later than (a positive number) the reference catheter signal. FIG. 8C depicts the scenario where the timing of the ablation catheter signal and REF catheter signal happens to be simultaneous. As shown in the figure, the timing number reads zero, implying that the ectopic focus signal takes equal amount to time to reach both the ABL catheter 60 and the CS catheter 64. Further, as depicted in FIG. 8C, the ABL or mapping light emitting diode 152 flashes simultaneously with the REF light emitting diode 154. The number zero is displayed and simultaneous flashing occurs as long as that position of the ABL catheter is maintained.

Figure 9A:
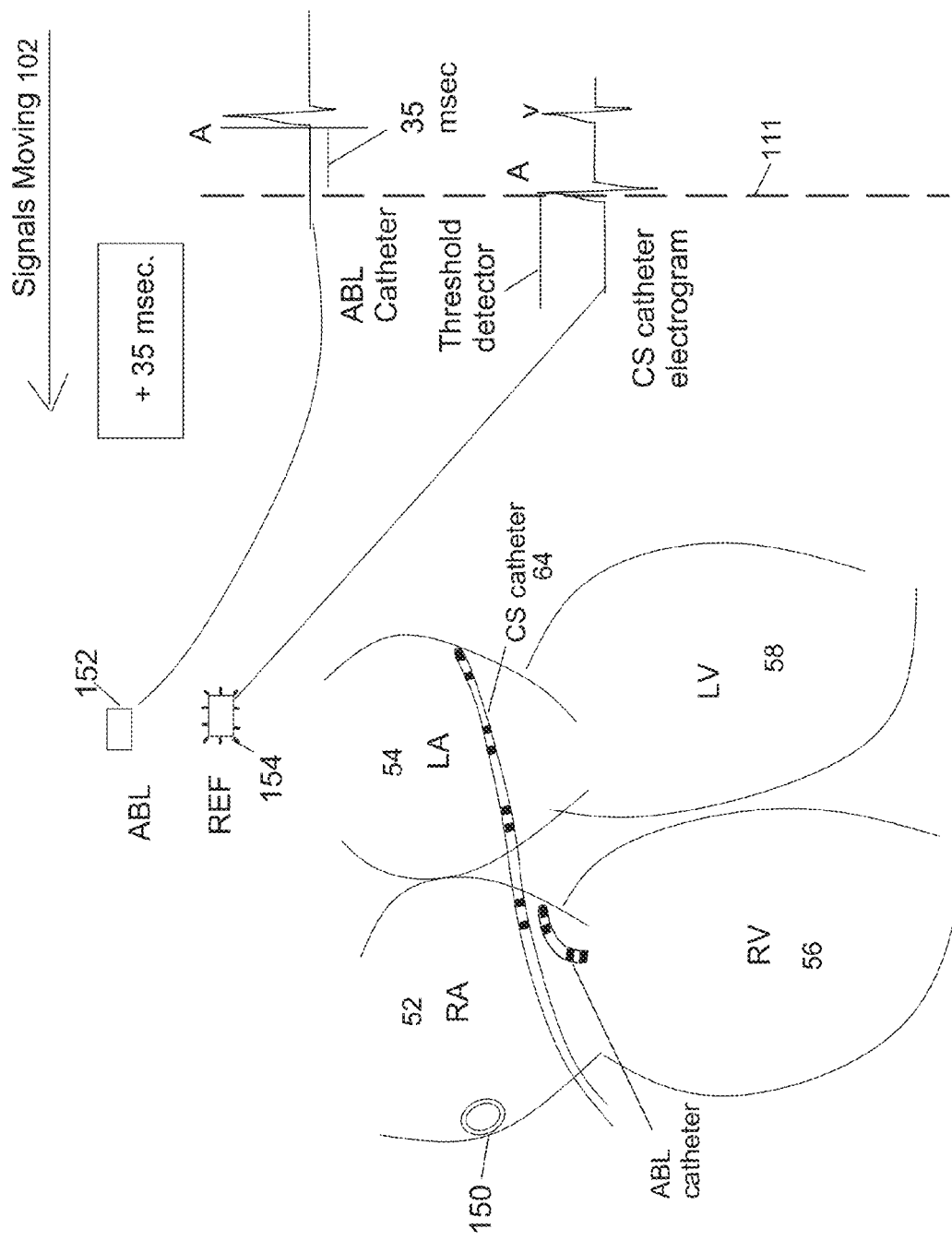
FIG. 9A depicts application of the DVRT mapping system in focal atrial tachycardia, with the REF catheter signal appearing before the ABL catheter signal.

The object of this ablation is to manipulate the ablation catheter, such that the timing of the ablation catheter is the earliest (most negative number) relative to the reference catheter signal. But, as the catheter is continuously manipulated, at some locations the ablation catheter signal may come later than the reference catheter signal. This scenario is depicted in FIG. 9A. As shown in the figure, the numerical value reads +35 millisec. This means that the atrial signal from the REF catheter 64 comes before the ABL catheter signal. Also, the REF catheter LED 154 blinks first and then 35 msec later the ABL catheter LED 152 blinks. Both of these indicators imply that the ablation catheter is not in a good location, and further exploration needs to be performed, by manipulating the ablation catheter to other sites in the atrium.

Figure 9B:
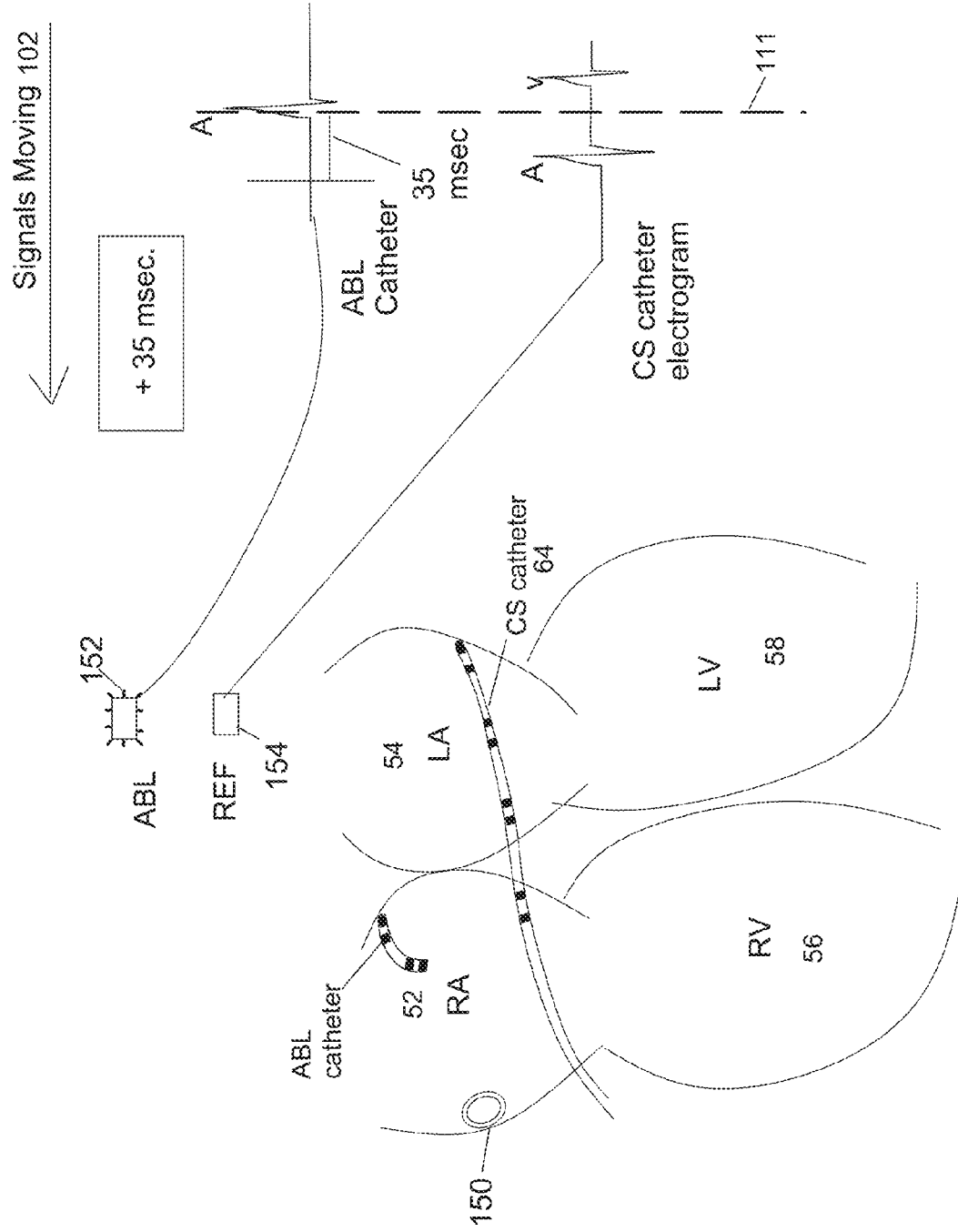
FIG. 9B depicts application of the DVRT mapping system in focal atrial tachycardia, with the REF catheter signal appearing before the ABL catheter signal and the ABL catheter LED blinking.

FIG. 9A depicts that when the atrial signal of the REF catheter crosses the threshold detector, the REF catheter LED 154 blinks. And, FIG. 9B depicts that 35 millicsec later the ABL catheter crosses the threshold detector, and the ABL catheter LED 152 blinks.

Application for Focal Ventricular Tachycardia's (VT)

The method and system of the current disclosure can also be applied to focal ventricular tachycardia's (VT). These include but are not limited to right ventricular outflow tract tachycardia (RVOT), left ventricular outflow tract tachycardia (LVOT), and ischemic ventricular tachycardias. The methodology for focal ventricular tachycardias is similar to atrial tachycardias except that the mapping is done in the ventricle and the reference signal used is either in the ventricle (RV catheter) or a surface EKG signal is used.

Figure 10A:
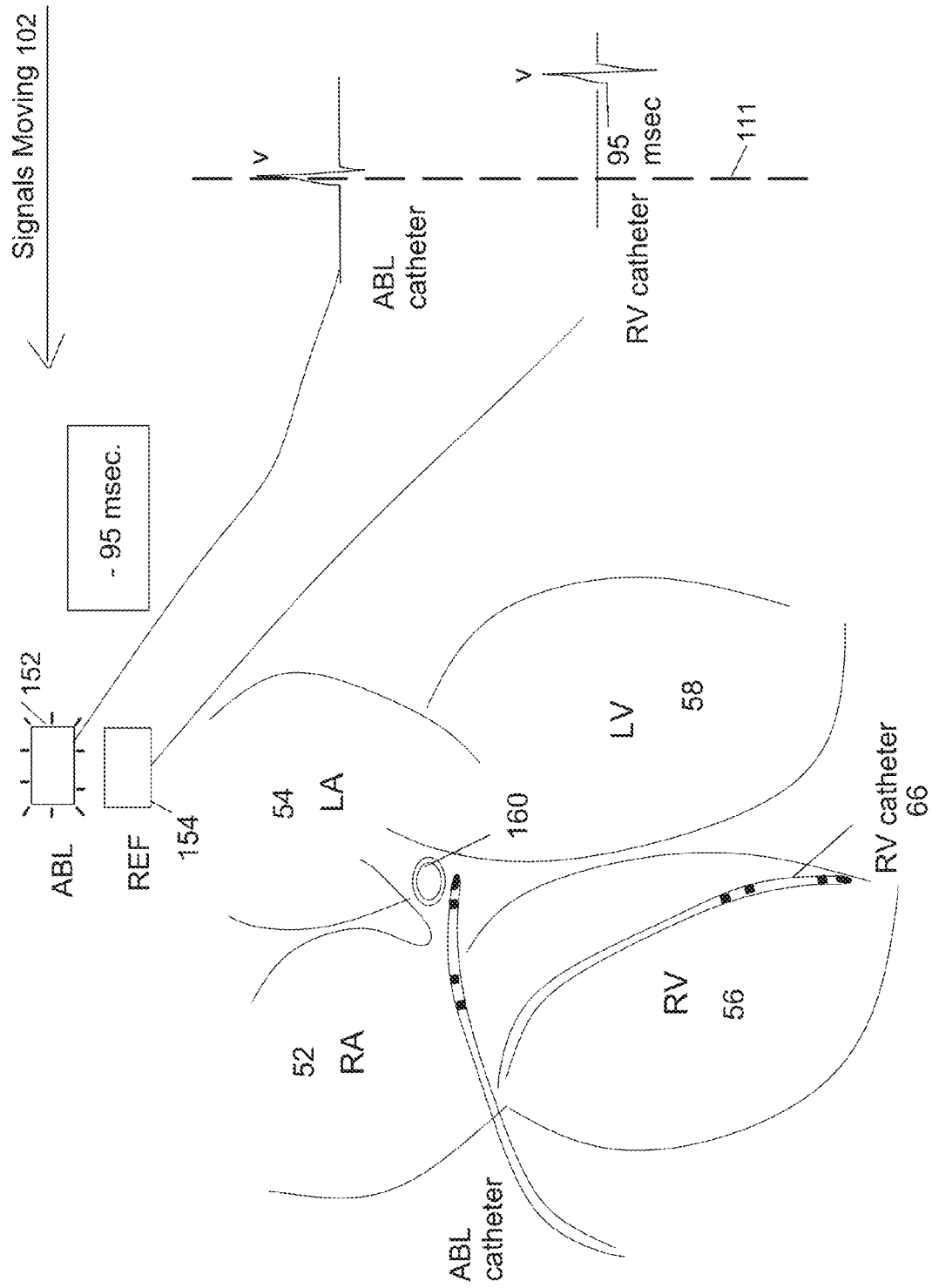
FIG. 10A depicts application of the DVRT mapping system in focal ventricular tachycardia, with the ABL catheter signal appearing before the REF catheter signal.
Figure 10B:
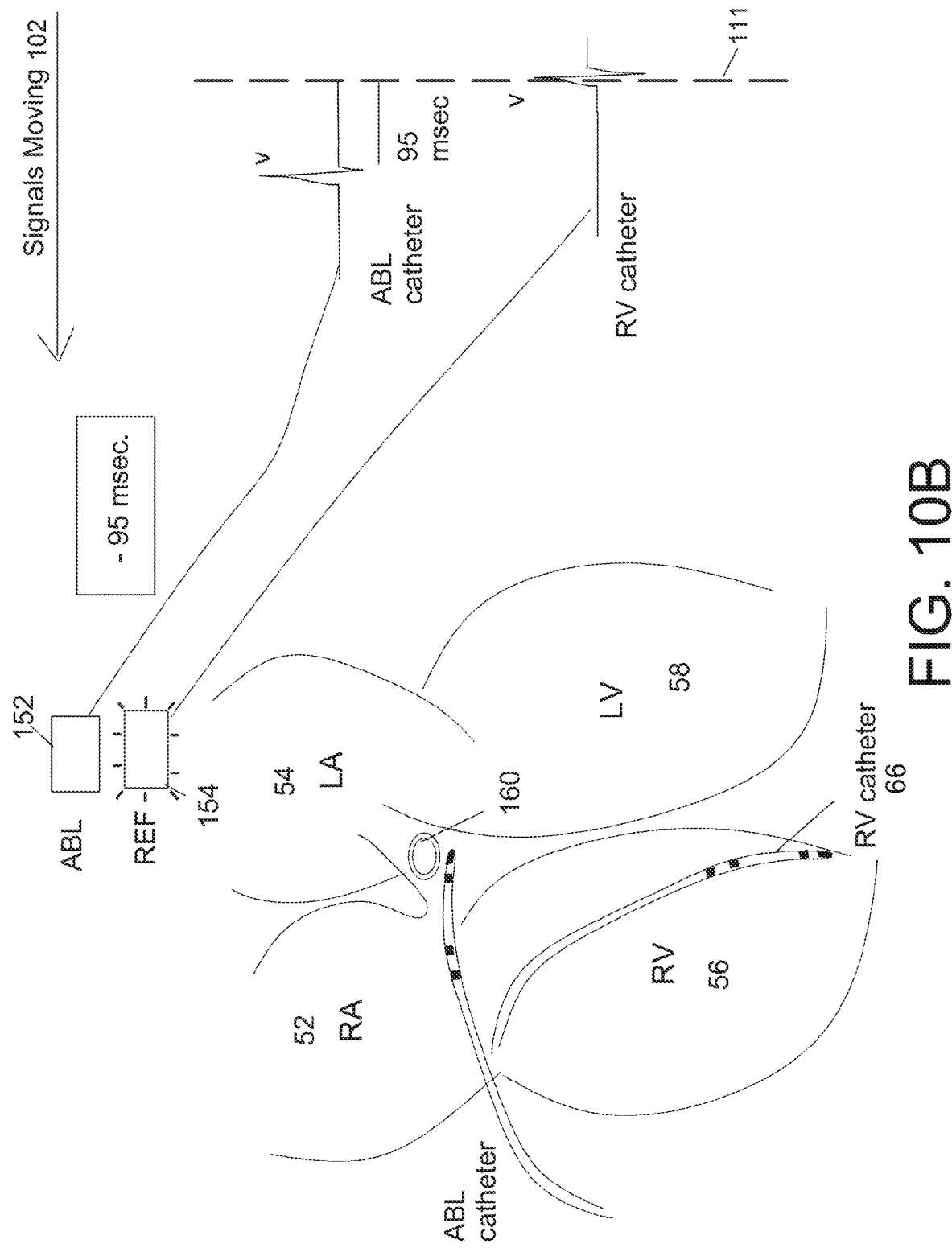
FIG. 10B depicts application of the DVRT mapping system in focal ventricular tachycardia, with the ABL catheter signal appearing before the REF catheter signal, and the REF catheter LED blinking.

Shown in conjunction with FIG. 10A, is an example of mapping for RVOT. In this example timing from the RV catheter is used as a reference. The mapping or ablation catheter 60 is connected with ABL light emitting diode LED 152 such that when the signal crosses the threshold detector, the LED 152 flashes. In this example the numeric indicator reads −95 msec relative to REF signal (t=0). As the ventricular signal (V) from the ablation catheter signal crosses the threshold detector, the ABL catheter LED 152 flashes. In this example after 95 msec, the RV catheter crosses the threshold detector and REF catheter LED 154 flashes, this is shown in conjunction with FIG. 10B.

Similar to focal atrial ablations, the goal in ventricular focal tachycardia is to ablate the site of the earliest activation.

Figure 10C:
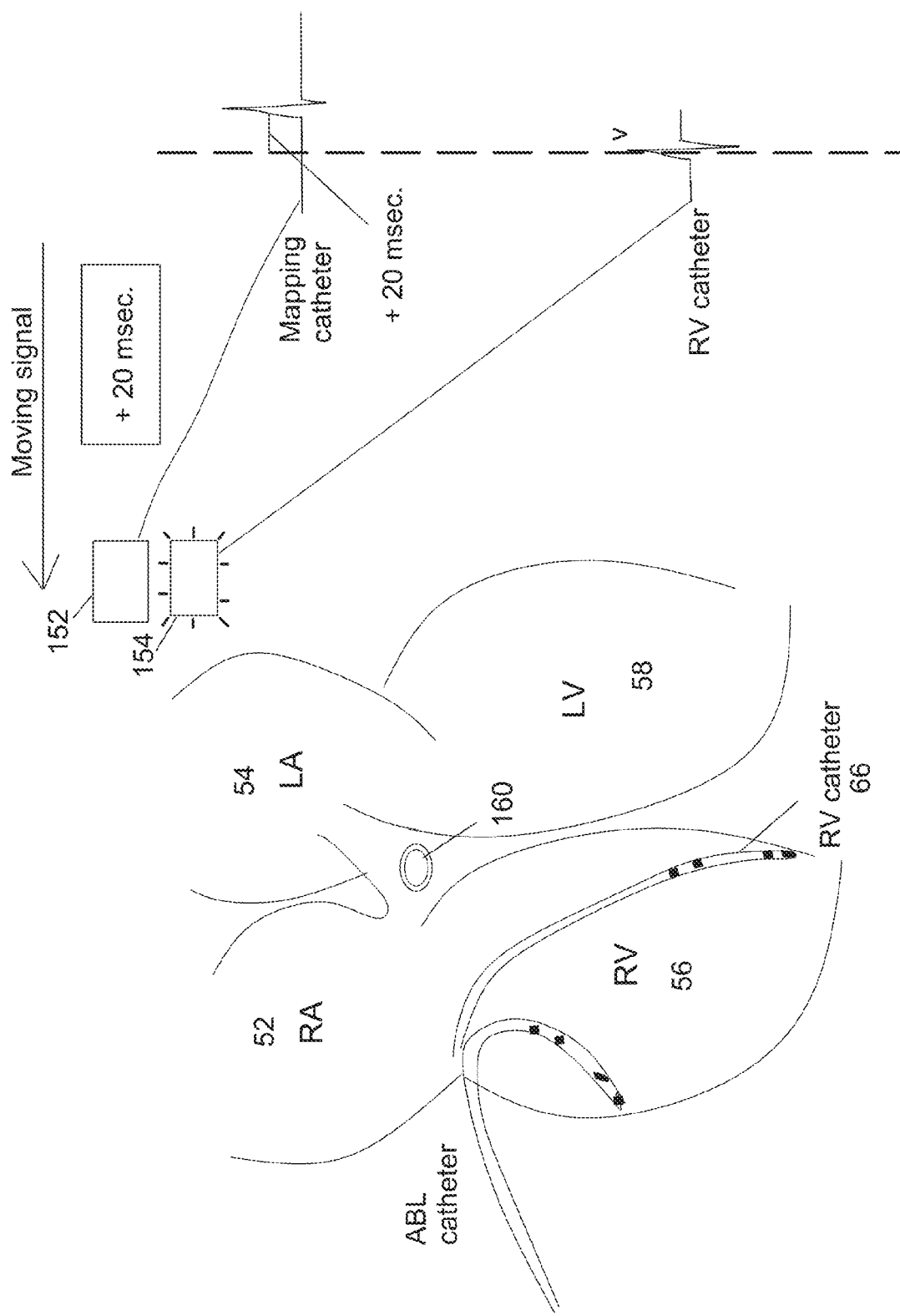
FIG. 10C depicts application of the DVRT mapping system in focal ventricular tachycardia, with the REF catheter signal appearing before the ABL catheter signal.

As the catheter is manipulated within the ventricle, the ablation or mapping catheter may see the signal before the reference catheter, at the same time as the reference catheter, or after the reference catheter. Shown in conjunction with FIG. 10C is a situation where the ablation catheter signal comes after the REF catheter signal. In this case a positive number is displayed, and the RV catheter signal crosses the threshold detector 20 msec before the ablation catheter signal crosses the threshold detector. This also implies that this would be a poor site for trying ablation therapy and that the ablation catheter needs to be significantly repositioned.

Generally, the ablation catheter is manipulated until the earliest activation site is found by the ablation or mapping catheter, and at that point ablation therapy is applied until the tachycardia is terminated. Based on clinical judgment, further ablation therapy may also be applied even after the tachycardia has been terminated.

Currently available electro-anatomical mapping systems are inherently unable to provide real-time propagation mapping as was mentioned above.

It will be clear to one skilled in the art that various different softwares/computer languages may be used to configure and program, and for detecting electrical signals and visually indicating said signals as used in the concept and methodology. Software program code can be written using one of several commercially available software packages. Among the software that can be used for this purpose is LAB WINDOWS/CVI, LABVIEW (National Instruments Corp.), C+, Microsoft Visual C++, Dot Net framework, MATLAB, and Microsoft Visual Basic, among others. Use of these or any other languages for this purpose that are available now or developed in the future, is considered within the scope of the disclosure. Testing of applicant's prototype has been performed using Microsoft visual C++, LabView and MATLAB.

Figure 11:
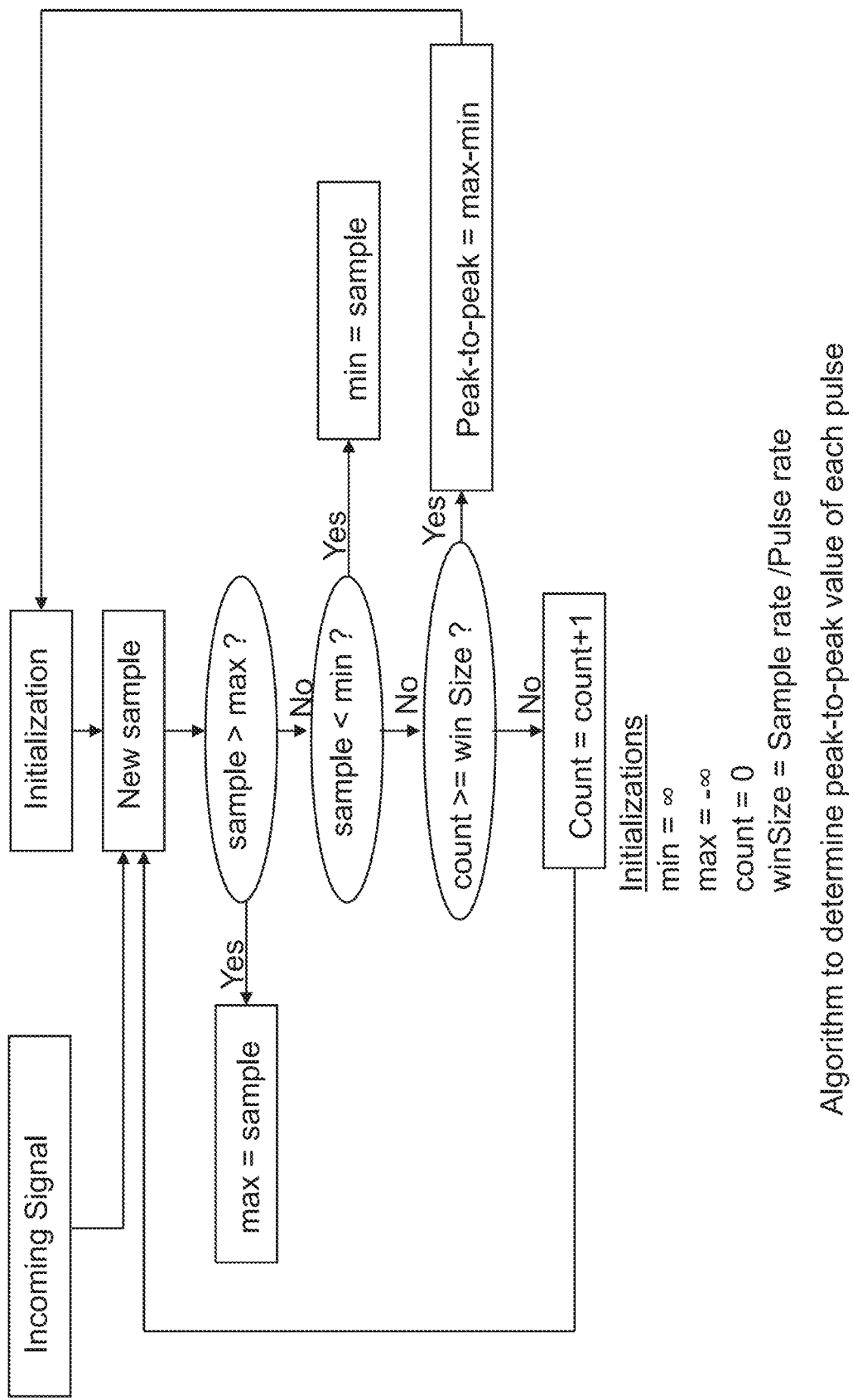
FIG. 11 depicts an algorithm for peak-to-peak detection.

One implementation of signal detection (peak detection) algorithms (implemented with MATLAB) is shown in FIG. 11. The sample rate (samples/second) and the pulse rate (pulses/second) determine the Window size (winSize) with which each pulse occurs. Within this window, the maximum and minimum peaks are calculated to determine the peak-to-peak value of each pulse.

The direct visual, real-time mapping system (DVRT) comprises other signal and timing mapping feature useful in cardiac mapping and ablation. Some of these are described below.

Figure 12:
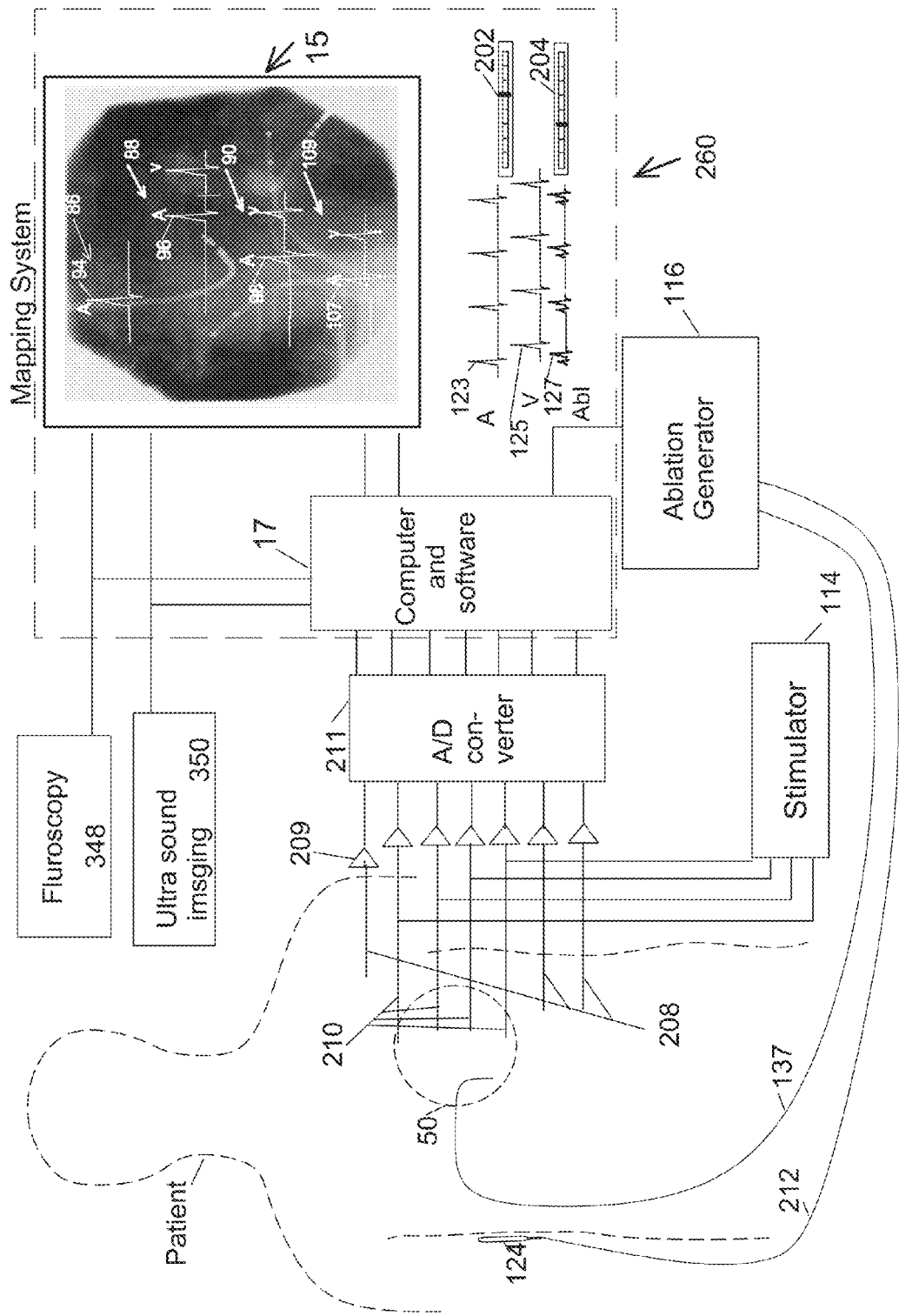
FIG. 12 is a schematic showing acquisition of signals from a patient, and the setup of the equipment in relation to the patient, including various images of the heart brought into the mapping system.

The acquisition of signals from a patient into the real-time mapping system (DVTS) 260 is shown in conjunction with FIG. 12. As shown in FIG. 12, cables 208 from body surface electrodes, and cables 210 carrying intracardiac signals from the heart 50 are amplified, filtered 209 and via A/D converter 211 brought into the computer 7 of the mapping system (DVTS) 260. The computer 17 of the mapping system also comprises the software which is configured for data analysis and processing which is used for guiding the ablation procedure with the mapping system. The signals from the computer 17 are displayed on a monitor shown in FIG. 12 as mapping system display 15. The mapping system computer 17 also interfaces with the ablation generator 116, and stimulator 114 for pacing.

It will be clear to one skilled in the art that the computer 17 can be a desktop computer, a server, a laptop computer, or a tablet such as an i-Pad. It could also be a mobile device that sufficient computing power.

In one aspect of the disclosure, one or more imaging display(s) may be added to the display 15 of the mapping system display. As shown in FIG. 12, examples of these displays without limitation includes ultrasound imaging of the heart, ICE 350, fluoroscopic image 348 of the heart, detailed digital image of the heart such as CT scan or an MRI. Having one or more image of the heart in addition to the electrical signals is advantageous, since detailed anatomical position in addition to electrical activation or timing information is useful for making decision about the ablation site. It will be clear to one skilled in the art that detailed anatomical imaging information such as available from GE Corporation, Siemens, or Philips can be brought in the mapping system display, as an aid for selecting the site for ablation.

The real-time mapping system 260 of the current disclosure finds use in several different types of ablation procedures including, but not limited to, atrial flutter, AVNRT, accessory pathway, atrial tachycardia, atrial fibrillation, VT, and RVOT etc. The novel features for certain types of ablations are described below.

Use of Timing Mapping in Atrial Flutter

Several techniques have been generally described for ablation of typical atrial flutter (i.e. isthmus dependent). All have in common placing lesions in such a way that they bridge or sever a relatively narrow corridor in the low right atrium. Lesion are typically made from the tricuspid annulus directly to the IVC across the subeustachian sinus (isthmus region), or from the tricuspid annulus to the coronary sinus.

Additionally, entrainment procedure in the low right atrial subeustacian isthmus is usually or frequently performed at least once to confirm that the flutter present is indeed a "typical" variety and uses the isthmus zone as a critical element.

For entrainment mapping, the ablation catheter which is also called the mapping catheter or roving catheter is placed in the isthmus region, and paced at a cycle length (CL) which is faster than the tachycardia cycle length (TCL). Once capture is confirmed, the pacing is stopped. The first escape interval after the last paced beat is measured, and compared with the tachycardia CL. If the post-pacing interval (PPI) is similar to the tachycardia CL, then the ablation catheter is in the re-entrent circuit. If the PPI is significantly different than the TCL, then the ablation catheter is not in the circuit and some distance away from the re-entrant circuit.

Even though entrainment mapping is a very useful and sometimes essential procedure, it can be inconvenient for the electrophysiologist during the ablation procedure. Frequently, the electrophysiologist has to break scrub to do the procedure, i.e. perform pacing measurements and measure the appropriate intervals, such as the post-pacing interval (PPI).

Advantageously, in the novel method and system of this disclosure, computer software is configured and programmed which will make the procedure faster and easier by displaying the PPI measurements on the screen and comparing it to tachycardia CL.

Figure 13A:
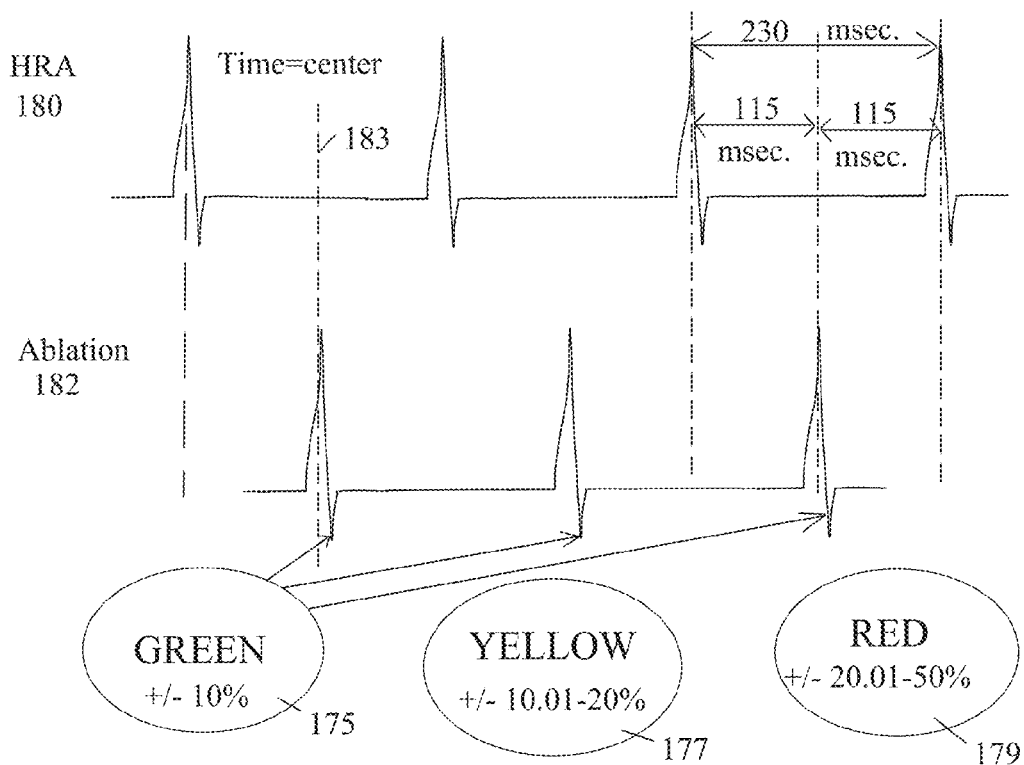
FIG. 13A depicts schematically the positioning of the ablation catheter in the center of the zone of slow conduction/vulnerable conduction in the isthmus, for ablating typical atrial flutter.

A novel feature for aiding in ablation of a typical atrial flutter procedure are shown in conjunction with FIG. 13A. In this embodiment, atrial (HRA) signals 180 and ablation (ABL) catheter signals 182 are displayed on the screen. In isthmus dependant atrial flutter ablations, it is of interest to ablate the zone of slow conduction/vulnerable portion of the circuit. In electrophysiological (EP) terms, this vulnerable portion of the circuit corresponds to when the ablation catheter signals 182 correspond in time to approximately the center of high right atrial (HRA) 180 signals. A coronary sinus (CS) signal may be used instead of HRA signal. Advantageously, the method and system of the current disclosure provides that with the computer software which is configured for this in the real-time mapping system 260. As is known in the art, as the ablation (ABL) catheter or roving catheter is manipulated by the physician, the timing of the ablation catheter signals 182 relative to the timing of HRA signal 180 keeps changing. The general aim is to have the ablation catheter (ABL) signal 182 centered 183 between the HRA 183 signals, as shown in FIG. 13A. As one tool to aid to the physician, the software is configured such that when the ablation catheter signals 182 are within approximately 10-20% of the center 183 of HRA signal in time, it is an idealized site to ablate, because it is in the zone of slow conduction/vulnerable portion of the circuit. In this disclosure, this is indicated to the physician by one of various ways. In a non-limiting example, a green light 175 (shown at the bottom of FIG. 13A) goes ON indicating the desirability to ablate at this site, because this site corresponds to the zone of slow conduction/vulnerable portion of the circuit. In one embodiment, the signal itself may change color. The desirability to ablate at this site, can be shown in any number of ways, which are all considered within the scope of this disclosure.

Figure 13B:
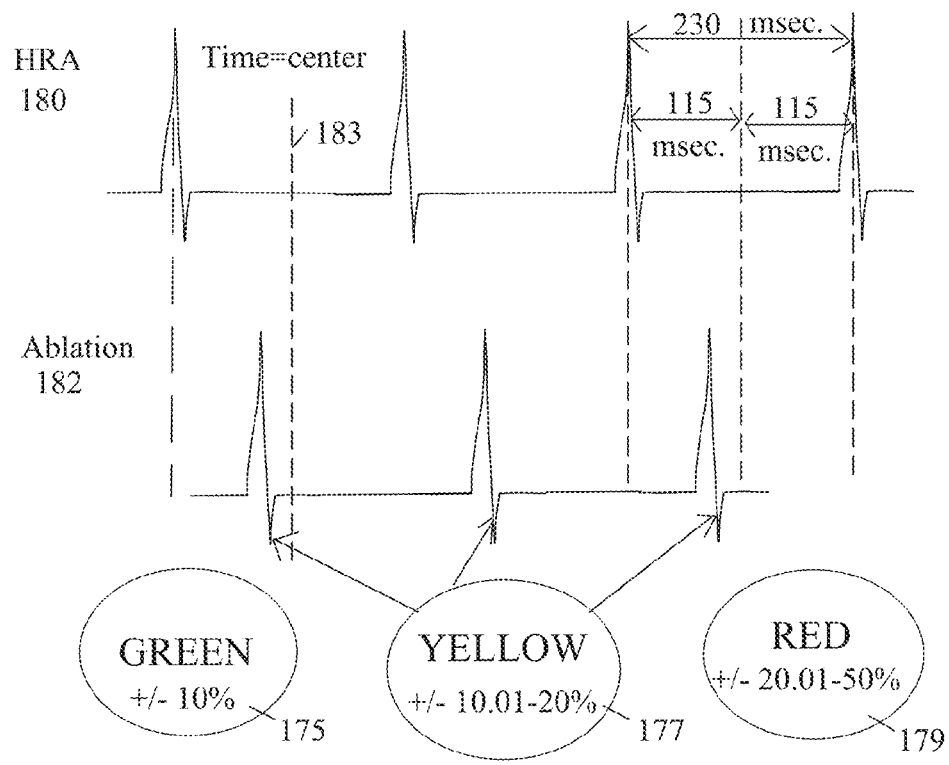
FIG. 13B depicts schematically the positioning of the ablation catheter for ablating typical atrial flutter.

Similarly, as the ablation catheter 182 is moving (from the center) it may be within 10-20% of the center of HRA 183, in which case the yellow light goes on, or the ablation catheter signal 182 turns yellow (shown in FIG. 13B). This indicates to the physician that the desirability of this ablation site is not as good as when the green light 175 is on, but is better than when the red light 179 is on. Again, this "in the middle" situation can be depicted in one of various ways, and any of these ways are considered within the scope of this disclosure.

As the ablation catheter 182 is manipulated, the situation where the ablation catheter is off the center mark, i.e. away approximately 20-50% from the center point 183, which induces the red light 179 to go on, indicating to the physician that the desirability of ablating at this site is not high, and the ablation catheter 182 should probably be manipulated to a better spot or site for ablating. This situation is depicted in FIG. 14. As mentioned previously, this non-centering can also be indicated in various other ways in the method of this disclosure. For example the signal itself may turn red, or the color around the signals may turn red indicating the undesirability of ablation at this site.

It will be clear to one skilled in the art that various different softwares may be used in implementing this concept and methodology. Program code can be written using one of several commercially available software packages. The software that can be used for this purpose includes, but is not limited to Lab Windows/CVI, LabView (National Instruments Corp.), C+, Microsoft Visual C++, Dot Net framework, MATLAB, and Microsoft Visual Basic, among others. Use of these or other functional languages for this purpose that are available now or developed in the future, is considered within the scope of the disclosure. In coding and configuring the software, the timing can be taken (T=0) from the point of signal detection in the CS and ABL catheter. Signal detection can be from simple threshold detection to more sophisticated peak detection algorithms, as long as it consistent to both CS (or HRA) and ABL signals. The formulas for line coding in C++ or VI's in Labview are well known to one of ordinary skill in the art.

Testing of applicant's prototype has been performed using both Microsoft visual C++, LabView and MATLAB.

Frequently, before starting atrial flutter ablation, entrainment mapping is performed. Sometimes, ablation is started and when it is not successful entrainment mapping is performed during the procedure. Advantageously, in the method and system of this disclosure, entrainment mapping is programmed and configured by the software in the computer system to make it convenient for the physician performing the procedure, and to make the procedure go faster and smoother. Entrainment involves pacing from multiple, separate sites within the right atrium at cycle lengths of 10-20 ms faster than the tachycardia cycle length (TCL), observing its effect on flutter wave morphology and estimating proximity of pacing site to tachycardia circuit by analysis of the post pacing interval (PPI). Generally, the pacing site is considered to lie within the tachycardia circuit when the post pacing interval (PPI) is within 30 msec of the tachycardia cycle length (TCL). Entrainment from sites which are outside the flutter circuit will demonstrate manifest fusion on the surface ECG and the PPI will exceed the flutter cycle length (FCL) by more than 30 msec.

Figure 15:
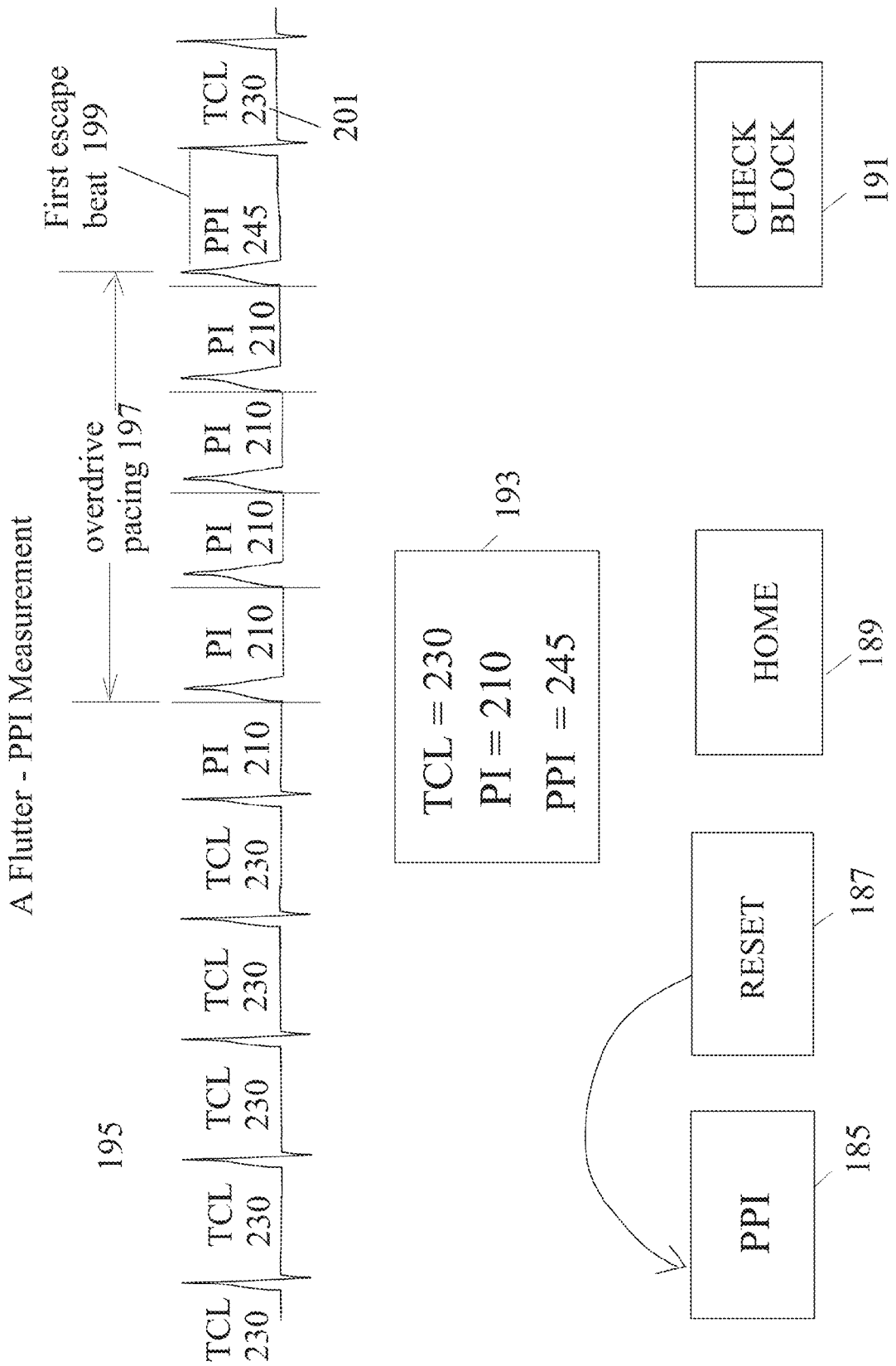
FIG. 15 shows schematically the screen for automated PPI measurements for flutter ablations.

In the method and system of this disclosure, PPI measurement is configured and programmed as is shown in conjunction with FIG. 15. As shown in the bottom portion of FIG. 15, there are three buttons labeled PPI 185, Reset 187, and Home 189. To start the PPI measurement, the PPI button 185 is pressed. This starts the program software to do the PPI measurement analysis which is configured in the program. When the PPI button 185 is active, the program starts displaying the tachycardia cycle length (TCL) 195 on the screen, as is shown in the top of the figure. In this example, without limitation, the tachycardia cycle length (TCL) is 230 msec, and the pacing interval (PI) is 210 msec. As the pacing is started at a faster rate than the tachycardia rate, the software is configured and programmed to recognize this, and a pacing sign 197 is displayed, as is shown in the top center of the figure. This is recognized by the program because the pacing rate is faster than the TCL 195. The software is programmed and configured to recognize these changes in the rate. As soon as the pacing is stopped, the rate drop is picked up by the computer software, which freezes the screen and displays the measurements on the screen. The displayed measurements 193 include values for TCL, PPI, and PI. The PPI interval is the time interval between the last paced beat, and the first escape beat. In this example it is 245 msec. After that the tachycardia interval ensues, which in this example is 230 msec. In one embodiment, the coding may be based on rate alone. In another embodiment, the coding may be based on rate and/or other parameters. For example, when the pacing is started, not only is rate faster, but the initial voltage is also higher due to the large pacing spike. This may be taken advantage of when coding.

In one embodiment, when the reset button 187 is pressed, the software goes into a mode where it is ready to repeat the PPI measurements again, and starts displaying the TCL 95 numbers on the screen. When pacing is turned on and stopped, the PPI measurement is displayed again. PPI measurements may frequently be repeated several times during the flutter ablation procedure. When the last PPI measurement is completed, the Home button 189 (shown on the bottom of the screen) is pressed, which takes the program out of the PPI measurement program and back into the main flutter program.

During the course of the procedure, ablation lesions are performed in the usual manner. After completing the lesions, the line of block is always checked, either in the unidirectional of bidirectional manner. Advantageously, in this disclosure the procedure for checking the line of block is also configured and programmed by the software and is shown in conjunction with FIGS. 16-18.

Figure 16:
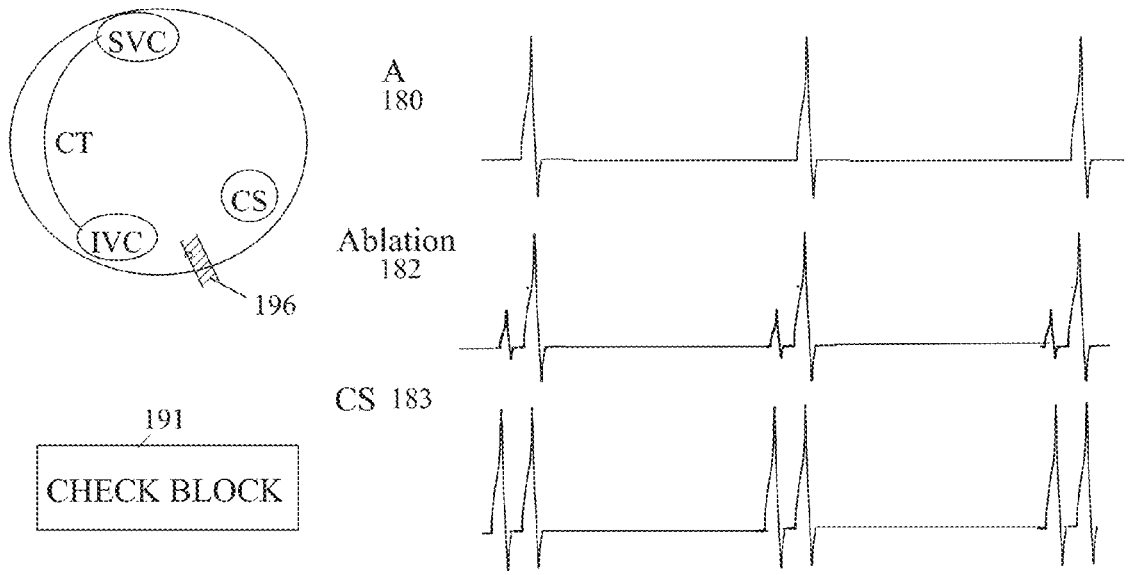
FIG. 16 shows schematically the screen for automated measurements for checking for line of block after completing a flutter ablation line.
Figure 17:
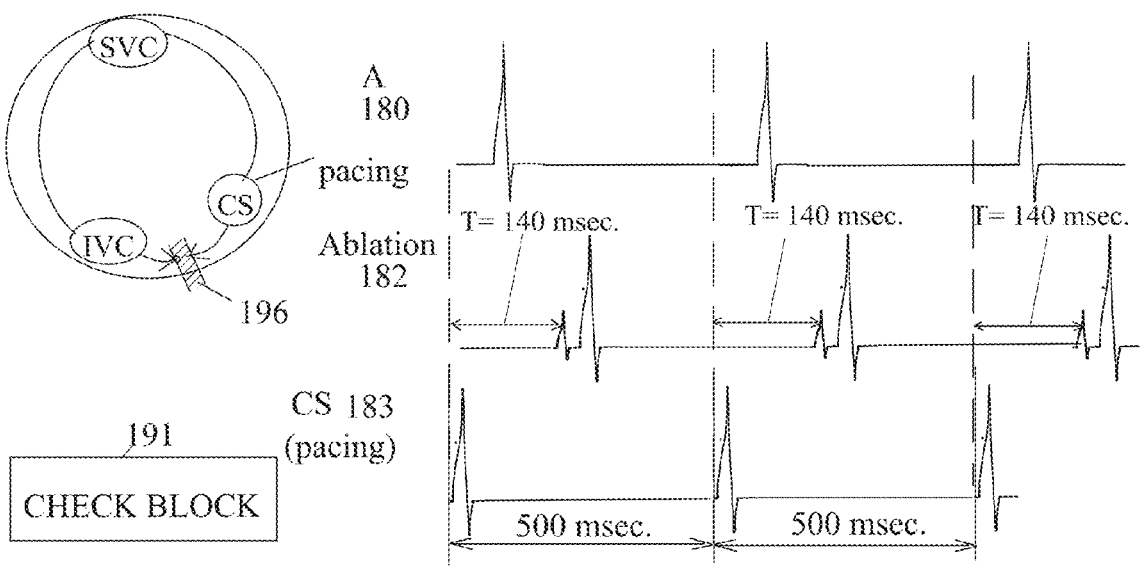
FIG. 17 shows schematically the screen for automated measurements for checking line of block with CS pacing and the ablation catheter on the other side of "ablation line".

As shown in conjunction with FIG. 16, three or more channels of information is displayed on the monitor including that of the atrial catheter (A) 180, ablation (ABL) catheter 182, and coronary sinus (CS) catheter 183. Generally, post ablation line of block can be checked by pacing through the CS 183 catheter and recording the time to the ABL catheter signal 182, or by pacing through the ABL catheter 182 and measuring the time to the CS catheter 183. Advantageously, in the method and system of this disclosure, the software in the computer is configured and programmed such that these measurements are also displayed conveniently to make the procedure go faster and smoother. To check for line of block in the clockwise direction, as shown in conjunction with FIG. 17, the Check Block box 191, shown in lower left corner of the figure is activated. As pacing is performed from the CS 183 catheter, the software is configured and programmed such that the measurement of time from the pacing spike (CS catheter) to the ABL 182 signal recording will be measured by the software and displayed on the screen. As previously mentioned, one of any number of software may used for coding for this purpose. This makes it convenient and faster for the physician performing the ablation procedure. As shown in FIG. 17, in this example the time from the pacing spike (CS 183) to the ABL signal 182 is 140 msec.

Figure 18:
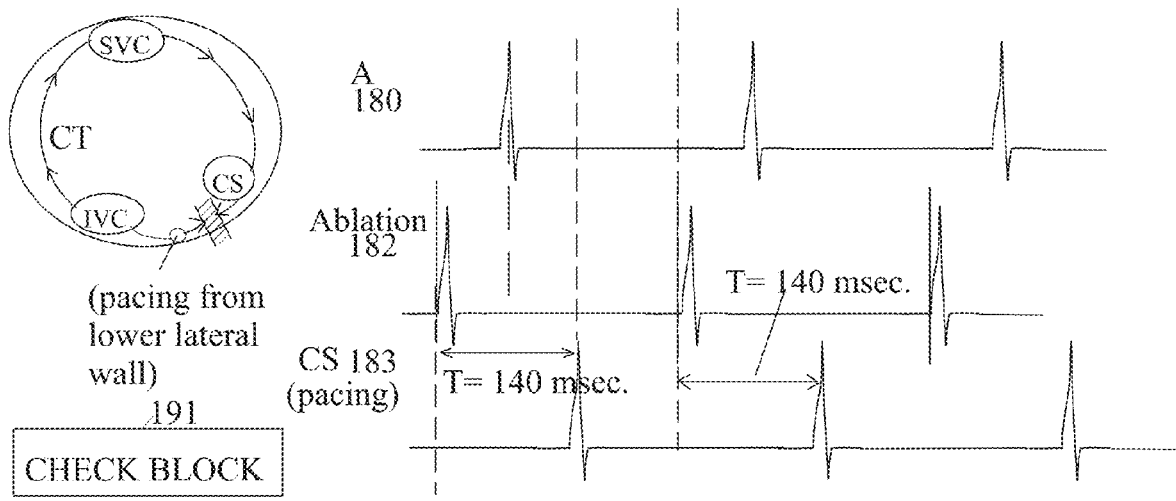
FIG. 18 shows schematically the screen for automated measurements for checking line of block with pacing from the ablation catheter (low lateral position) and the CS signal being on the other side of "ablation line".

Similarly, checking for line of block in the counterclockwise direction is shown in conjunction with FIG. 18. In this case, the pacing is performed from the ABL 182 catheter, and time is measured from the pacing spike on the ABL 182 signal to the time on the CS signal 183. As shown in the example in this figure the time is also 140 msec.

After the measurements are completed, the software is configured such that by clicking on the Check Block box 191 again takes the program back to the main atrial flutter menu.

Figure 19:
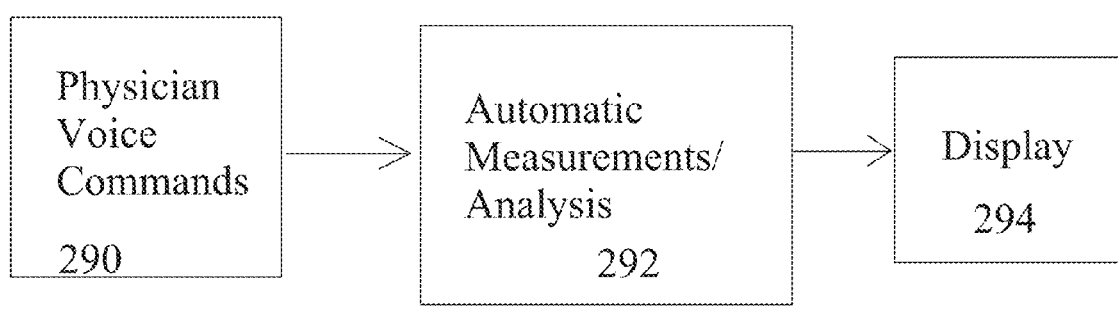
FIG. 19 is a block diagram of the general concept for voice activation of commands.

In one aspect of the disclosure, the automated measurements can be activated and performed by physician's voice activated commands. The voice activated commands may be used for atrial flutter, or may be used for any other arrythmia's. For this embodiment, as shown in conjunction with FIG. 19, the physician gives a set of predetermined voice commands 290, which activate a set of automatic measurements 292 which are then displayed 294 on the monitor, making the procedure proceed quickly and more efficiently.

Figure 20:
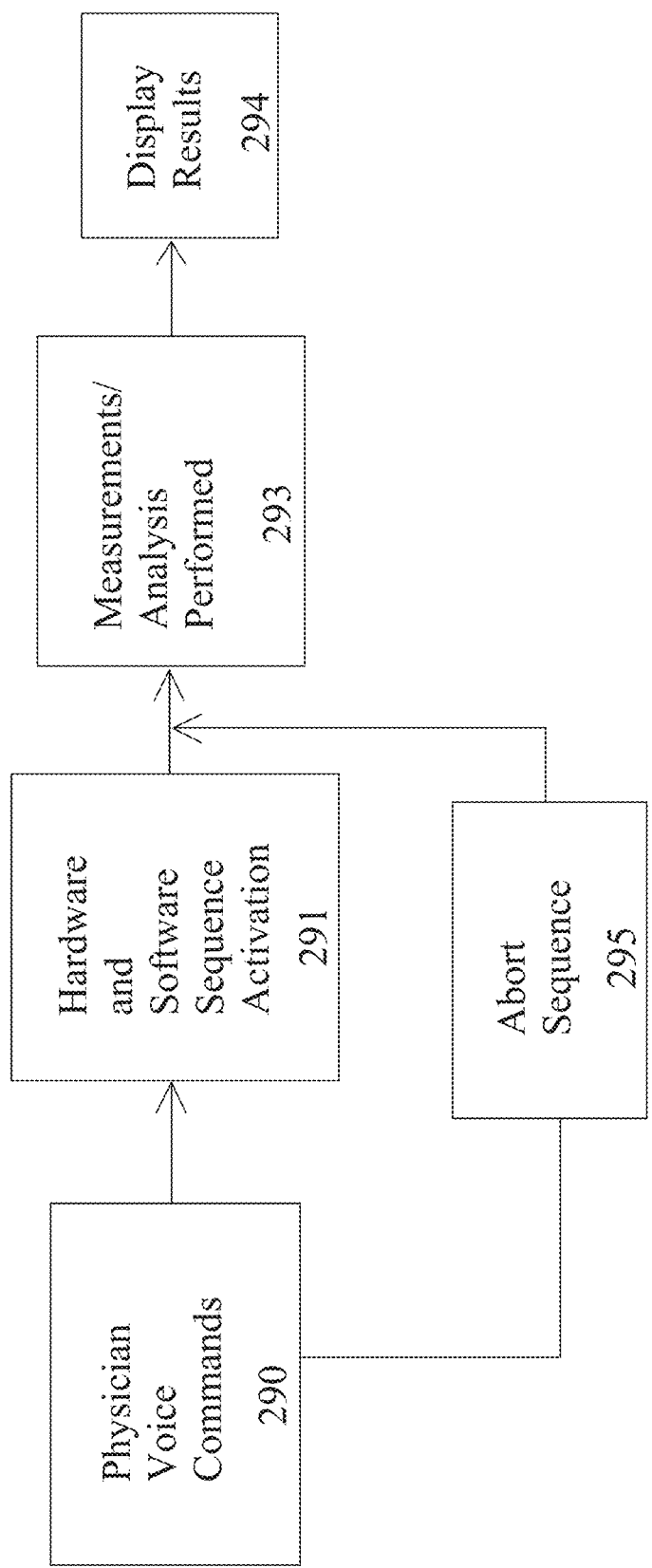
FIG. 20 is a block diagram of the general concept showing abort sequence block.

Once the measurement sequence is activated, the sequence can be aborted either by voice commands or manually overriding on the computer via the mouse or keyboard. This is shown in conjunction with FIG. 20, where physician voice commands 290 activate hardware and software sequence activation 291. The sequence can be aborted 195 at any time during the measurement phase. If the sequence is not aborted, the measurements are performed 293 and the results are displayed 294.

Figure 21:
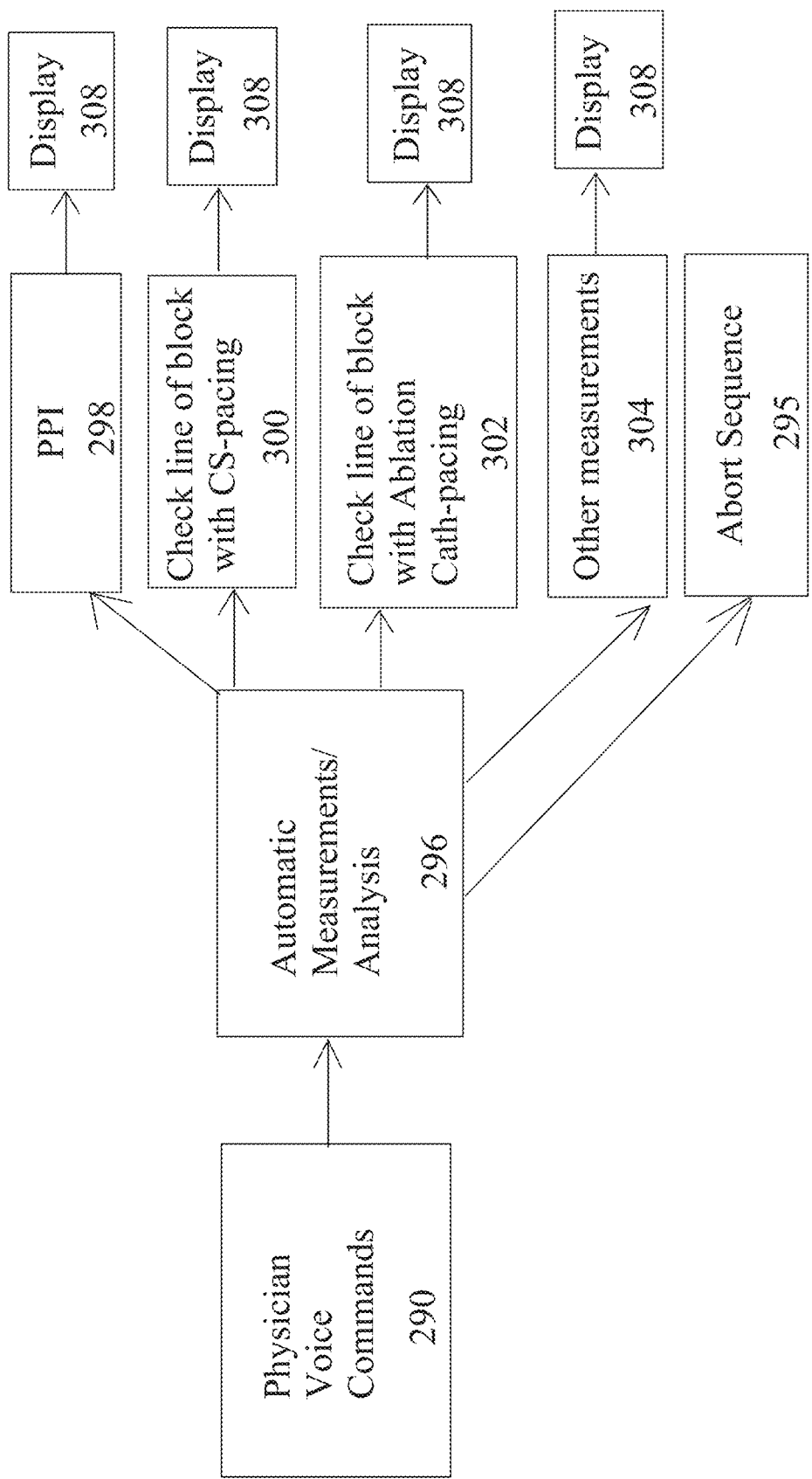
FIG. 21 is a block diagram of the general concept showing various measurements that can be activated or performed.

Shown in conjunction with FIG. 21, the physician's voice commands 290 can be used for various different measurements 296, such as without limitation, measurement of post-pacing interval (PPI) 298, checking for line of block with CS-pacing 300, checking for line of block with pacing from the ablation catheter 302, and various other measurements 304. Once these measurements are performed, the results are displayed 308 on the monitor.

Figure 22:
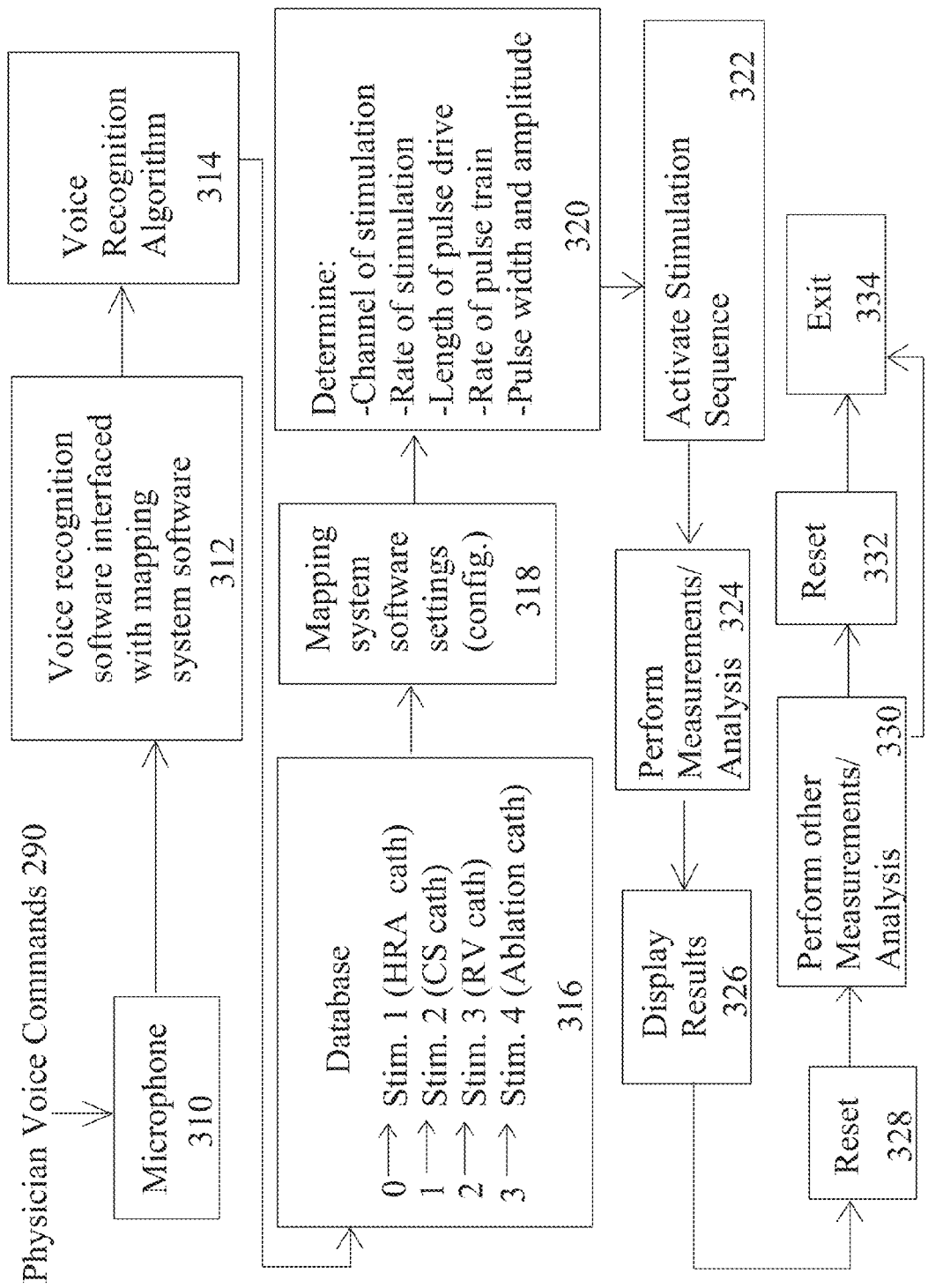
FIG. 22 is a more detailed block diagram of the concept of voice activated commands for automated measurements.

The sequence of events for this embodiment is generally shown in further detail in conjunction with FIG. 22. The physician's voice commands 290 are spoken into a microphone 310 which is configured and connected to the computer 17. The voice recognition software 312 is the interface to the mapping system. The voice recognition software may be Microsoft Windows based software which may be interfaced to the Mapping system software, or may be any available voice recognition software that is available which is then interfaced with the Mapping system software. Some of the commonly available voice recognition software are Dragon Naturally Speaking, Speakeasy, Microsoft Office, these or any other speech recognition software may be used. Predetermined voice commands, are coded and stored in a database 316 within the computer 17. Also, stored in the database 316 is the hardware configuration of the pacing stimulator 114 (shown in FIG. 12) which is connected to the computer and software 17 via a junction box. The hardware configuration includes the different catheters connection information. Typically, the HRA catheter is connected to channel 1 of the stimulator, the CS catheter is connected to channel 2 of the stimulator, the RV catheter is connected to channel 3 of the stimulator, and the ablation catheter is connected to channel 4 of the stimulator. Other connection configurations may also be used. Whichever catheters are connected to the four channels of the stimulator, it is configured into the computer. This information is stored in the database 316 along with the other information.

The voice activated commands are coded. Depending on the voice activation commands, the information is decoded and along with the other information that is stored in the mapping system software configuration file. For example, if the command is "check PPI", the decoded information would calculate the tachycardia cycle length (TCL), pace from the ablation catheter (stimulation Channel 4 in this example) at a cycle which is a predetermined level faster than the tachycardia cycle length (TCL) to capture and drive the atrium faster. The decoded information would also contain the length of pulse drive, and pulse width and amplitude of the pulses. Once the proper sequence is activated, the pulse train is delivered as per the coded pre-determined instructions. Once the pacing interval is established, the pacing is recognized by the computer software and stopped after a pre-determined number of pulses, and the first escape interval is measured and displayed on the monitor, as was previously described in conjunction with FIG. 15.

The software is also configured such that the stimulation sequence can be aborted any time with a coded voice command or a command via the keyboard or mouse. These measurements can also be repeated via coded commands multiple times.

Similarly, the measurement for checking for line of block is also automated, as was described in conjunction with FIG. 17 and FIG. 18. The same methodology is used as just described above with different predetermined code words. For example, with appropriate voice commands the checking for line of block with CS pacing is performed by the computer software, by stimulating the appropriate channel which is connected to the CS catheter (in this example stimulation channel 2). In this case, the decoded information contains the cycle length for pacing (typically around 500 msec), the electrode pair for pacing (typically a proximal pair), the number of cycles in the pulse train, and pulse width and output amplitude. As was described earlier, in conjunction with FIG. 17, the measurement that is performed is the time between the CS pacing spike and the signal from the ablation catheter which is placed lateral to the line of block for this measurement. This time is measured and displayed on the screen 308. The measurement can be repeated or the program can be reset.

Similarly, the automation of measurement for checking for line of block in the counterclockwise direction was previously described in conjunction with FIG. 18. This measurement sequence can be similarly activated and measured and displayed. In this case, the pacing is performed from the distal tip of the ablation catheter, (channel 4 in this example), and the measurement is made from the pacing spike on the ablation catheter to the CS catheter. Again, the ablation catheter is positioned in the low lateral position just lateral to the ablation line.

Application to Early Activation Timing

Another application of the real-time Mapping System (DVRT) 260 is for ablating cardiac arrhythmias where early activation mapping is needed. Early activation mapping relative to a reference signal (where t=0) is essential for mapping many types of arrhythmia's. Some examples, without limitation, are atrial tachycardia (AT), ventricular tachycardia (VT), right ventricular outflow tract tachycardia (RVOT), accessory pathway mediated tachycardia (AVRT), among others. Early activation mapping with the DVRT 260 is shown in conjunction with FIGS. 23-26.

Figure 23:
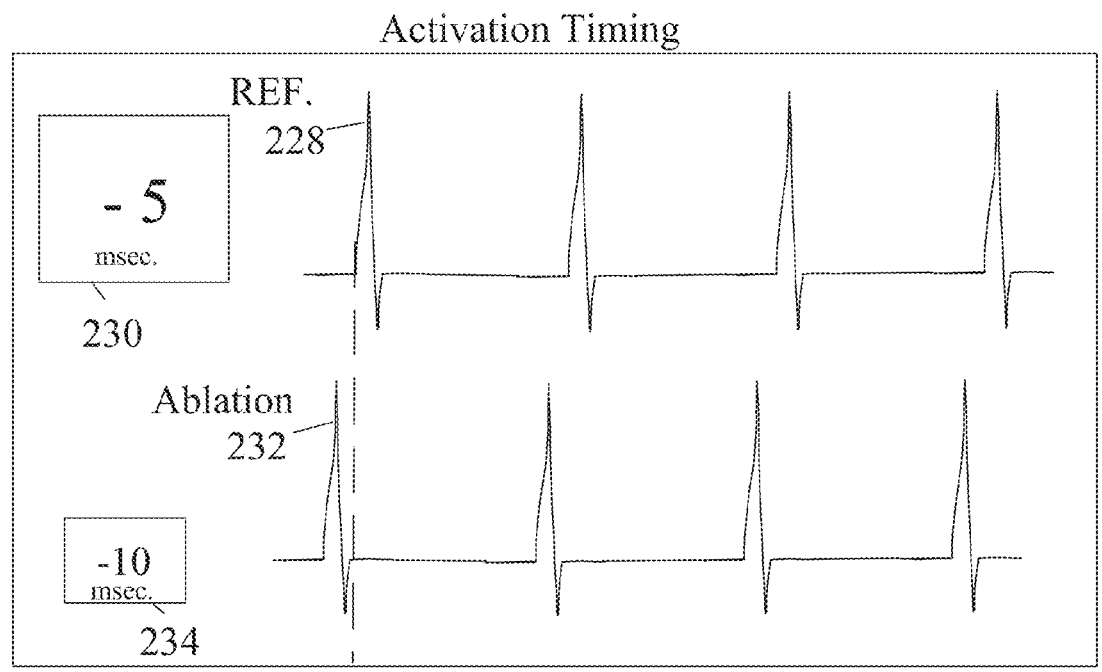
FIG. 23 shows schematically the screen for early activation timing, with an example where the ABL catheter precedes the reference catheter, and the timing is displayed as a negative number.

Shown in conjunction with FIG. 23 is one example of activation mapping using the current system and method. In one embodiment, as shown in the figure a reference signal is displayed (REF 228) on the screen. The reference signal is any signal that is used for comparison of timing, i.e. for the reference signal t=0. The timing of the ablation catheter signal (ABL 232) may be earlier than the REF signal 228, same as the REF 228, or later than the REF signal 228. In the method and system of this disclosure, the software is configured and programmed to continuously measure the time between the REF signal 228 and ABL signal 232, and display it in large and convenient way as to what the current timing of the ABL signal 232 is relative to the REF signal 228 in real-time or beat-to-beat basis. This is shown in FIG. 23 as block 230 where the time is displayed as −5 msec (relative to the reference signal) in this example. To make it more convenient for the ablating physician, the block 230 displaying the relative value is coded in color whenever the relative value is negative (generally the more negative the better). As one example, without limitation, whenever the ABL signal 232 is earlier than the REF signal 228 or same as the display box 230 turns green as an indication that the ablation target is generally close and the timing is relatively good.

As an another example, whenever the ABL signal 232 is after the REF signal 228, i.e. the value of relative number is positive, the display box 230 turns red indicating that the ablation site is not close. Alternatively, when the display box 230 value is negative, the color of the ABL signal 232 itself may turn green and when the display box 230 is positive, the color of the ABL signal 232 itself may turn red, or some other color indicating that the site in not good for ablating. It will be obvious to one skilled in the art, that the indication may be displayed in one of various ways, and any of ways indicating a relatively good or bad site is considered within the scope of this disclosure.

Advantageously in the current system, instead of manually measuring the time between the REF signal 228 and the ABL signal 232, which is slow and distracting to the procedure, the value is not only automatically displayed but is also updated continuously in real-time, making the procedure faster and smoother without distractions. As for the flutter application, one of many different software available can be used for its implementation, and the use of any software is considered within the scope of this disclosure.

An additional feature of the current system is that the software is configured and programmed such that there is another display box 234 shown in the bottom left of FIG. 23, which displays the "best" negative value that has been observed in the current session. This serves as a reference as to the best number so far that needs to be "beaten" to get to a better site.

Figure 24:
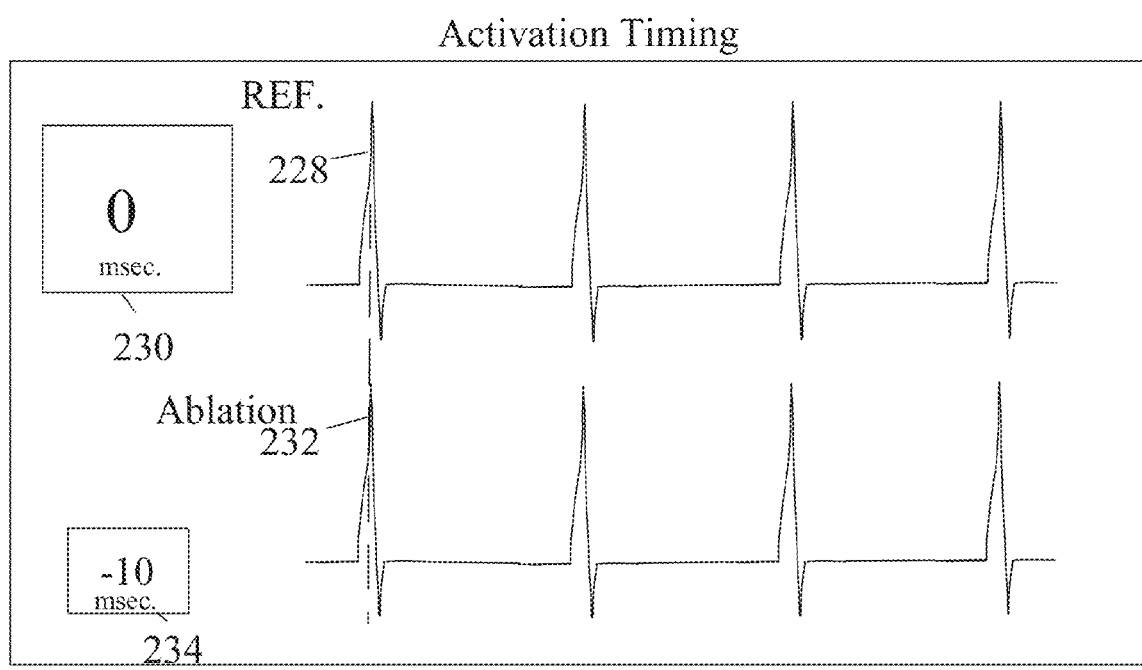
FIG. 24 shows schematically the screen for early activation timing, with an example where the ABL catheter is at the same time as REF catheter, giving a value of 0 msec in the display on the top left of the figure.
Figure 25:
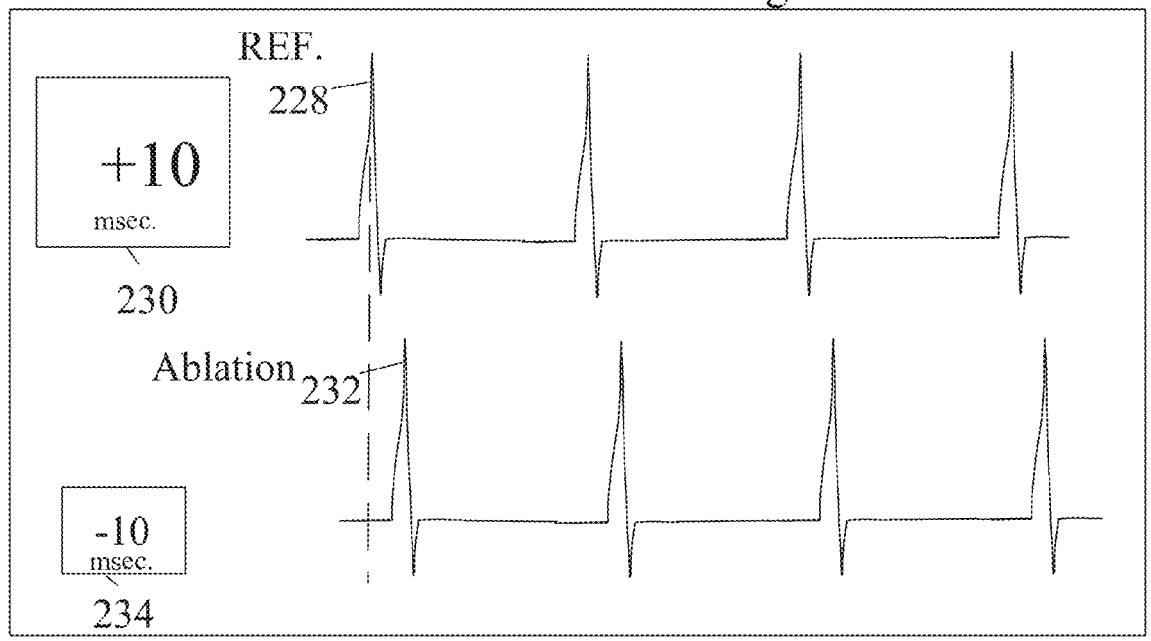
FIG. 25 shows schematically the screen for early activation timing, with an example where the ABL catheter is later in timing than the REF catheter, giving a value of positive number in the display on the top left of the figure.
Figure 26:
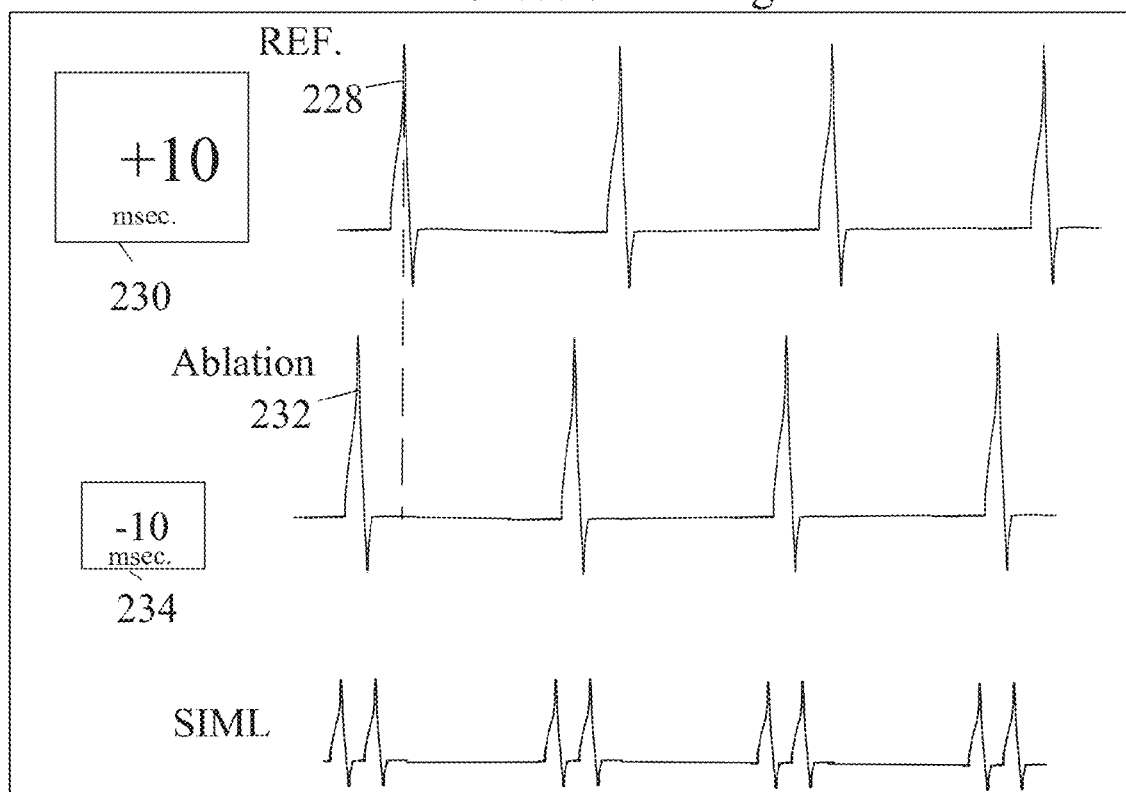
FIG. 26 shows schematically the screen for early activation timing, with an example where the ABL catheter precedes the reference catheter, and a third channel where the REF signal and the ABL are superimposed on each other.

FIG. 24 shows an example where the timing of the REF signal 228 is the same as ABL signal 232. In this example, without limitation, the display box turns green. Shown in FIG. 25 is an example where the ABL signal 232 is after the REF signal 228, i.e. the display number is a positive number. In this example, without limitation, the display box stays blank or turns red, indicating the undesirability of the site for ablation. The undesirablility of the site may be indicated by many other means, another example being the color of ablation signal turning red. In one embodiment, shown in conjunction with FIG. 26, a separate channel is displayed where the REF signal 228 and ABL signal 232 are superimposed. This will be helpful to physicians in determining the appropriate activation timing. The use of early activation timing may be for non-ischemic (normal heart) or ischemic heart cases.

Figure 27:
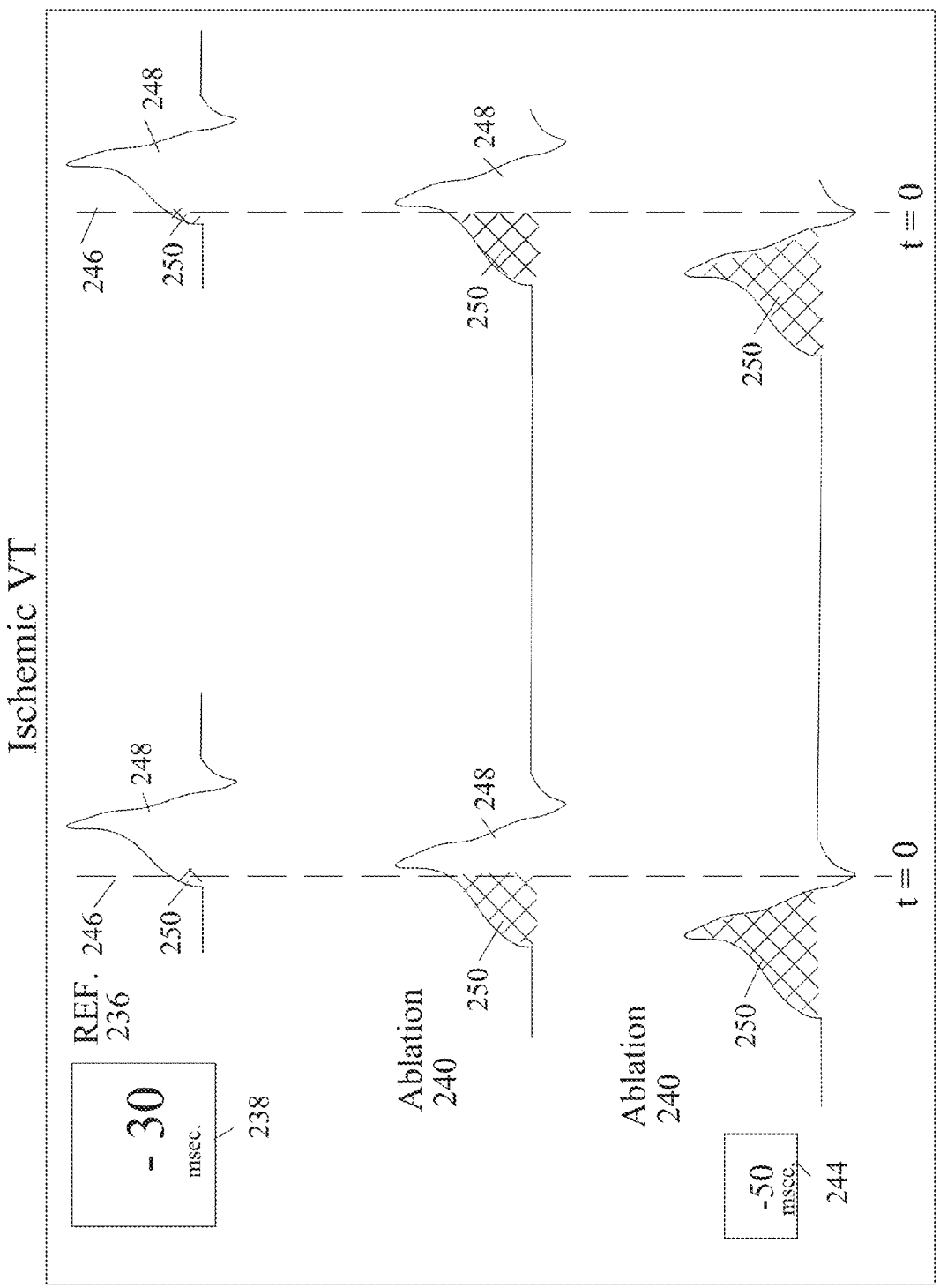
FIG. 27 shows schematically the screen for early activation timing for ischemic VT where the complex is wider and the part of the complex which precedes the reference is shaded with a different color.

In one embodiment, particularly useful for ischemic VT cases is shown in conjunction with FIG. 27. It is known in the art, that in ischemic VT cases the signals can be very wide. In this embodiment, a line 246 is drawn from the fiducial point (where t=0) of the REF signal 236 which extends to the ABL signal 240. In this embodiment, the part of the ABL signals 240 that is before the line depicted as 250 is color coded to visually show the early activation part. As the catheter is manipulated, and an earlier position is obtained, more part of the total signal 248 will be color coded to the earlier activation position, which is shown in the bottom tracing 250 in FIG. 27.

Advantageously, in this methodology the physician can see the full signal to appreciate any potentials (early potential, mid diastolic potential etc), as well as, see how the timing of the ABL signal 240 relative to the REF signal 236. The color coding scheme may be any scheme that may be used. As one example, without limitation, the part of the ABL signal 240 that precedes the fiducial line 246 may be color coded green, to show the desirability for ablation. Similarly any number of other color coding schemes may be used and are considered within the scope of this disclosure. Also, as shown in FIG. 27 the activation timing block 238 is also displayed as an additional aid to the ablating physician.

Template Matching for Tachycardia

In this aspect of the disclosure, the screen for template matching is shown in conjunction with FIGS. 28 and 29. In FIG. 28 template matching is shown where the clinical tachycardia morphology 280 and pace map morphologies 285 are shown adjacent to each other. In this aspect of the disclosure, 12 channels of surface lead information (i.e. leads I, II, III, aVR, aVL, aVF, V1, V2, V3, V4, V5, V6) is brought into the program with 12 inputs into the data acquisition's ND converter (FIG. 12). The software in the computer is configured such that by inducing the tachycardia, a store template 220 button on the screen stores the 12 surface channels of template for later comparison. The goal of template matching is to aid the physician to the ablation site, and increase the efficacy of the ablation procedure.

When pace mapping is performed in normal sinus rhythm, as shown in conjunction with FIG. 28, the original template of the clinical tachycardia 280 and pace map morphologies 285 are displayed adjacent to each other. This gives the ablating physician a quick look at the match between the template and the pace map morphology from the site where the catheter is located at the time. This procedure can be repeated as many times as needed to get a pace map that is almost identical to the clinical tachycardia. In the example in FIG. 28, signals from three leads shown as numbers 270, 271, and 272 are not matching.

Further, as shown in conjunction with FIG. 29, by pressing the superimpose template button 224 the clinical tachycardia template 280 and the pace map template 285 are superimposed on each other. In one embodiment, a table displaying the match of each of the 12 leads is shown below, with percent match for each of the 12 leads. Therefore, by utilizing the correlation function built into the software program, a 8/12 match (as an example) is displayed on the screen. A closer look reveals that channels marked with numbers 273, 274, 275 and 276 are not a match. Again, this may be repeated as many times as needed to get an appropriate match for the optimal ablation site. Advantageously, by configuring and programming the software which automats this procedure, the ablation procedure can proceed in an efficient and efficacious manner.

ECG Localization

In one aspect of the disclosure, initial localization or regionalization for the location site or exit site of the arrhythmia is performed utilizing the surface leads. This is typically done with a 12-lead EKG which are brought into the mapping system via ND converter as was shown in FIG. 12 previously. In some cases, additional leads to the standard 12-leads may be used, i.e. 12-18 lead systems may also be used.

Initial 12-lead localization or regionalization is very useful for many different types of arrhythmia's, including but not limited to Atrial tachycardia (AT), antegradely conducting accessory pathway such as Wolf-Parkinson-White syndrome (WPW), Ischemic VT, Idiopathic VT (RVOT or LVOT), and PVC mapping, among others.

In this disclosure, even though this embodiment is described in detail for AT and ischemic VT, it will be understood that it is applicable for all arrhythmia's where surface leads can be used for localization.

It will be clear to one skilled in the art that the EKG localization based on the 12-lead can be interactive or may be done automatically by the computer program. In the embodiment where the 12-lead localization is performed automatically, the computer software is programmed and configured such that it evaluates morphology in each lead whether the P-wave or QRS complex is positive, negative or isoelectric. Based on the said morphology information and other information such as, including but not limited to, area under the curve, width of the QRS complex, and amplitude of the signal, the program makes a determination based on the flowchart logic as described below for the interactive portion of the program.

Figure 30:
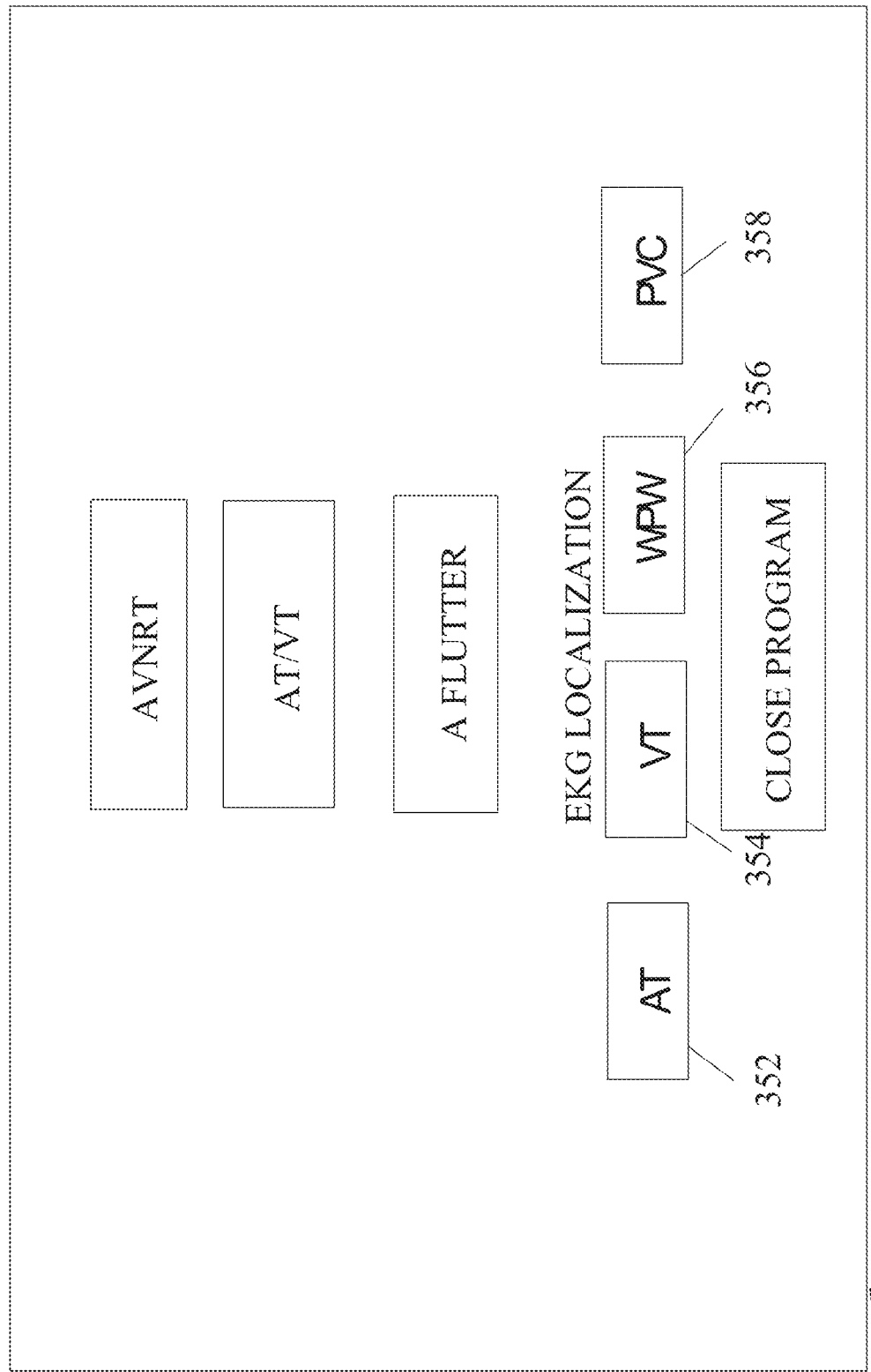
FIG. 30 shows one of the main menu screen of the program for ECG localization.

One implementation of the physician interactive program is shown in conjunction with FIG. 30, which shows the opening screen of this embodiment. In this screen under the EKG Localization portion the options shown are AT 352, VT 354, WPW 356, PVC 358, other programs not shown in this figure may also be included there.

Figure 31:
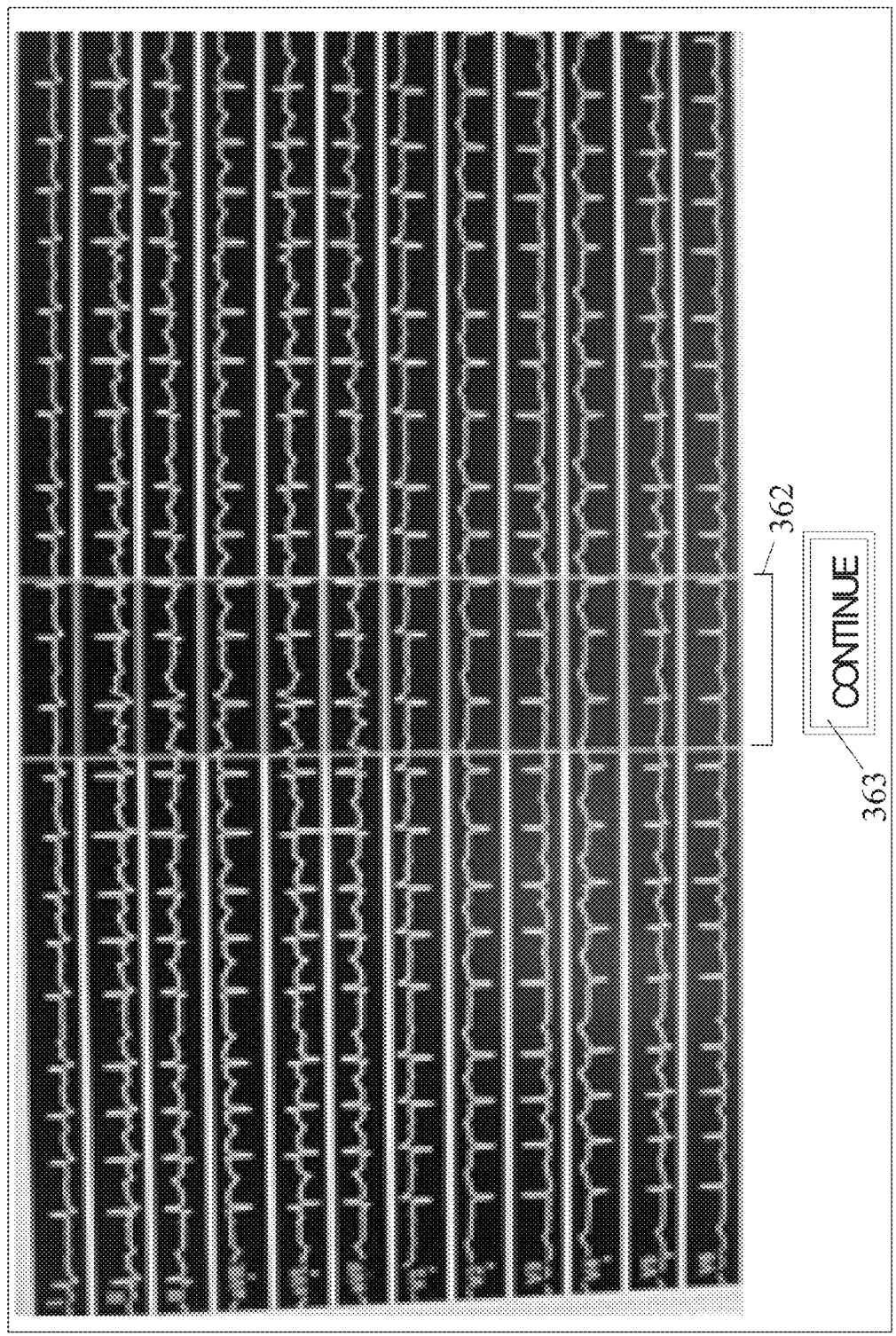
FIG. 31 shows the segment selection screen for the AT localization program.
Figure 32:
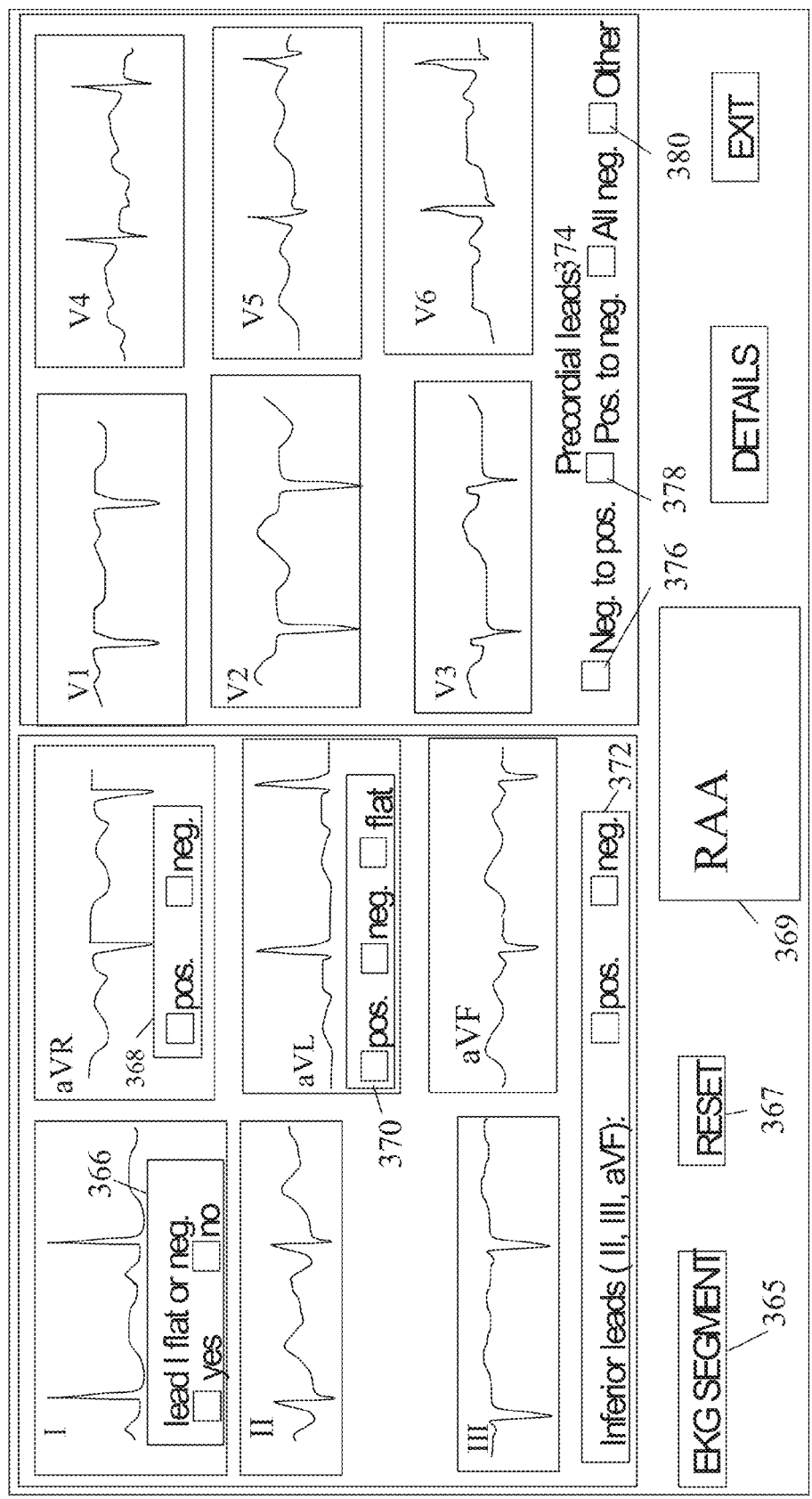
FIG. 32 shows the question answering screen for the AT localization program.

Upon clicking AT 352, the screen shown in FIG. 31 is displayed. In one embodiment, the rationale for this screen is to select an appropriate or good segment which can be analyzed in detail. In the case of P-wave analyses, sometimes maneuvers may be performed to get unadulterated P-waves. These maneuvers may include drug infusion for AV dissociation or pacing to dissociate P-waves and R-waves. After an appropriate segment 362 is selected, by clicking on the continue button 363 the program proceeds to the analyses mode which is shown in conjunction with FIG. 32 in this disclosure. In the analyses screen, the segment 362 that was selected is displayed in a 12-lead format along with questions that the physician or operator needs to answer. In one example of this embodiment the question just below lead I is whether the P-wave is Flat or Negative 366. Advantageously, the question corresponding to each lead is displayed next to the morphology of the P-wave for that lead. After answering the question on Lead I, the physician or operator answers the questions on lead aVR 368, Inferior leads (II, III, aVF) 372 and Precordial leads 374 which include leads V1, V2, V3, V4, V5, and V6. When all the questions are answered by clicking the appropriate check boxes, the answer pops in a window which in this figure is shown in the bottom middle 369 of FIG. 32.

At any time during the process of filling out the screen, if the operator or physician feels that a different segment would be useful, they simply press the EKG Segment button 365 and the program takes them back to segment selection screen which was shown previously in FIG. 31. After re-selecting a different segment and pressing Continue 363 the program goes back to the screen shown in FIG. 32 for answering question. While the questions are being answered, a Back button (not shown) or a Reset button 367 allows the user to change or re-enter the answers.

Figure 33:
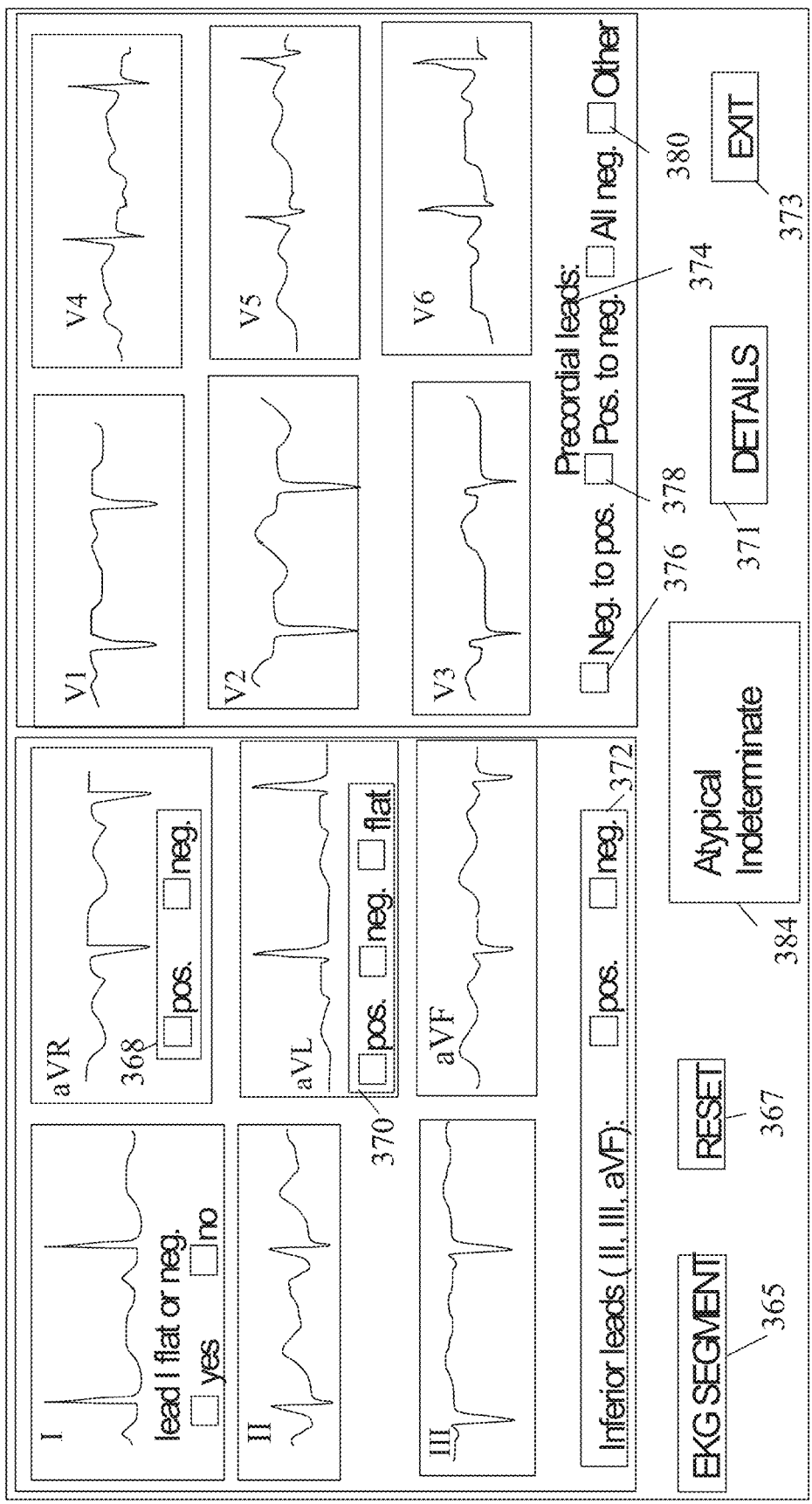
FIG. 33 shows the question answering screen for the AT localization program where the answer is "Atypical/Indeterminate".

As previously mentioned, when all the check boxes are completed, the answer appears on the screen. As shown in conjunction with FIG. 33, sometimes the answer is simply Indeterminate or Atypical 384. Further, by pressing the Details button as shown in the figure, a detailed explanation appears on the screen. When the EKG localization is complete the Exit button takes the user out of the program and into the main menu.

Figure 34:
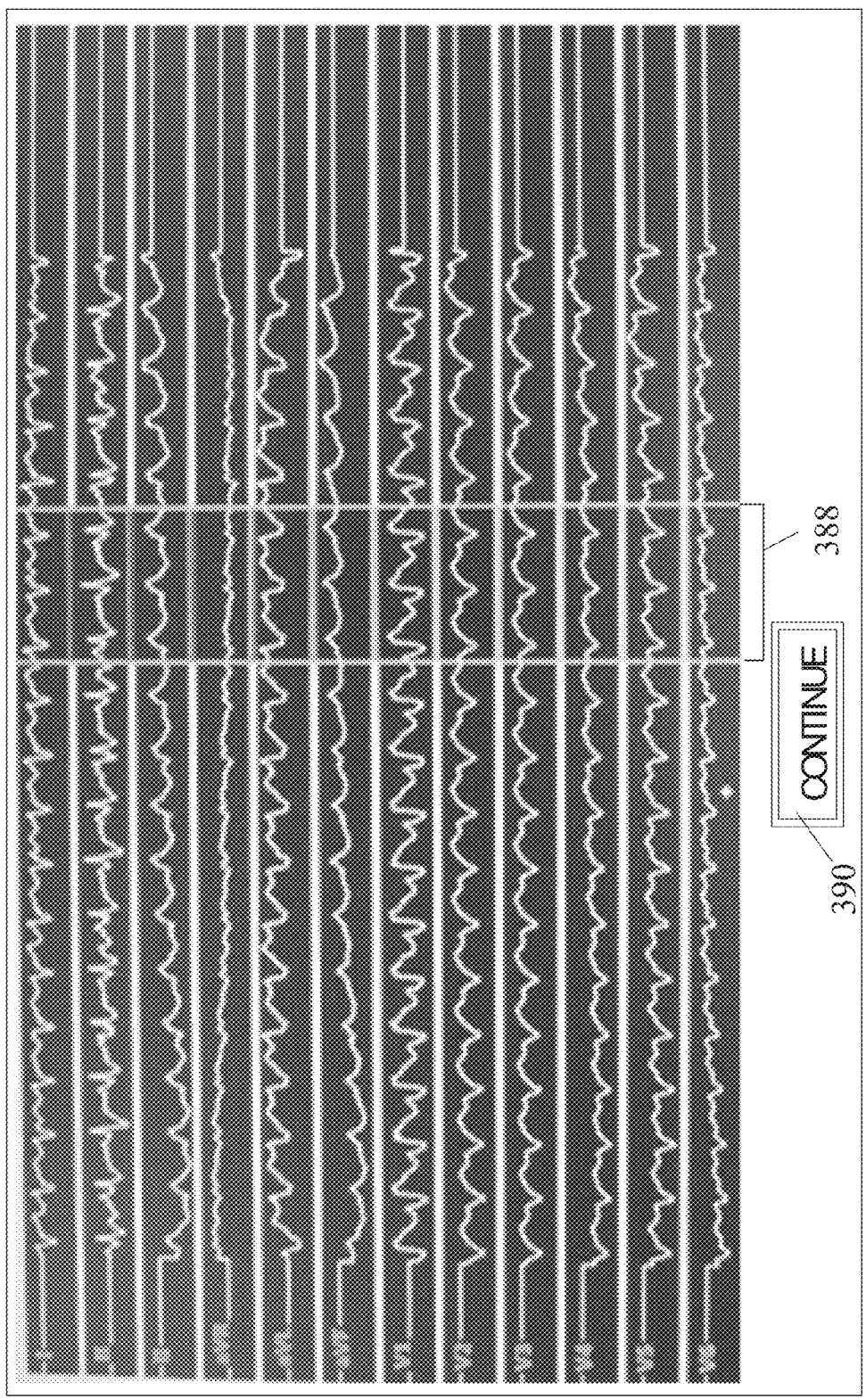
FIG. 34 shows the segment selection screen for the Ischemic VT localization part of the program.

In a similar methodology to the above AT program, when the VT button 254 which is shown in FIG. 30 is selected, the segment selection 388 for the VT program appears, which is shown in conjunction with FIG. 34. Once the proper screen is selected, and Continue button 390 is clicked, the next part of the program is displayed as is shown in conjunction with FIG. 35. In a similar fashion to the above described AT program, the 12-leads of the selected QRS segments are displayed on the screen. The physician or operator answers the questions regarding the location of the scar and the morphology of the QRS complex and the answer appears on the screen.

Figure 35:
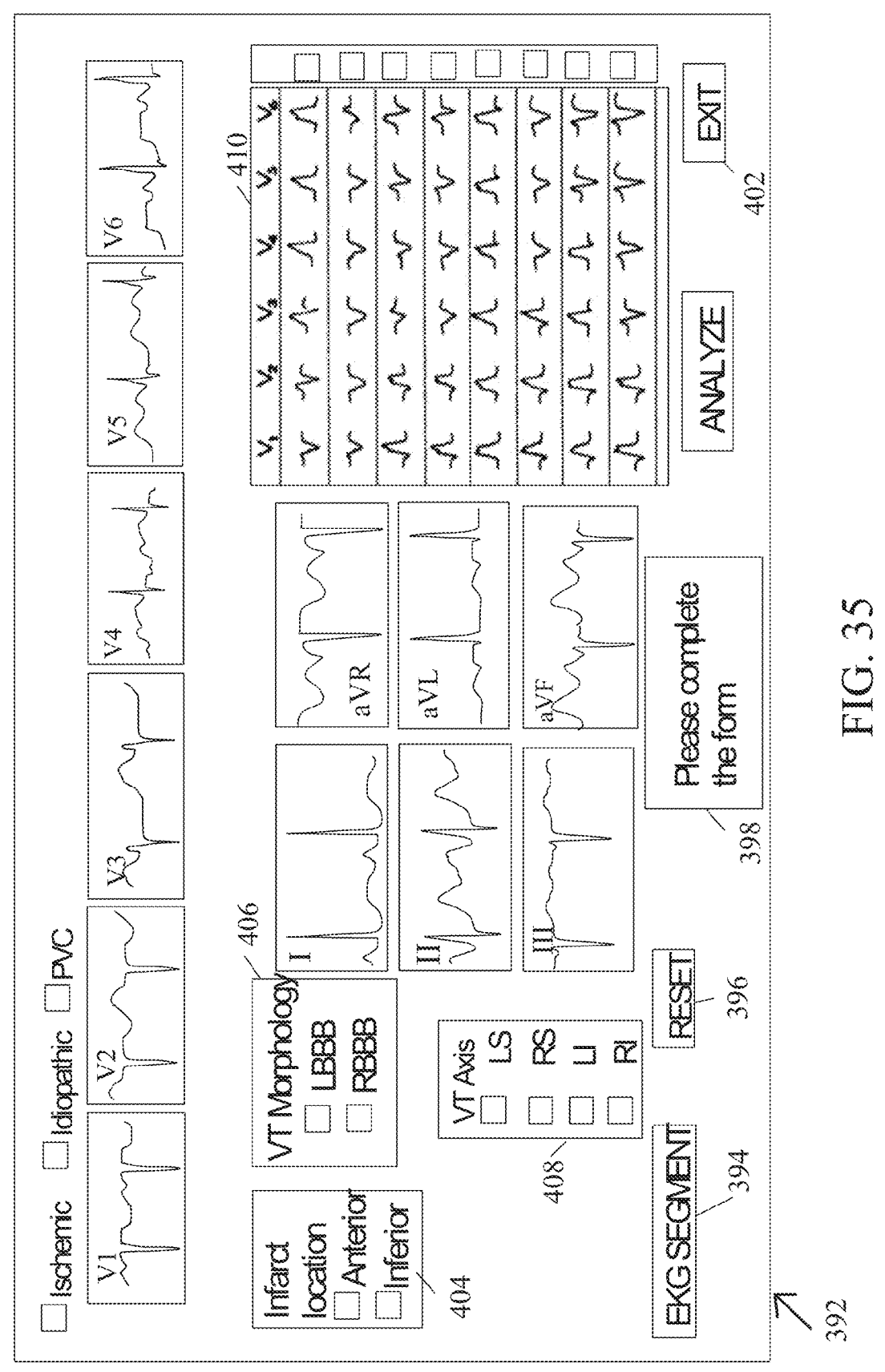
Figure 36:
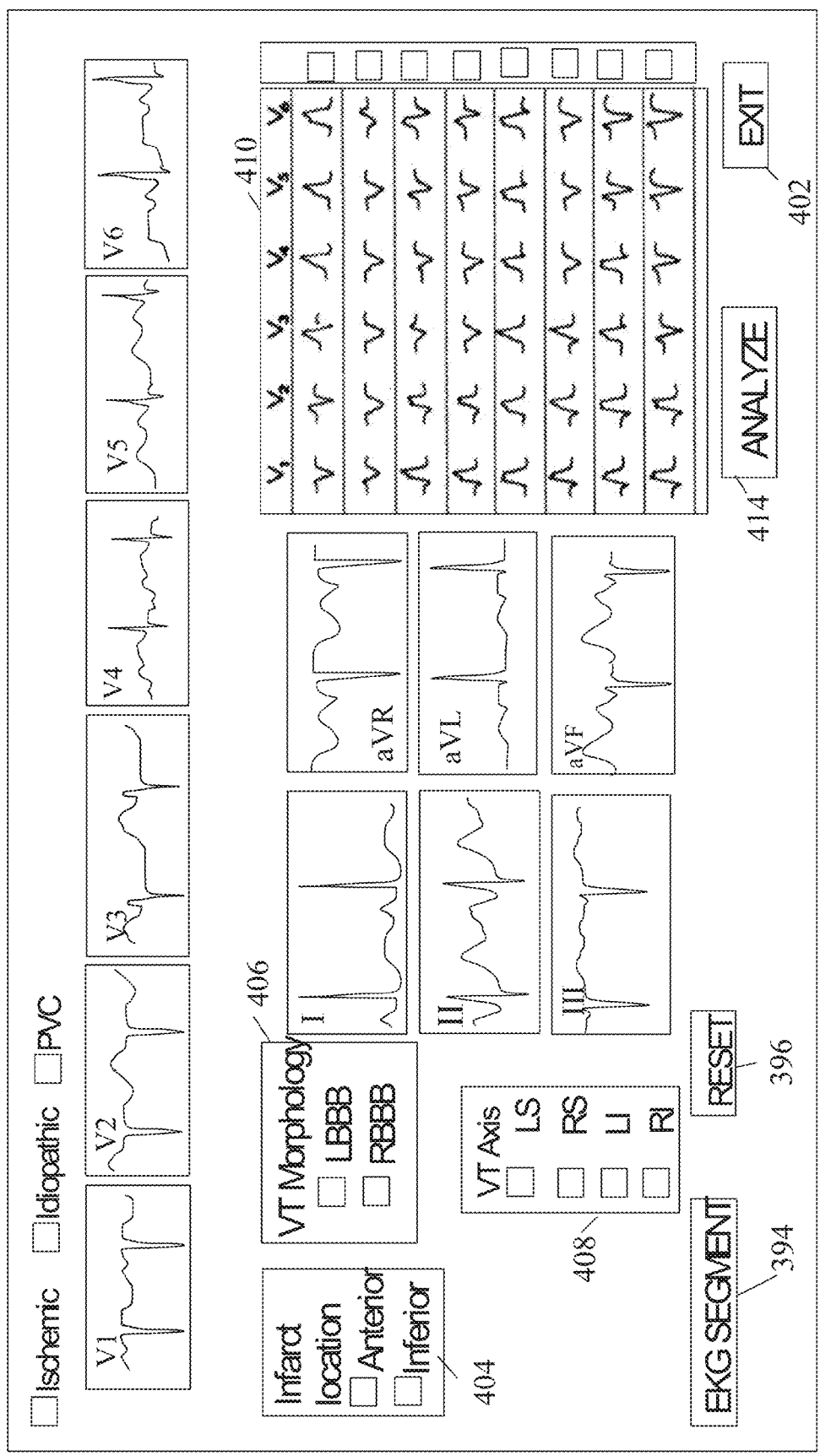
FIG. 36 shows the question answering screen of the Ischemic VT localization program, where the questions have been answered and the program is ready for analyses.
Figure 37:
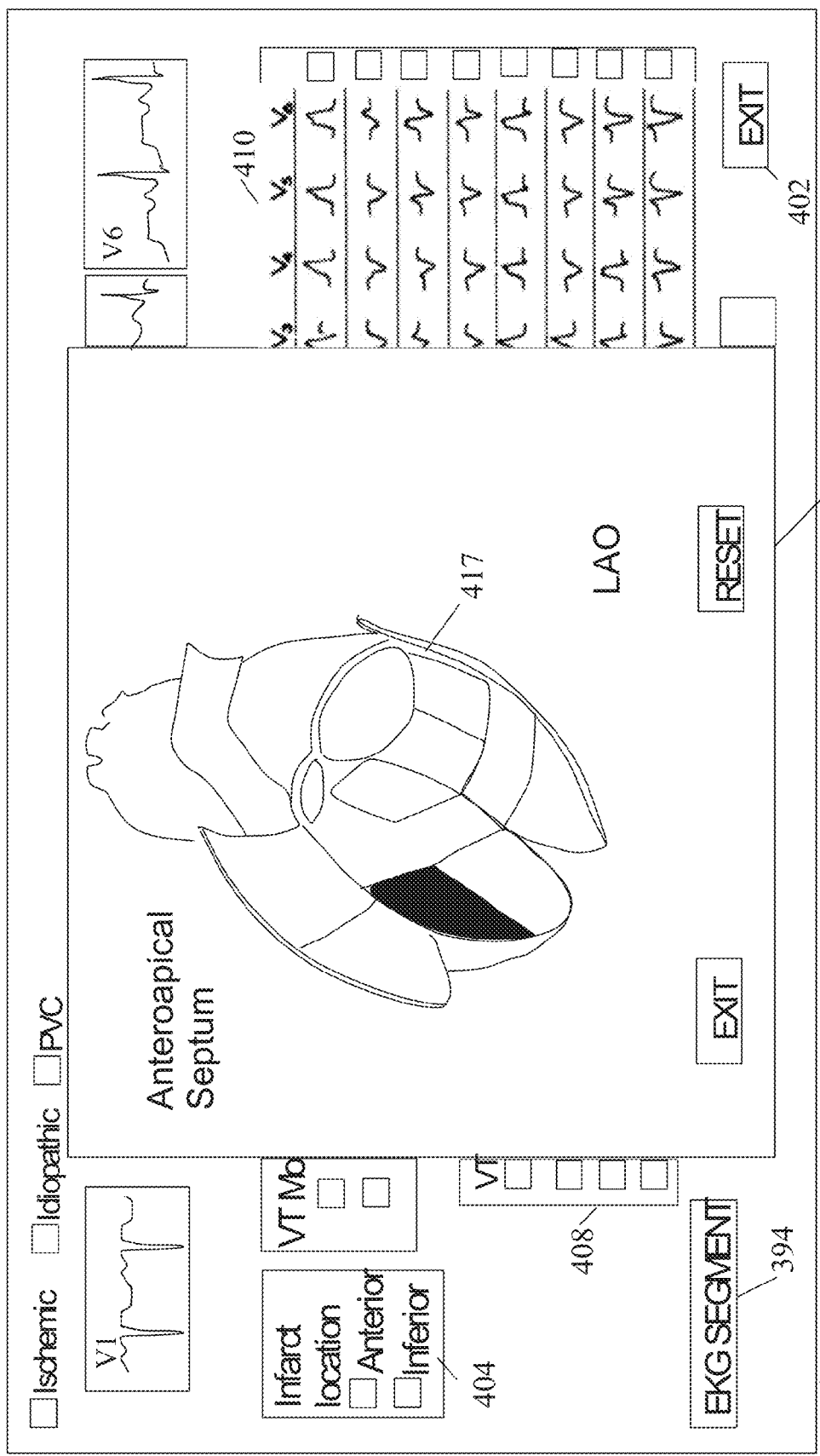
FIG. 37 shows the question answering screen of the Ischemic VT localization program, where the answer is displayed in graphical form.

As shown in FIG. 35, in one embodiment shown here as an example the physician or operator answers questions about whether the infarct is located Anterior or Inferior 404. There are other questions, such as whether the VT morphology has LBBB or RBBB 406 pattern. There is a box for VT Axis 408 whether it is LS, RS, LI, or RI. Further, in one embodiment a template may also be provided to match the most closest pattern for Precordial leads (V1, V2, V3, V4, V5, and V6). When all the boxes are appropriately checked, the Please Complete the Form 398 gets hidden, as is shown in FIG. 36. By clicking on the Analyze box 414 (FIG. 36), a picture of the heart 417 with shaded area of where the localization or regionalization is in the ventricle is displayed. This is shown in conjunction with FIG. 37. In one example, the physician or operator has the option to Reset and start over or to Exit from the program.

As was the case in the AT version of the program, some combination of answers may result in "Atypical/Indeterminate" answer which will be displayed on the screen. The operator then has the option to reset and change some of the answers, which may result in a localization site.

Figure 38:
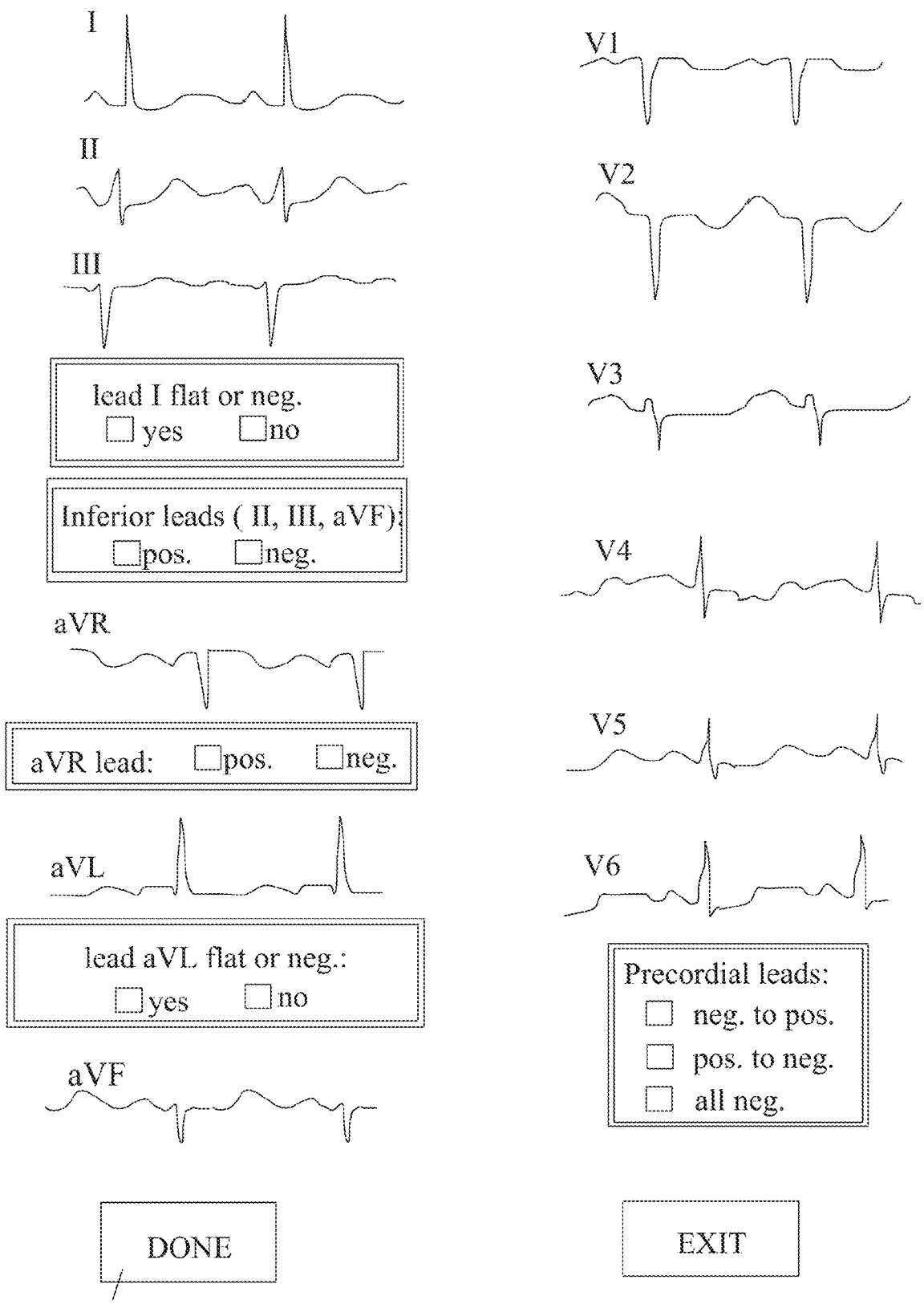
FIG. 38 shows another example of screen for the EKG localization program.

It will be clear to one skilled in the art that various modifications of the above can be implemented and are considered within the scope of the disclosure. For example, one modification of this implementation is shown in FIG. 38. As shown in the figure, once the answers to all the questions are checked off, the physician or operator clicks on the Done 418 button. This takes the program to an answer screen, where the EKG localization site is stated and any explanation is detailed.

Figure 39:
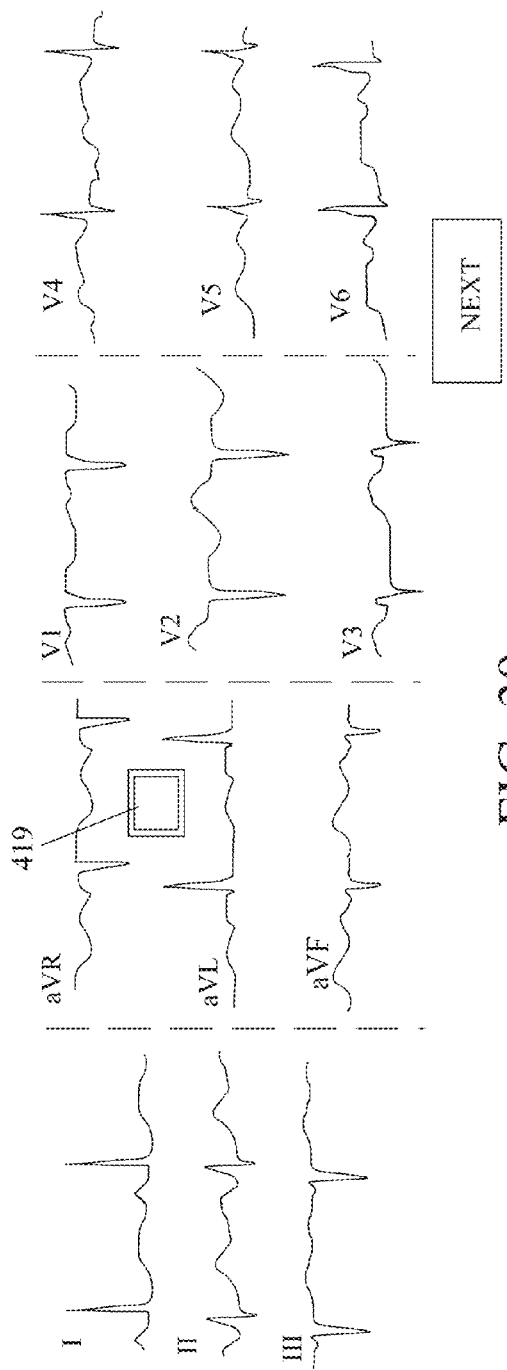
FIGS. 39 and 40 shown more examples of "interactive" EKG localization program.
Figure 40:
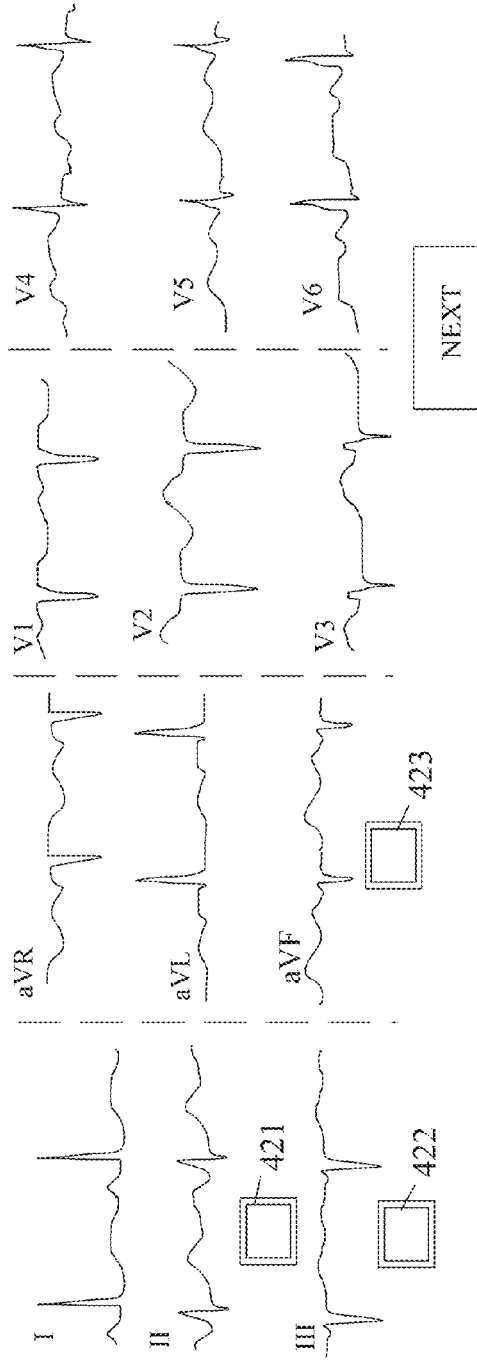

Yet another example of implementation is shown in conjunction with FIGS. 39-41. As shown in FIG. 39, as the screen appears on the display, the physician or operator answers the question about lead aVR 419 and clicks Next. Shown in FIG. 40, the operator then answers questions on Lead II 421, Lead III 422, and Lead aVF 423, then clicks on Next. As shown in FIG. 41, the suggested Results/diagnosis are displayed, and the operator has the option to move forward in the program by clicking Next 425 or going back in the program by clicking Back to Program 426 button. Various other modifications and combinations of these examples can be implemented, and are considered within the scope of this disclosure.

While this disclosure has been described with reference to preferred embodiments, it will be understood by those skilled in the art that various changes may be made without departing from the scope of the invention. In addition, many modifications may be made to adapt a particular situation or material to the teaching of the invention with departing from the essential scope thereof. Therefore, it is intended that the disclosure not be limited to the particular embodiments disclosed for carrying out this invention, but that the invention will include all embodiments falling within the scope of the appended claims.

The invention claimed is:

1. A method of providing cardiac mapping comprising the steps of: placing at least two catheters in the heart of a patient, wherein each of said catheters comprising at least one electrode pair, sensing an electrical signal arriving at said electrode pairs of each of said catheters; acquiring a heart fluoroscopic image of a patient and placing visual indicators on said heart fluoroscopic image which are positioned at and correspond with an image of said electrode pairs of said catheters and which detect said electrical signal arriving at said electrode pairs; and using a programmed computer, displaying, on a visual display, a visual indication of cardiac signal timing information, the visual indication being superimposed on said heart fluoroscopic image of the patient for said electrode pairs of each of said catheters, wherein the detection of said electrical signal at each of said electrode pairs of each of said catheters occurs at multiple regions of the heart substantially proximate in time with respect to each other and wherein the visual indication is displayed in real time with the detection of said electrical signal.

2. The method of claim 1, wherein the computer is programmed with software coded in at least one software language selected from the group consisting of LAB WINDOWS/CVIO, LABVIEW® (National Instruments Corp.), C+®, Microsoft Visual C++®, Dot Net Framework®, MATLAB®, and Microsoft Visual Basic®.

3. The method of claim 1, wherein said cardiac mapping can be used in ablation procedures for treating supraventricular or ventricular arrhythmias, comprising AVNRT (atrioventricular nodal reentry tachycardia), AVRT (atrio-ventricular reentry tachycardia), atrial flutter, atrial tachycardia, atrial fibrillation, RVOT (right ventricular outflow tract tachycardia), LVOT (left ventricular outflow tract tachycardia), and ischemic ventricular tachycardia.

4. The method of claim 1, wherein said visual display comprises light emitting diodes.

5. The method of claim 4, wherein said electrical signal arriving at said electrodes corresponds with an emission of light at said light emitting diodes.

6. The method of claim 1, wherein said electrical signal comprise at least one of intracardiac signals and surface cardiac signals.

7. The method of claim 1, wherein said heart fluoroscopic image comprises one of a CT image, an ultrasound image, an MRI image, a fluoroscopic image, a 3-D image, and one or more overlay thereof.

8. The method of claim 1, wherein the computer is programmed with at least one algorithm capable of identifying or measuring at least one of zone of slow conduction, post pacing interval (PPI), line of block in a cardiac ablation procedure; or measuring and/or displaying the early activation timing information continuously in real-time relative to a reference signal, wherein said activation timing information is relative to an intra-cardiac reference or surface EKG reference signal, wherein the reference signal is considered to be t=0; or analyzing a 12-lead EKG of a patient for localization/regionalization of an arrhythmia based upon operator input.

9. The method of claim 1, wherein each of said visual indicators comprises one of a blinking light emitting diode (LED), a flashing LED, a color coding LED, and a visually identifiable marker, and wherein the timing of the activation of said visual indicators is linked with said electrical signal.

10. The method of claim 1, further comprising displaying both a numeric value of local activation time continuously and said visual indicators in real-time.

11. The method of claim 1, further comprising displaying original template of clinical tachycardia and pace map morphologies side by side or superimposed on each other for template matching.

12. The method of claim 1, wherein said visual display further comprises using blinking LEDs at different times, different color LEDs, or color coding schemes for showing sequence of electrical activity at different anatomic locations in heart.

13. A method of cardiac mapping, comprising the steps of: placing at least two catheters in the heart of a patient, wherein each of said catheters comprise at least one electrode pair and sensing an electrical signal arriving at said electrode pairs of each of said catheters; acquiring a heart fluoroscopic image of a patient and placing visual indicators on said heart fluoroscopic image which are positioned at and correspond with an image of said electrode pairs of said catheters and which detect said electrical signal arriving at said electrode pairs; and using a programmed computer, linking cardiac signal timing information with said visual indicators, and displaying, on a visual display, a visual indication of said cardiac signal timing information, the visual indication being superimposed on said heart fluoroscopic image of the patient for said electrode pairs of each of said catheters, and wherein the visual indication is displayed in real time with the detection of said electrical signal.

14. The method of claim 13, wherein the computer is programmed with software coded in at least one software language selected from the group consisting of LAB WINDOWS/CVIO, LABVIEW® (National Instruments Corp.), C+®, Microsoft Visual C++®, Dot Net Framework®, MATLAB®, and Microsoft Visual Basic®.

15. The method of claim 13, wherein said heart fluoroscopic image comprises one of a CT (computed tomography)

image, an ultrasound image, a MRI (magnetic resonance image), a fluoroscopic image, a 3-D image, and one or more overlays thereof.

16. The method of claim 13, wherein said cardiac mapping can be used in ablation procedures for treating supraventricular or ventricular arrhythmias, comprising AVNRT (atrio-ventricular nodal reentry tachycardia), AVRT (atrio-ventricular reentry tachycardia), atrial flutter, atrial tachycardia, atrial fibrillation, RVOT (right ventricular outflow tract tachycardia), LVOT (left ventricular outflow tract tachycardia), ischemic ventricular tachycardia, accessory pathways including WPW, PVC mapping, and other focal or re-entry tachycardias.

17. The method of claim 13, further comprising automatically measuring post pacing interval (PPI), combining electroantomical mapping features with electrophysiological mapping including timing mapping, automation and clinical decision support, or checking line of block for atrial flutter ablation procedures and displaying at least one of: the numbers for checking for the line of block post ablation with CS pacing, the earliest activation information in real-time, along with earliest activation for the session, measuring the polarity of QRS complexes and determining automatically whether the polarity is positive, negative, or flat and storing that information in a table, which is used by the system for determining the localization or regionalization of the arrhythmia.

18. The method of claim 13, wherein said visual display comprises a plurality of LEDs, and wherein the LEDs emit light upon detection of said electrical signal at said electrodes.

19. The method of claim 13, wherein each of said visual indicators comprises one of a blinking light emitting diode (LEDD, a flashing LED, a color coding LED, and a visually identifiable marker or any other form of visual indicator(s), and further comprises using blinking, flashing or color coding schemes for showing a sequence of electrical activity at different anatomic locations in the heart.

20. A method of cardiac mapping, comprising the steps of: placing at least two catheters in the heart of a patient, wherein each of said catheters comprise at least one electrode pair and sensing an electrical signal arriving at said electrode pairs of each of said catheters; acquiring a heart fluoroscopic image of a patient and placing visual indicators on said heart fluoroscopic image which are positioned at and correspond with an image of said electrode pairs of said catheters and which detect said electrical signal arriving at said electrode pairs; and using a programmed computer, linking cardiac signal timing information with said visual indicators, and displaying, on a visual display, a visual indication of said cardiac signal timing information, the visual indication being superimposed on said heart fluoroscopic image of the patient for said electrode pairs of each of said catheters, and wherein the sensing of said electrical signal at each of said electrode pairs of each of said catheters occurs at multiple regions of the heart substantially proximate in time with respect to each other, wherein the visual indication is displayed in real time with detection of said electrical signal, and wherein said visual indicators are LEDs which emit light upon detection of an electrical signal at said electrode pairs.

* * * * *